(12) United States Patent
Larsen et al.

(10) Patent No.: US 7,902,230 B2
(45) Date of Patent: Mar. 8, 2011

(54) BENZIMIDAZOLE DERIVATIVES AND THEIR USE FOR MODULATING THE GABA$_A$ RECEPTOR COMPLEX

(75) Inventors: Janus S. Larsen, Holbæk (DK); Lene Teuber, Værlese (DK); Philip K. Ahring, Bagsvaerd (DK); Elsebet Østergaard Nielsen, København K (DK); Naheed Mirza, Birkerød (DK)

(73) Assignee: Neurosearch A/S, Ballerup (DK)

( * ) Notice: Subject to any disclaimer, the term of this patent is extended or adjusted under 35 U.S.C. 154(b) by 286 days.

(21) Appl. No.: 12/279,511

(22) PCT Filed: Mar. 22, 2007

(86) PCT No.: PCT/EP2007/052766
§ 371 (c)(1),
(2), (4) Date: Aug. 14, 2008

(87) PCT Pub. No.: WO2007/110374
PCT Pub. Date: Oct. 4, 2007

(65) Prior Publication Data
US 2009/0036476 A1  Feb. 5, 2009

Related U.S. Application Data

(60) Provisional application No. 60/785,278, filed on Mar. 24, 2006, provisional application No. 60/851,284, filed on Oct. 13, 2006.

(30) Foreign Application Priority Data

Mar. 24, 2006  (DK) ................... 2006 00426
Oct. 12, 2006  (DK) ................... 2006 01327

(51) Int. Cl.
*A61K 31/4439* (2006.01)
*C07D 401/10* (2006.01)

(52) U.S. Cl. ..................................... 514/338; 546/273.4

(58) Field of Classification Search ............... 546/273.4; 514/338
See application file for complete search history.

(56) References Cited

U.S. PATENT DOCUMENTS

| 5,360,809 | A | * | 11/1994 | Axelsson et al. ............. 514/338 |
| 5,554,630 | A | * | 9/1996 | Teuber et al. ................ 514/338 |
| 2006/0116402 | A1 | | 6/2006 | Crew et al. |

FOREIGN PATENT DOCUMENTS

| EP | 0 616 807 A1 | 9/1994 |
| WO | WO-96/33191 A | 10/1996 |
| WO | WO-96/33192 A | 10/1996 |
| WO | WO 96/33194 A1 | 10/1996 |
| WO | WO-99/19323 A | 4/1999 |
| WO | WO-2007/065864 A | 6/2004 |
| WO | WO-2004/087137 A | 10/2004 |
| WO | WO-2004/087690 A | 10/2004 |
| WO | WO 2006/069381 A2 | 5/2006 |
| WO | WO-2006/108800 A | 10/2006 |
| WO | WO-2008/008059 A1 | 1/2008 |

* cited by examiner

*Primary Examiner* — Joseph R Kosack
*Assistant Examiner* — Matthew P Coughlin
(74) *Attorney, Agent, or Firm* — Birch, Stewart, Kolasch & Birch, LLP

(57) ABSTRACT

This invention relates to novel benzimidazole derivatives, pharmaceutical compositions containing these compounds, and methods of treatment therewith.
The compounds of the invention are useful in the treatment of central nervous system diseases and disorders which are responsive to modulation of the GABA$_A$ receptor complex, and in particular for combating anxiety and related diseases.

6 Claims, No Drawings

BENZIMIDAZOLE DERIVATIVES AND THEIR USE FOR MODULATING THE GABA$_A$ RECEPTOR COMPLEX

This application is the National Phase of PCT/EP2007/052766 filed on Mar. 22, 2007, which claims priority under 35 U.S.C. 119(e) to U.S. Provisional Application No. 60/785,278 and 60/851,284 filed on Mar. 24, 2006 and Oct. 13, 2006 and under 35 U.S.C. 119(a) to patent application Ser. No. PA 2006 00426 and PA 2006 01327 filed in Denmark on Mar. 24, 2006 and Oct. 12, 2006; respectively. All of these prior applications are hereby expressly incorporated by reference into the present application.

TECHNICAL FIELD

This invention relates to novel benzimidazole derivatives, pharmaceutical compositions containing these compounds, and methods of treatment therewith.

The compounds of the invention are useful in the treatment of central nervous system diseases and disorders which are responsive to modulation of the GABA$_A$ receptor complex, and in particular for combating anxiety and related diseases.

BACKGROUND ART

The modulatory sites on the GABA$_A$ receptor complex, such as for example the benzodiazepine binding site, are the target for anxiolytic drugs, such as the classical anxiolytic benzodiazepines. However, they are associated with a number of undesirable features.

Multiple isoforms of the GABA$_A$ receptor exist; each receptor is a pentameric complex comprising subunits drawn from $\alpha_{1-6}$, $\beta_{1-3}$, $\gamma_{1-3}$, $\delta$, $\epsilon$, and $\theta$ subunit isoforms. The classical anxiolytic benzodiazepines show no subtype selectivity. It has been suggested that one of the key elements in the disadvantages of the classical benzodiazepanes (such as sedation, dependency, and cognitive impairment) is relates to the $\alpha$1 subunit of the GABA$_A$ receptors. Thus compounds with selectivity for the $\alpha$2 and/or $\alpha$3 subunits over the $\alpha$1 subunit are expected to have an improved side effect profile.

Thus, there is still a strong need for compounds with an optimised pharmacological profile. Furthermore, there is a strong need to find effective compounds without unwanted side effects associated with older compounds.

SUMMARY OF THE INVENTION

In its first aspect, the invention provides a compound of Formula I:

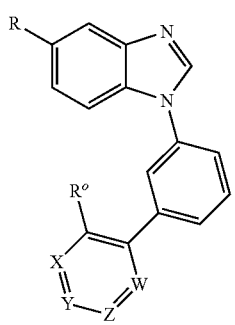

or an N-oxide thereof, any of its isomers or any mixture of its isomers, or a pharmaceutically acceptable salt thereof, wherein R, R$^o$, X, Y, Z and W are defined as below.

In its second aspect, the invention provides a pharmaceutical composition, comprising a therapeutically effective amount of a compound of the invention, or an N-oxide thereof, any of its isomers or any mixture of its isomers, or a pharmaceutically acceptable salt thereof, together with at least one pharmaceutically acceptable carrier, excipient or diluent.

In a further aspect, the invention provides the use of a compound of the invention, or an N-oxide thereof, any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of the GABA$_A$ receptor complex.

In a still further aspect, the invention relates to a method for treatment, prevention or alleviation of a disease or a disorder or a condition of a living animal body, including a human, which disorder, disease or condition is responsive to modulation of the GABA$_A$ receptor complex, which method comprises the step of administering to such a living animal body in need thereof a therapeutically effective amount of a compound of the invention, or an N-oxide thereof, any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

Substituted Benzimidazole Derivatives

In its first aspect the present invention provides a compound of general formula I:

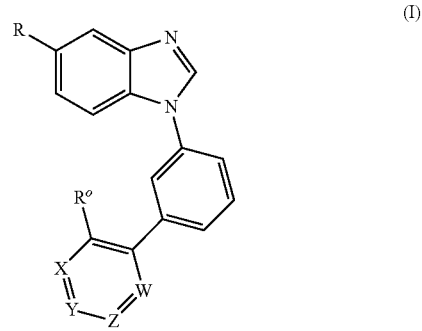

or an N-oxide thereof, any of its isomers or any mixture of its isomers,
or a pharmaceutically acceptable salt thereof; wherein
R represents
-alkyl-OR$^a$, —C(R$^a$)=N—O—R$^b$, —C(=N—R$^a$)—NH—O—R$^b$, —(C=O)—R$^a$, —(C=O)—NR$^a$R$^b$ or —(C=O)—O—R$^a$;
  wherein R$^a$ and R$^b$ independent of each other is hydrogen or alkyl;
—(R'R'')$_n$—R$^c$;
  wherein R$^c$ represents halo, trifluoromethyl, trifluoromethoxy, cyano, nitro, alkyl or alkoxy;
R' and R'' independent of each other is hydrogen, hydroxy or alkyl;

n is 0 or 1; or
a heterocyclic ring;
which heterocyclic ring may optionally be substituted with halo, trifluoromethyl, trifluoromethoxy, cyano, nitro, alkyl, hydroxy or alkoxy;
X, Y, Z and W independent of each other represent N or $CR^d$;
wherein each $R^d$ is independently selected from the group consisting of:
hydrogen, halo, trifluoromethyl, trifluoromethoxy, cyano, nitro, alkyl, hydroxy and alkoxy;
$R^o$ represents
halo, trifluoromethyl, trifluoromethoxy, cyano, nitro, alkyl, —(C=O)—$R^e$, —(C=O)—$NR^eR^f$, —$C(R^e)$=N—O—$R^f$, —N($R^e$)—$SO_2$—$R^f$, —$SO_2$—$NR^eR^f$, hydroxy, hydroxyalkyl, alkoxy or alkoxyalkyl;
wherein $R^e$ and $R^f$ independent of each other is hydrogen or alkyl; or
—(CR'''R'''')$_m$—$R^g$;
wherein $R^g$ represents a heterocyclic ring,
which heterocyclic ring may optionally be substituted with: halo, trifluoromethyl, trifluoromethoxy, cyano, nitro, alkyl, hydroxy or alkoxy;
R''' and R'''' independent of each other is hydrogen or alkyl; and
m is 0 or 1;
or $R^o$ together with one of the $R^d$ forms methylenedioxy or ethylenedioxy.

In one embodiment of the compound of general formula (I), R represents -alkyl-$OR^a$, —$C(R^a)$=N—O—$R^b$, —C(=N—$R^a$)—NH—O—$R^b$, —(C=O)—$R^a$, —(C=O)—$NR^aR^b$ or —(C=O)—O—$R^a$; wherein $R^a$ and $R^b$ independent of each other is hydrogen or alkyl. In a special embodiment, $R^a$ represents hydrogen. In a further embodiment, $R^a$ represents alkyl, such as methyl. In a still further embodiment, $R^b$ represents hydrogen. In a still further embodiment, $R^b$ represents alkyl, such as methyl. In a special embodiment, R represents —C(=NH)—NH—OH.

In a special embodiment, R represents -alkyl-$OR^a$, —$C(R^a)$=N—O—$R^b$, —C(=N—$R^a$)—NH—O—$R^b$, (C=O)—$R^a$, or —(C=O)—O—$R^a$; wherein $R^a$ and $R^b$ independent of each other is hydrogen or alkyl;

In a further embodiment, R represents -alkyl-$OR^a$. In a special embodiment, R represents -alkyl-OH, such as 1-hydroxy-ethyl.

In a still further embodiment, R represents —$C(R^a)$=N—O—$R^b$. In a special embodiment, R represents —$C(R^a)$=N—OH, such as —C($CH_3$)=N—OH or —C(H)=N—OH. In a further embodiment, R represents —$C(R^a)$=N—$CH_3$, such as —C($CH_3$)=N—$CH_3$ or —C(H)=N—$CH_3$.

In a still further embodiment, R represents —C(=N—$R^a$)—NH—O—$R^b$, such as —C(=NH)—NH—OH.

In a further embodiment, R represents —(C=O)—$R^a$, such as formyl or acetyl.

In a still further embodiment, R represents —(C=O)—$NR^aR^b$, such as aminocarbonyl.

In a further embodiment of the compound of general formula (I), R represents —(CR'R")$_n$—$R^c$; wherein $R^c$ represents halo, trifluoromethyl, trifluoromethoxy, cyano, nitro, alkyl or alkoxy; R' and R" independent of each other is hydrogen, hydroxy or alkyl; and n is 0 or 1.

In a special embodiment, R' represents hydrogen. In a further embodiment, R' represents hydroxy. In a still further embodiment, R' represents alkyl, such as methyl In a still further embodiment, R" represents hydrogen. In a further embodiment, R" represents hydroxy. In a still further embodiment, n is 0. In a further embodiment, n is 1. In a further embodiment, $R^c$ represents alkyl, such as methyl. In a special embodiment, R represents 1-hydroxy-ethyl or 1-hydroxy-1-methyl-ethyl.

In a special embodiment, R represents cyano. In a further embodiment, R represents trifluoromethyl. In a still further embodiment, R represents 1-hydroxy-2,2,2-trifluoro-ethyl. In a further embodiment, R represents 1-hydroxy-prop-2-ynyl. In a still further embodiment, R represents 2,2,2-trifluoro-1,1-dihydroxy-ethyl.

In a further embodiment of the compound of general formula (I), R represent a heterocyclic ring; which heterocyclic ring may optionally be substituted with halo trifluoromethyl, trifluoromethoxy, cyano, nitro, alkyl, hydroxy or alkoxy.

In a special embodiment, R represents optionally substituted isoxazolyl, such as optionally substituted isoxazol-5-yl, such as isoxazol-5-yl. In a further embodiment, R represent optionally substituted pyrazolyl, such as optionally substituted 2H-pyrazol-3-yl, such as 2H-pyrazol-3-yl. In a further embodiment, R represent optionally substituted 4,5-dihydro-1H-imidazolyl, such as optionally substituted 4,5-dihydro-1H-imidazol-2-yl, such as 4,5-dihydro-1H-imidazol-2-yl. In a still further embodiment, R represents optionally substituted pyrimidyl, such as optionally substituted pyrimidin-2-yl. In a special embodiment, R represents amino-pyrimidyl, such as 6-amino-pyrimidin-2-yl. In a further embodiment, R represents optionally substituted oxazolyl, such as oxazolyl, such as oxazol-5-yl.

In a still further embodiment of the compound of general formula (I), X, Y, Z and W independent of each other represent $CR^d$; wherein each $R^d$ is independently selected from the group consisting of: hydrogen, halo, trifluoromethyl, trifluoromethoxy, cyano, nitro, alkyl, hydroxy and alkoxy.

In a special embodiment,

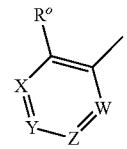

represents

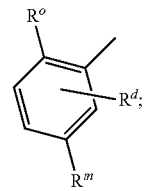

wherein $R^m$ represents hydrogen, halo, trifluoromethyl, trifluoromethoxy, cyano, nitro, alkyl, hydroxy or alkoxy; and $R^d$ represents hydrogen, halo, trifluoromethyl, trifluoromethoxy, cyano, nitro, alkyl, hydroxy or alkoxy. In a further embodiment, $R^m$ represents hydrogen. In a still further embodiment, $R^m$ represents halo, such as fluoro, bromo or chloro. In a further embodiment, $R^m$ represents alkyl, such as methyl. In a still further embodiment, $R^m$ represents cyano. In a still further embodiment, $R^d$ represents hydrogen.

In a further special embodiment,

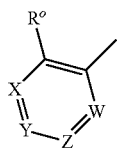

represents

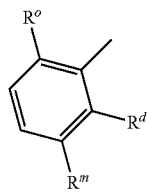 or 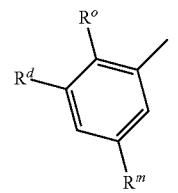 or

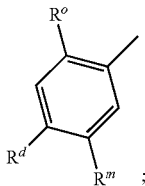 ;

wherein $R^d$ represents halo, trifluoromethyl, trifluoromethoxy, cyano, nitro, alkyl, hydroxy or alkoxy. In a special embodiment, $R^d$ represents alkoxy, such as methoxy. In a further embodiment, $R^d$ represents halo, such as chloro or fluoro. In a further embodiment,

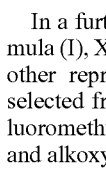

represents

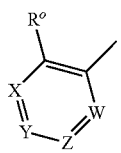

wherein $R^m$ represents hydrogen, halo, trifluoromethyl, trifluoromethoxy, cyano, nitro, alkyl, hydroxy or alkoxy; and $R^{d1}$ and $R^{d2}$ independent of each other represent halo, trifluoromethyl, trifluoromethoxy, cyano, nitro, alkyl, hydroxy or alkoxy. In one embodiment, $R^{d1}$ represents alkyl, such as methyl. In a further embodiment, $R^{d1}$ represents halo, such as fluoro or chloro. In a still further embodiment, $R^{d2}$ represents alkyl, such as methyl. In a further embodiment, $R^{d2}$ represents halo, such as fluoro or chloro.

In a special embodiment,

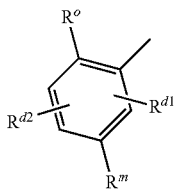

represents

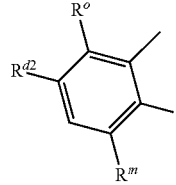 or 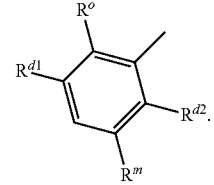.

In a further embodiment of the compound of general formula (I), X represents N; and Y, Z and W independent of each other represent $CR^d$; wherein each $R^d$ is independently selected from the group consisting of: hydrogen, halo, trifluoromethyl, trifluoromethoxy, cyano, nitro, alkyl, hydroxy and alkoxy.

In a special embodiment,

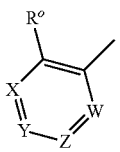

represents

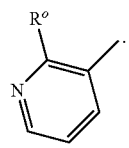

In a further special embodiment,

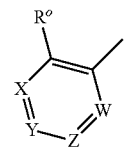

represents

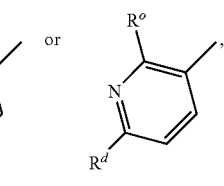

wherein $R^d$ is selected from the group consisting of: halo, trifluoromethyl, trifluoromethoxy, cyano, nitro, alkyl, hydroxy and alkoxy. In one embodiment $R^d$ represents halo, such as bromo or fluoro.

In a further embodiment of the compound of general formula (I), Y represents N; and X, Z and W independent of each other represent $CR^d$; wherein each $R^d$ is independently selected from the group consisting of: hydrogen, halo, trifluoromethyl, trifluoromethoxy, cyano, nitro, alkyl, hydroxy and alkoxy.

In a special embodiment,

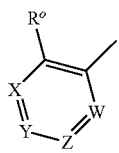

represents

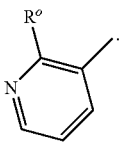

In a further special embodiment,

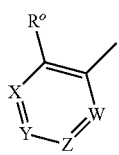

represents

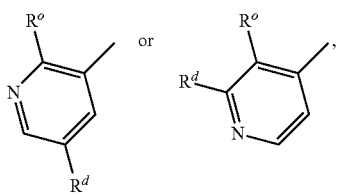

wherein $R^d$ is selected from the group consisting of: halo, trifluoromethyl, trifluoromethoxy, cyano, nitro, alkyl, hydroxy and alkoxy. In one embodiment $R^d$ represents halo, such as bromo or chloro.

In a still further embodiment of the compound of general formula (I), X represents N; Z represents N; and Y and W independent of each other represent $CR^d$; wherein each $R^d$ is independently selected from the group consisting of: hydrogen, halo, trifluoromethyl, trifluoromethoxy, cyano, nitro, alkyl, hydroxy and alkoxy.

In a special embodiment

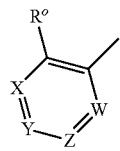

represents

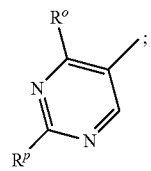

wherein $R^p$ represents hydrogen, halo, trifluoromethyl, trifluoromethoxy, cyano, nitro, alkyl, hydroxy or alkoxy. In a special embodiment, $R^p$ represents alkoxy, such as methoxy.

In a further embodiment of the compound of general formula (I), $R^o$ represents halo, trifluoromethyl, trifluoromethoxy, cyano, nitro, alkyl, —(CO)—$R^e$, —(C=O)—$NR^eR^f$, —C($R^e$)=N—O—$R^f$, —N($R^e$)—$SO_2$—$R^f$, —$SO_2$—$NR^eR^f$, hydroxy, hydroxyalkyl, alkoxy or alkoxyalkyl; wherein $R^e$ and $R^f$ independent of each other is hydrogen or alkyl.

In a special embodiment, $R^o$ represents halo, such as chloro or fluoro. In a further embodiment, $R^o$ represents trifluoromethoxy. In a still further embodiment, $R^o$ represents cyano. In a further embodiment, $R^o$ represents alkyl, such as methyl or ethyl. In a still further embodiment, $R^o$ represents —(C=O)—$R^e$, such as acetyl. In a further embodiment, $R^o$ represents —(C=O)—$NR^eR^f$, such as aminocarbonyl.

In a still further embodiment, $R^o$ represents —C($R^e$)=N—O—$R^f$. In a special embodiment, $R^o$ represents —C($R^e$)=N—OH, such as —C(CH$_3$)=N—OH. In a further embodiment, $R^o$ represents —C($R^e$)=N—CH$_3$, such as —C(CH$_3$)=N—CH$_3$.

In a further embodiment, $R^o$ represents —N($R^e$)—$SO_2$—$R^f$, such as methylsulfonyl-amino. In a still further embodiment, $R^o$ represents —$SO_2$—$NR^eR^f$, such as dimethyl-aminosulfonyl. In a further embodiment, $R^o$ represents hydroxy. In a still further embodiment, $R^o$ represents hydroxyalkyl, such as such as 1-hydroxy-ethyl. In a further embodiment, $R^o$ represents alkoxy, such as methoxy, ethoxy or isopropoxy. In a still further embodiment, $R^o$ represents alkoxyalkyl, such as methoxymethyl or 1-ethoxy-ethyl.

In a still further embodiment of the compound of general formula (I), $R^o$ represents —(CR'''R'''')$_m$—$R^g$; wherein $R^g$ represents a heterocyclic ring, which heterocyclic ring may optionally be substituted with: halo, trifluoromethyl, trifluoromethoxy, cyano, nitro, alkyl, hydroxy or alkoxy; R''' and R'''' independent of each other is hydrogen or alkyl; and m is 0 or 1.

In a special embodiment, R''' represents hydrogen. In a further embodiment, R'''' represents hydrogen. In a still further embodiment, m is o. In a further embodiment, m is 1.

In a further embodiment, $R^g$ represents substituted pyrazolyl, such as optionally substituted 2H-pyrazol-3-yl, such as 2H-pyrazol-3-yl. In a still further embodiment, $R^g$ represents optionally substituted isoxazolyl, such as optionally substituted isoxazol-3-yl, such as isoxazol-3-yl. In a further embodiment, $R^g$ represents optionally morpholinyl, such as morpholin-4-yl. In a further embodiment, $R^g$ represents optionally piperazinyl, such as piperazin-1-yl.

In a still further embodiment of the compound of general formula (I), $R^o$ together with one of the $R^d$ forms methylenedioxy or ethylenedioxy. In a special embodiment X represents $CR^d$; and $R^o$ together with said $R^d$ represents methylenedioxy. In a further embodiment, X represents $CR^d$; Y, Z and W each represent CH; and $R^o$ together with said $R^d$ represents methylenedioxy.

In a special embodiment of the compound of general formula (I),

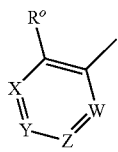

is selected from the group consisting of: 2-methoxy-phenyl, 2-ethoxy-phenyl, 2-methoxy-3-fluoro-phenyl, 2-methoxy-4-fluoro-phenyl, 2-methoxy-5-fluoro-phenyl, 2-methoxy-6-fluoro-phenyl, 2-methoxy-4-chloro-phenyl, 2-methoxy-5-chloro-phenyl, 2-methoxy-6-chloro-phenyl, 2-trifluoromethoxy-phenyl, 2-cyano-phenyl, 2-hydroxy-phenyl, 2-acetyl-phenyl, 2-carbamoyl-phenyl, 2-methyl-phenyl, 2-ethyl-phenyl, 2-(1-hydroxy-ethyl)-phenyl, 2-(1-ethoxy-ethyl)-phenyl, 2-isopropoxy-phenyl, 2-chloro-phenyl, 2-fluoro-phenyl, 2-hydroxy-3-chloro-phenyl, 2-chloro-5-cyano-phenyl, 2,6-dichloro-phenyl, 2,6-difluoro-phenyl, 2,3-dimethoxy-phenyl, 2,4-dimethoxy-phenyl, 2,6-dimethoxy-phenyl, 2-(morpholin-4-yl-methyl)-phenyl, 2-(N,N-dimethylsulphamoyl)-phenyl, 2-(piperazin-1-yl)-phenyl, 2-(isoxazol-5-yl)-phenyl, 2-pyrazol-3-yl)-phenyl, 2-(methoxysulfonylamino)-phenyl, 3-chloro-2,6-difluoro-phenyl, 2-chloro-6-fluoro-3-methoxy-phenyl, 6-chloro-2-fluoro-3-methoxy-phenyl, 3,5-di-fluoro-2-methoxy-phenyl, 2,3-difluoro-6-methoxy-phenyl, 2-fluoro-pyridin-3-yl, 2-chloro-pyridin-3-yl, 2-methoxy-pyridin-3-yl, 2,6-difluoro-pyridin-3-yl, 3-fluoro-pyridin-4-yl, 3-chloro-pyridin-4-yl, 2-fluoro-5-bromo-pyridin-3-yl, 2-bromo-5-fluoro-pyridin-3-yl, 2-chloro-3-fluoro-pyridin-4-yl, 2-bromo-5-methoxy-pyridin-4-yl, 2,4-dimethoxy-pyrimidin-5-yl, and benzo[1,3]-dioxol-4-yl.

In a special embodiment the chemical compound of the invention is
1-(4'-Fluoro-2'-methoxy-biphenyl-3-yl)-5-trifluoromethyl-1H-benzoimidazole;
1-(2'-Trifluoromethoxy-biphenyl-3-yl)-5-trifluoromethyl-1H-benzoimidazole;
1-(2'-Acetyl-biphenyl-3-yl)-5-trifluoromethyl-1H-benzoimidazole;
1-(4'-Chloro-2'-methoxy-biphenyl-3-yl)-5-trifluoromethyl-1H-benzoimidazole;
1-(2'-Methoxy-biphenyl-3-yl)-5-1H-benzoimidazole-5-carboxylic acid amide;
1-(2'-Methyl-biphenyl-3-yl)-5-trifluoromethyl-1H-benzoimidazole;
1-(2'-Methoxy-biphenyl-3-yl)-5-trifluoromethyl-1H-benzoimidazole;
1-(2'-Isopropoxy-biphenyl-3-yl)-5-trifluoromethyl-1H-benzoimidazole;
1-(2'-Cyano-biphenyl-3-yl)-5-trifluoromethyl-1H-benzoimidazole;
1-(2'-Ethoxy-biphenyl-3-yl)-5-trifluoromethyl-1H-benzoimidazole;
1-(2'-Ethyl-biphenyl-3-yl)-5-trifluoromethyl-1H-benzoimidazole;
1-(2'-Methanesulfonamido-biphenyl-3-yl)-5-trifluoromethyl-1H-benzoimidazole;
1-(2'-(Morpholin-4-yl-methyl)-biphenyl-3-yl)-5-trifluoromethyl-1H-benzoimidazole;
1-(2'-Hydroxy-biphenyl-3-yl)-5-trifluoromethyl-1H-benzoimidazole;
1-(2'-(N,N-Dimethyl-sulphamoyl)-biphenyl-3-yl)-5-trifluoromethyl-1H-benzoimidazole;
1-(2'-Methoxymethyl-biphenyl-3-yl)-5-trifluoromethyl-1H-benzoimidazole;
1-(2'-Chloro-biphenyl-3-yl)-5-trifluoromethyl-1H-benzoimidazole;
5-Acetyl-1-(2'-cyano-biphenyl-3-yl)-1H-benzoimidazole;
1-(2'-Methoxy-biphenyl-3-yl)-1H-benzoimidazole-5-carbonitrile;
1-(2'-Cyano-biphenyl-3-yl)-1H-benzoimidazole-5-carbonitrile;
1-(2'-Chloro-biphenyl-3-yl)-1H-benzoimidazole-5-carbonitrile;
1-(2'-isopropoxy-biphenyl-3-yl)-1H-benzoimidazole-5-carbonitrile;
1-(2'-Ethoxy-biphenyl-3-yl)-1H-benzoimidazole-5-carbonitrile;
1-(2'-Methyl-biphenyl-3-yl)-1H-benzoimidazole-5-carbonitrile;
1-(2'-Ethyl-biphenyl-3-yl)-1H-benzoimidazole-5-carbonitrile;
1-(5'-Fluoro-2'-methoxy-biphenyl-3-yl)-1H-benzoimidazole-5-carbonitrile;
1-(2'-Acetyl-biphenyl-3-yl)-1H-benzoimidazole-5-carbonitrile;
5-Acetyl-[3-(2-hydroxy-pyridin-3-yl)-phenyl]-1H-benzoimidazole;
5-Acetyl-[3-(2-methoxy-pyridin-3-yl)-phenyl]-1H-benzoimidazole;
5-(1-Hydroxy-2,2,2-trifluoro-ethyl)-1-(2'-methoxy-biphenyl-3-yl)-1H-benzoimidazole;
5-(1-Hydroxy-2,2,2-trifluoro-ethyl)-1-(2'-methyl-biphenyl-3-yl)-1H-benzoimidazole;
5-(5-Isoxazolyl)-1-(2'-cyano-biphenyl-3-yl)-1H-benzoimidazole;
5-(5-isoxazolyl)-1-(5'-chloro-2'-methoxy-biphenyl-3-yl)-1H-benzoimidazole;
5-(5-Isoxazolyl)-1-(2'-acetyl-biphenyl-3-yl)-1H-benzoimidazole;
5-(1H-3-Pyrazolyl)-1-(2'-acetyl-biphenyl-3-yl)-1H-benzoimidazole;
5-(1H-3-Pyrazolyl)-1-(2'-methoxy-biphenyl-3-yl)-1H-benzoimidazole;
5-(1H-3-Pyrazolyl)-1-(2'-cyano-biphenyl-3-yl)-1H-benzoimidazole,
1-[3-(2-Fluoro-pyridin-3-yl)-phenyl]-5-trifluoromethyl-1H-benzoimidazole;
1-[3-(2-Methoxy-pyridin-3-yl)-phenyl]-5-trifluoromethyl-1H-benzoimidazole;
1-[3-(2,4-dimethoxy-pyrimidin-5-yl)-phenyl]-5-trifluoromethyl-1H-benzoimidazole;
1-[3-(2-Chloro-pyridin-3-yl)-phenyl]-5-trifluoromethyl-1H-benzoimidazole;
5-(5-Isoxazolyl)-1-(2'-carbamoyl-biphenyl-3-yl)-1H-benzoimidazole;
5-Formyl-1-(2'-methoxy-biphenyl-3-yl)-1H-benzoimidazole;

1-(2'-Methoxy-biphenyl-3-yl)-5-(2,2,2-trifluoro-1,1-dihydroxy-ethyl)-1H-benzoimidazole;
1-(2'-Methyl-biphenyl-3-yl)-5-(2,2,2-trifluoro-1,1-dihydroxy-ethyl)-1H-benzoimidazole;
5-Acetyl-1-(3-(benzo[1,3]-dioxol-4-yl)phenyl)-1H-benzoimidazole;
5-Fluoro-3'-(5-trifluoromethyl-benzoimidazol-1-yl)-biphenyl-2-ol;
(R)-1-[1-(2'-Methoxy-biphenyl-3-yl)-1H-benzoimidazol-5-yl]-ethanol;
3'-[5-((R)-1-Hydroxy-ethyl)-benzoimidazol-1-yl]-biphenyl-2-carboxylic acid amide;
(R)-1-[1-(5'-Chloro-2'-methoxy-biphenyl-3-yl)-1H-benzoimidazol-5-yl]-ethanol;
N-{3'-[5-((R)-1-Hydroxy-ethyl)-benzoimidazol-1-yl]-biphenyl-2-yl}-methanesulfonamide;
1-(2'-Methoxy-biphenyl-3-yl)-1H-benzoimidazole-5-carboxylic acid amide;
3'-[5-(1-Hydroxy-1-methyl-ethyl)-benzoimidazol-1-yl]-biphenyl-2-carbonitrile;
2-[1-(2'-Methoxy-biphenyl-3-yl)-1H-benzoimidazol-5-yl]-propan-2-ol;
(S)-1-[1-(5'-Chloro-2'-methoxy-biphenyl-3-yl)-1H-benzoimidazol-5-yl]-ethanol;
N-{3'-[5-((S)-1-Hydroxy-ethyl)-benzoimidazol-1-yl]-biphenyl-2-yl}-methanesulfonamide;
(S)-1-[1-(2'-Methoxy-biphenyl-3-yl)-1H-benzoimidazol-5-yl]-ethanol;
3'-[5-((S)-1-Hydroxy-ethyl)-benzoimidazol-1-yl]-biphenyl-2-carboxylic acid amide;
2-[1-(5'-Chloro-2'-methoxy-biphenyl-3-yl)-1H-benzoimidazol-5-yl]-propan-2-ol;
1-(5'-Fluoro-2'-methoxy-biphenyl-3-yl)-1H-benzoimidazole-5-carboxylic acid amide;
1-(5'-Chloro-2'-methoxy-biphenyl-3-yl)-1H-benzoimidazole-5-carboxylic acid amide;
(R)-1-[1-(2',6'-Dimethoxy-biphenyl-3-yl)-1H-benzoimidazol-5-yl]-ethanol;
1-(2'-Fluoro-6'-methoxy-biphenyl-3-yl)-1H-benzoimidazole-5-carboxylic acid amide;
1-(6'-Chloro-2'-methoxy-biphenyl-3-yl)-1H-benzoimidazole-5-carboxylic acid amide;
2-[1-(3'-Fluoro-2'-methoxy-biphenyl-3-yl)-1H-benzoimidazol-5-yl]-propan-2-ol;
(R)-1-[1-(3'-Fluoro-2'-methoxy-biphenyl-3-yl)-1H-benzoimidazol-5-yl]-ethanol;
2-[1-(2',3'-Dimethoxy-biphenyl-3-yl)-1H-benzoimidazol-5-yl]-propan-2-ol;
(R)-1-[1-(6'-Fluoro-2'-methoxy-biphenyl-3-yl)-1H-benzoimidazol-5-yl]-ethanol;
(R)-1-[1-(2',3'-Dimethoxy-biphenyl-3-yl)-1H-benzoimidazol-5-yl]-ethanol;
(R)-1-[1-(2',4'-Dimethoxy-biphenyl-3-yl)-1H-benzoimidazol-5-yl]-ethanol;
3-Chloro-3'-[5-(1-hydroxy-1-methyl-ethyl)-benzoimidazol-1-yl]-biphenyl-2-ol;
2-[1-(2',6'-Dimethoxy-biphenyl-3-yl)-1H-benzoimidazol-5-yl]-propan-2-ol;
(R)-1-[1-(6'-Chloro-2'-methoxy-biphenyl-3-yl)-1H-benzoimidazol-5-yl]-ethanol;
2-[1-(2',4'-Dimethoxy-biphenyl-3-yl)-1H-benzoimidazol-5-yl]-propan-2-ol;
2-[1-(6'-Fluoro-2'-methoxy-biphenyl-3-yl)-1H-benzoimidazol-5-yl]-propan-2-ol;
(R)-1-{1-[3-(2-Fluoro-pyridin-3-yl)-phenyl]-1H-benzoimidazol-5-yl}-ethanol;
(S)-1-{1-[3-(2-Fluoro-pyridin-3-yl)-phenyl]-1H-benzoimidazol-5-yl}-ethanol;
2-{1-[3-(2-Fluoro-pyridin-3-yl)-phenyl]-1H-benzoimidazol-5-yl}-propan-2-ol;
1-(2',6'-Dimethoxy-biphenyl-3-yl)-1H-benzoimidazole-5-carbonitrile;
1-(3'-Fluoro-2'-methoxy-biphenyl-3-yl)-1H-benzoimidazole-5-carbonitrile;
1-(6'-Fluoro-2'-methoxy-biphenyl-3-yl)-1H-benzoimidazole-5-carbonitrile;
1-(6'-Chloro-2'-methoxy-biphenyl-3-yl)-1H-benzoimidazole-5-carbonitrile;
1-(2'-Chloro-6'-fluoro-3'-methyl-biphenyl-3-yl)-1H-benzoimidazole-5-carbonitrile;
1-(2'-Chloro-6'-fluoro-5'-methyl-biphenyl-3-yl)-1H-benzoimidazole-5-carbonitrile;
1-(2',4'-Dimethoxy-biphenyl-3-yl)-1H-benzoimidazole-5-carbonitrile;
1-(2',3'-Dimethoxy-biphenyl-3-yl)-1H-benzoimidazole-5-carbonitrile;
1-[3-(5-Bromo-2-fluoro-pyridin-3-yl)-phenyl]-1H-benzoimidazole-5-carbonitrile;
1-[3-(2-Bromo-5-fluoro-pyridin-4-yl)-phenyl]-1H-benzoimidazole-5-carbonitrile;
1-(2',6'-Difluoro-biphenyl-3-yl)-1H-benzoimidazole-5-carbonitrile;
1-(2',6'-Dichloro-biphenyl-3-yl)-1H-benzoimidazole-5-carbonitrile;
1-(2'-piperazin-1-yl-biphenyl-3-yl)-1H-benzoimidazole-5-carbonitrile;
1-[3-(2-Bromo-5-methoxy-pyridin-4-yl)-phenyl]-1H-benzoimidazole-5-carbonitrile;
1-[3-(2-Chloro-3-fluoro-pyridin-4-yl)-phenyl]-1H-benzoimidazole-5-carbonitrile;
1-(2',3'-Difluoro-6'-methoxy-biphenyl-3-yl)-1H-benzoimidazole-5-carbonitrile;
1-(4'-Fluoro-2'-methoxy-biphenyl-3-yl)-1H-benzoimidazole-5-carbonitrile;
1-(2'-Chloro-5'-cyano-biphenyl-3-yl)-1H-benzoimidazole-5-carbonitrile;
1-(3'-Chloro-2'-hydroxy-biphenyl-3-yl)-1H-benzoimidazole-5-carbonitrile;
1-(3'-Chloro-2',6'-difluoro-biphenyl-3-yl)-1H-benzoimidazole-5-carbonitrile;
1-[3-(2,4-Dimethoxy-pyrimidin-5-yl)-phenyl]-1H-benzoimidazole-5-carbonitrile;
1-[3-(2,6-Difluoro-pyridin-3-yl)-phenyl]-1H-benzoimidazole-5-carbonitrile;
1-[3-(3-Fluoro-pyridin-4-yl)-phenyl]-1H-benzoimidazole-5-carbonitrile;
1-[3-(3-Chloro-pyridin-4-yl)-phenyl]-1H-benzoimidazole-5-carbonitrile;
1-[3-(2-Chloro-pyridin-3-yl)-phenyl]-1H-benzoimidazole-5-carbonitrile;
1-(2'-Morpholin-4-ylmethyl-biphenyl-3-yl)-1H-benzoimidazole-5-carbonitrile;
1-{3-[2-(4-Methyl-piperazin-1-yl)-pyrimidin-5-yl]-phenyl}-1H-benzoimidazole-5-carbonitrile;
1-[3-(2-Morpholin-4-yl-pyrimidin-5-yl)-phenyl]-1H-benzoimidazole-5-carbonitrile;
1-{3-[5-(Morpholine-4-carbonyl)-pyridin-3-yl]-phenyl}-1H-benzoimidazole-5-carbonitrile;
1-(3',5'-Difluoro-2'-methoxy-biphenyl-3-yl)-1H-benzoimidazole-5-carbonitrile;
N-[3'-(5-Cyano-benzoimidazol-1-yl)-biphenyl-2-yl]-methanesulfonamide;

1-[3-(2-Fluoro-pyridin-3-yl)-phenyl]-1H-benzoimidazole-5-carbonitrile;
1-(5'-Chloro-2'-methoxy-biphenyl-3-yl)-1H-benzoimidazole-5-carbonitrile;
3'-(5-Cyano-benzoimidazol-1-yl)-biphenyl-2-carboxylic acid amide;
1-(2',6'-Dimethoxy-biphenyl-3-yl)-1H-benzoimidazole-5-carboxylic acid amide;
1-(3'-Fluoro-2'-methoxy-biphenyl-3-yl)-1H-benzoimidazole-5-carboxylic acid amide;
1-(2'-Chloro-6'-fluoro-3'-methyl-biphenyl-3-yl)-1H-benzoimidazole-5-carboxylic acid amide;
1-(6'-Chloro-2'-fluoro-3'-methyl-biphenyl-3-yl)-1H-benzoimidazole-5-carboxylic acid amide;
1-(2',4'-Dimethoxy-biphenyl-3-yl)-1H-benzoimidazole-5-carboxylic acid amide;
1-(2',3'-Dimethoxy-biphenyl-3-yl)-1H-benzoimidazole-5-carboxylic acid amide;
1-[3-(5-Bromo-2-fluoro-pyridin-3-yl)-phenyl]-1H-benzoimidazole-5-carboxylic acid amide;
1-[3-(2-Bromo-5-fluoro-pyridin-4-yl)-phenyl]-1H-benzoimidazole-5-carboxylic acid amide;
1-(2',6'-Difluoro-biphenyl-3-yl)-1H-benzoimidazole-5-carboxylic acid amide;
1-(2',6'-Dichloro-biphenyl-3-yl)-1H-benzoimidazole-5-carboxylic acid amide;
1-(2'-piperazin-1-yl-biphenyl-3-yl)-1H-benzoimidazole-5-carboxylic acid amide;
1-[3-(2-Bromo-5-methoxy-pyridin-4-yl)-phenyl]-1H-benzoimidazole-5-carboxylic acid amide;
1-[3-(2-Chloro-3-fluoro-pyridin-4-yl)-phenyl]-1H-benzoimidazole-5-carboxylic acid amide;
1-(2',3'-Difluoro-6'-methoxy-biphenyl-3-yl)-1H-benzoimidazole-5-carboxylic acid amide;
1-(4'-Fluoro-2'-methoxy-biphenyl-3-yl)-1H-benzoimidazole-5-carboxylic acid amide;
1-(2'-Chloro-5'-cyano-biphenyl-3-yl)-1H-benzoimidazole-5-carboxylic acid amide;
1-(3'-Chloro-2'-hydroxy-biphenyl-3-yl)-1H-benzoimidazole-5-carboxylic acid amide;
1-(3'-Chloro-2',6'-difluoro-biphenyl-3-yl)-1H-benzoimidazole-5-carboxylic acid amide;
1-[3-(2,4-Dimethoxy-pyrimidin-5-yl)-phenyl]-1H-benzoimidazole-5-carboxylic acid amide;
1-[3-(2,6-Difluoro-pyridin-3-yl)-phenyl]-1H-benzoimidazole-5-carboxylic acid amide;
1-[3-(3-Fluoro-pyridin-4-yl)-phenyl]-1H-benzoimidazole-5-carboxylic acid amide;
1-[3-(3-Chloro-pyridin-4-yl)-phenyl]-1H-benzoimidazole-5-carboxylic acid amide;
1-[3-(2-Chloro-pyridin-3-yl)-phenyl]-1H-benzoimidazole-5-carboxylic acid amide;
1-(2'-Morpholin-4-ylmethyl-biphenyl-3-yl)-1H-benzoimidazole-5-carboxylic acid amide;
1-(2'-Morpholin-4-ylmethyl-biphenyl-3-yl)-1H-benzoimidazole-5-carboxylic acid amide;
1-[3-(2-Morpholin-4-yl-pyrimidin-5-yl)-phenyl]-1H-benzoimidazole-5-carboxylic acid amide;
1-{3-[3-(Morpholine-4-carbonyl)-pyridin-4-yl]-phenyl}-1H-benzoimidazole-5-carboxylic acid amide;
1-(3',5'-Difluoro-2'-methoxy-biphenyl-3-yl)-1H-benzoimidazole-5-carboxylic acid amide;
1-(2'-Methanesulfonylamino-biphenyl-3-yl)-1H-benzoimidazole-5-carboxylic acid amide;
1-[3-(2-Fluoro-pyridin-3-yl)-phenyl]-1H-benzoimidazole-5-carboxylic acid amide;
1-(2'-Carbamoyl-biphenyl-3-yl)-1H-benzoimidazole-5-carboxylic acid amide;
(R)-1-[1-(2'-Chloro-6'-fluoro-3'-methyl-biphenyl-3-yl)-1H-benzoimidazol-5-yl]-ethanol;
(R)-1-[1-(6'-Chloro-2'-fluoro-3'-methyl-biphenyl-3-yl)-1H-benzoimidazol-5-yl]-ethanol;
(R)-1-{1-[3-(5-Bromo-2-fluoro-pyridin-3-yl)-phenyl]-1H-benzoimidazol-5-yl}-ethanol;
(R)-1-{1-[3-(2-Bromo-5-fluoro-pyridin-4-yl)-phenyl]-1H-benzoimidazol-5-yl}-ethanol;
(R)-1-[1-(2',6'-Difluoro-biphenyl-3-yl)-1H-benzoimidazol-5-yl]-ethanol;
(R)-1-[1-(2',6'-Dichloro-biphenyl-3-yl)-1H-benzoimidazol-5-yl]-ethanol;
1-[1-((R)-2'-piperazin-1-yl-biphenyl-3-yl)-1H-benzoimidazol-5-yl]-ethanol;
(R)-1-{1-[3-(2-Bromo-5-methoxy-pyridin-4-yl)-phenyl]-1H-benzoimidazol-5-yl}-ethanol;
(R)-1-{1-[3-(2-Chloro-3-fluoro-pyridin-4-yl)-phenyl]-1H-benzoimidazol-5-yl}-ethanol;
(R)-1-[1-(2',3'-Difluoro-6'-methoxy-biphenyl-3-yl)-1H-benzoimidazol-5-yl]-ethanol;
(R)-1-[1-(4'-Fluoro-2'-methoxy-biphenyl-3-yl)-1H-benzoimidazol-5-yl]-ethanol;
6-Chloro-3'-[5-((R)-1-hydroxy-ethyl)-benzoimidazol-1-yl]-biphenyl-3-carbonitrile;
3-Chloro-3'-[5-((R)-1-hydroxy-ethyl)-benzoimidazol-1-yl]-biphenyl-2-ol;
(R)-1-[1-(3'-Chloro-2',6'-difluoro-biphenyl-3-yl)-1H-benzoimidazol-5-yl]-ethanol;
(R)-1-{1-[3-(2,4-Dimethoxy-pyrimidin-5-yl)-phenyl]-1H-benzoimidazol-5-yl}-ethanol;
(R)-1-{1-[3-(2,6-Difluoro-pyridin-3-yl)-phenyl]-1H-benzoimidazol-5-yl}-ethanol;
(R)-1-{1-[3-(3-Fluoro-pyridin-4-yl)-phenyl]-1H-benzoimidazol-5-yl}-ethanol;
(R)-1-{1-[3-(3-Chloro-pyridin-4-yl)-phenyl]-1H-benzoimidazol-5-yl}-ethanol;
(R)-1-{1-[3-(2-Chloro-pyridin-3-yl)-phenyl]-1H-benzoimidazol-5-yl}-ethanol;
(R)-1-[1-(2'-Morpholin-4-ylmethyl-biphenyl-3-yl)-1H-benzoimidazol-5-yl]-ethanol;
(R)-1-(1-{3-[2-(4-Methyl-piperazin-1-yl)-pyrimidin-5-yl]-phenyl}-1H-benzoimidazol-5-yl)-ethanol;
(R)-1-{1-[3-(2-Morpholin-4-yl-pyrimidin-5-yl)-phenyl]-1H-benzoimidazol-5-yl}-ethanol;
(5-{3-[5-((R)-1-Hydroxy-ethyl)-benzoimidazol-1-yl]-phenyl}-pyridin-3-yl)-morpholin-4-yl-methanone;
(R)-1-[1-(3',5'-Difluoro-2'-methoxy-biphenyl-3-yl)-1H-benzoimidazol-5-yl]-ethanol;
(S)-1-[1-(2',6'-Dimethoxy-biphenyl-3-yl)-1H-benzoimidazol-5-yl]-ethanol;
(S)-1-[1-(3'-Fluoro-2'-methoxy-biphenyl-3-yl)-1H-benzoimidazol-5-yl]-ethanol;
(S)-1-[1-(6'-Fluoro-2-methoxy-biphenyl-3-yl)-1H-benzoimidazol-5-yl]-ethanol;
(S)-1-[1-(2',3'-Dimethoxy-biphenyl-3-yl)-1H-benzoimidazol-5-yl]-ethanol;
(S)-1-[1-(2',4'-Dimethoxy-biphenyl-3-yl)-1H-benzoimidazol-5-yl]-ethanol;
(S-1-[1-(6'-Chloro-2'-methoxy-biphenyl-3-yl)-1H-benzoimidazol-5-yl]-ethanol;
(S)-1-[1-(2'-Chloro-6'-fluoro-3'-methyl-biphenyl-3-yl)-1H-benzoimidazol-5-yl]-ethanol;
(S)-1-[1-(6'-Chloro-2'-fluoro-3'-methyl-biphenyl-3-yl)-1H-benzoimidazol-5-yl]-ethanol;

(S)-1-{1-[3-(5-Bromo-2-fluoro-pyridin-3-yl)-phenyl]-1H-benzoimidazol-5-yl}-ethanol;
(S)-1-{1-[3-(2-Bromo-5-fluoro-pyridin-4-yl)-phenyl]-1H-benzoimidazol-5-yl}-ethanol;
(S)-1-[1-(2',6'-Difluoro-biphenyl-3-yl)-1H-benzoimidazol-5-yl]-ethanol;
(S)-1-[1-(2',6'-Dichloro-biphenyl-3-yl)-1H-benzoimidazol-5-yl]-ethanol;
1-[1-((S)-2'-piperazin-1-yl-biphenyl-3-yl)-1H-benzoimidazol-5-yl]-ethanol;
(S)-1-{1-[3-(2-Bromo-5-methoxy-pyridin-4-yl)-phenyl]-1H-benzoimidazol-5-yl}-ethanol;
(S)-1-{1-[3-(2-Chloro-3-fluoro-pyridin-4-yl)-phenyl]-1H-benzoimidazol-5-yl}-ethanol;
(S)-1-[1-(2',3'-Difluoro-6'-methoxy-biphenyl-3-yl)-1H-benzoimidazol-5-yl]-ethanol;
(S)-1-[1-(4'-Fluoro-2'-methoxy-biphenyl-3-yl)-1H-benzoimidazol-5-yl]-ethanol;
6-Chloro-3'-[5-((S)-1-hydroxy-ethyl)-benzoimidazol-1-yl]-biphenyl-3-carbonitrile;
3-Chloro-3'-[5-((S)-1-hydroxy-ethyl)-benzoimidazol-1-yl]-biphenyl-2-ol;
(S)-1-[1-(3'-Chloro-2',6'-difluoro-biphenyl-3-yl)-1H-benzoimidazol-5-yl]-ethanol;
(S)-1-{1-[3-(2,4-Dimethoxy-pyrimidin-5-yl)-phenyl]-1H-benzoimidazol-5-yl}-ethanol;
(S)-1-{1-[3-(2,6-Difluoro-pyridin-3-yl)-phenyl]-1H-benzoimidazol-5-yl}-ethanol;
(S)-1-{1-[3-(3-Fluoro-pyridin-4-yl)-phenyl]-1H-benzoimidazol-5-yl}-ethanol;
(S)-1-{1-[3-(3-Chloro-pyridin-4-yl)-phenyl]-1H-benzoimidazol-5-yl}-ethanol;
(S)-1-{1-[3-(2-Chloro-pyridin-3-yl)-phenyl]-1H-benzoimidazol-5-yl}-ethanol;
(S)-1-[1-(2'-Morpholin-4-ylmethyl-biphenyl-3-yl)-1H-benzoimidazol-5-yl]-ethanol;
(S)-1-(1-{3-[2-(4-Methyl-piperazin-1-yl)-pyrimidin-5-yl]-phenyl}-1H-benzoimidazol-5-yl)-ethanol;
(S)-1-{1-[3-(2-Morpholin-4-yl-pyrimidin-5-yl)-phenyl]-1H-benzoimidazol-5-yl}-ethanol;
(5-{3-[5-((S)-1-Hydroxy-ethyl)-benzoimidazol-1-yl]-phenyl}-pyridin-3-yl)-morpholin-4-yl-methanone;
(S)-1-[1-(3',5'-Difluoro-2'-methoxy-biphenyl-3-yl)-1H-benzoimidazol-5-yl]-ethanol;
2-[1-(6'-Chloro-2'-methoxy-biphenyl-3-yl)-1H-benzoimidazol-5-yl]-propan-2-ol;
2-[1-(2'-Chloro-6'-fluoro-3'-methyl-biphenyl-3-yl)-1H-benzoimidazol-5-yl]-propan-2-ol;
2-[1-(6'-Chloro-2'-fluoro-3'-methyl-biphenyl-3-yl)-1H-benzoimidazol-5-yl]-propan-2-ol;
2-{1-[3-(5-Bromo-2-fluoro-pyridin-3-yl)-phenyl]-1H-benzoimidazol-5-yl}-propan-2-ol;
2-{1-[3-(2-Bromo-5-fluoro-pyridin-4-yl)-phenyl]-1H-benzoimidazol-5-yl}-propan-2-ol;
2-[1-(2',6'-Difluoro-biphenyl-3-yl)-1H-benzoimidazol-5-yl]-propan-2-ol;
2-[1-(2',6'-Dichloro-biphenyl-3-yl)-1H-benzoimidazol-5-yl]-propan-2-ol;
2-[1-(2'-piperazin-1-yl-biphenyl-3-yl)-1H-benzoimidazol-5-yl]-propan-2-ol;
2-{1-[3-(2-Bromo-5-methoxy-pyridin-4-yl)-phenyl]-1H-benzoimidazol-5-yl}-propan-2-ol;
2-{1-[3-(2-Chloro-3-fluoro-pyridin-4-yl)-phenyl]-1H-benzoimidazol-5-yl}-propan-2-ol;
2-[1-(2',3'-Difluoro-6'-methoxy-biphenyl-3-yl)-1H-benzoimidazol-5-yl]-propan-2-ol;
2-[1-(4'-Fluoro-2'-methoxybiphenyl-3-yl)-1H-benzoimidazol-5-yl]-propan-2-ol;
6-Chloro-3'-[5-(1-hydroxy-1-methyl-ethyl)-benzoimidazol-1-yl]-biphenyl-3-carbonitrile;
2-[1-(3'-Chloro-2',6'-difluoro-biphenyl-3-yl)-1H-benzoimidazol-5-yl]-propan-2-ol;
2-{1-[3-(2,4-Dimethoxy-pyrimidin-5-yl)-phenyl]-1H-benzoimidazol-5-yl}-propan-2-ol;
2-{1-[3-(2,6-Difluoro-pyridin-3-yl)-phenyl]-1H-benzoimidazol-5-yl}-propan-2-ol;
2-{1-[3-(3-Fluoro-pyridin-4-yl)-phenyl]-1H-benzoimidazol-5-yl}-propan-2-ol;
2-{1-[3-(3-Chloro-pyridin-4-yl)-phenyl]-1H-benzoimidazol-5-yl}-propan-2-ol;
2-{1-[3-(2-Chloro-pyridin-3-yl)-phenyl]-1H-benzoimidazol-5-yl}-propan-2-ol;
2-[1-(2'-Morpholin-4-ylmethyl-biphenyl-3-yl)-1H-benzoimidazol-5-yl]-propan-2-ol;
2-(1-{3-[2-(4-Methyl-piperazin-1-yl)-pyrimidin-5-yl]-phenyl}-1H-benzoimidazol-5-yl)-propan-2-ol;
2-{1-[3-(2-Morpholin-4-yl-pyrimidin-5-yl)-phenyl]-1H-benzoimidazol-5-yl}-propan-2-ol;
(5-{3-[5-(1-Hydroxy-1-methyl-ethyl)-benzoimidazol-1-yl]-phenyl}-pyridin-3-yl)-morpholin-4-yl-methanone;
2-[1-(3',5'-Difluoro-2'-methoxy-biphenyl-3-yl)-1H-benzoimidazol-5-yl]-propan-2-ol;
3'-[5-(1-Hydroxy-1-methyl-ethyl)-benzoimidazol-1-yl]-biphenyl-2-carboxylic acid amide;
N-{3'-[5-(1-Hydroxy-1-methyl-ethyl)-benzoimidazol-1-yl]-biphenyl-2-yl}-methanesulfonamide;
2-[1-(5'-Fluoro-2'-methoxy-biphenyl-3-yl)-1H-benzoimidazol-5-yl]-propan-2-ol;
1-[1-(5'-Chloro-2'-methoxy-biphenyl-3-yl)-1H-benzoimidazol-5-yl]-ethanone;
1-(2'-Ethyl-biphenyl-3-yl)-1H-benzoimidazole-5-carbaldehyde oxime;
1-(2'-Methyl-biphenyl-3-yl)-1H-benzoimidazole-5-carbaldehyde oxime;
1-(2'-Ethoxy-biphenyl-3-yl)-1H-benzoimidazole-5-carbaldehyde oxime;
1-(2'-Methyl-biphenyl-3-yl)-1H-benzoimidazole-5-carbaldehyde O-methyl-oxime;
1-(2'-Ethoxy-biphenyl-3-yl)-1H-benzoimidazole-5-carbaldehyde O-methyl-oxime;
1-(2'-Isopropoxy-biphenyl-3-yl)-1H-benzoimidazole-5-carbaldehyde O-methyl-oxime;
1-(2'-Isopropoxy-biphenyl-3-yl)-1H-benzoimidazole-5-carbaldehyde oxime;
1-(2'-Methoxy-biphenyl-3-yl)-1H-benzoimidazole-5-carbaldehyde O-methyl-oxime;
1-(2'-Methoxy-biphenyl-3-yl)-1H-benzoimidazole-5-carbaldehyde oxime;
1-(2'-Cyano-biphenyl-3-yl)-1H-benzoimidazole-5-carbaldehyde O-methyl-oxime;
1-(2'-Cyano-biphenyl-3-yl)-1H-benzoimidazole-5-carbaldehyde oxime;
1-[3'-(5-Trifluoromethyl-benzoimidazol-1-yl)-biphenyl-2-yl]-ethanone oxime;
1-[3'-(5-Trifluoromethyl-benzoimidazol-1-yl)-biphenyl-2-yl]-ethanone O-methyl-oxime;
1-(2'-Cyano-biphenyl-3-yl)-1H-benzoimidazole-5-acetyl O-methyl-oxime;
1-(2'-Cyano-biphenyl-3-yl)-1H-benzoimidazole-5-acetyl oxime);
5-Trifluoromethyl-1-(2'-(1-hydroxyethyl)-biphenyl-3-yl)-1H-benzoimidazole;

5-(1H-3-Pyrazolyl)-1-(2'-(1-hydroxyethyl)-biphenyl-3-yl)-1H-benzoimidazole;
5-Trifluoromethyl-1-(2'-(1-ethoxyethyl)-biphenyl-3-yl)-1H-benzoimidazole;
5-Trifluoromethyl-1-(2'-(5-isoxazolyl)-biphenyl-3-yl)-1H-benzoimidazole;
5-(1H-3-Pyrazolyl)-1-(2'-(5-isoxazolyl)-biphenyl-3-yl)-1H-benzoimidazole;
5-Trifluoromethyl-1-(2'-(1H-3-pyrazolyl)-biphenyl-3-yl)-1H-benzoimidazole;
5-(1H-3-Pyrazolyl)-1-(2'-(1H-3-pyrazolyl)-biphenyl-3-yl)-1H-benzoimidazole;
5-(N-Hydroxy-carboxamidinyl)-1-(2'-methoxy-biphenyl-3-yl)-1H-benzoimidazole;
5-(4,5-Dihydro-1H-imidazol-2-yl)-1-(2'-methoxy-biphenyl-3-yl)-1H-benzoimidazole;
5-(Cyano-hydroxy-methyl)-1-(2'-methoxy-biphenyl-3-yl)-1H-benzoimidazole;
5-(1-Hydroxy-prop-2-ynyl)-1-(2'-methoxy-biphenyl-3-yl)-1H-benzoimidazole;
5-(N-Hydroxy-carboxamidinyl)-1-(2'-methoxy-biphenyl-3-yl)-1H-benzoimidazole;
1-(2'-Chloro-biphenyl-3-yl)-N-hydroxy-1H-benzoimidazole-5-carboxamidine 12ha;
N-Hydroxy-1-(2'-isopropoxy-biphenyl-3-yl)-1H-benzoimidazole-5-carboxamidine;
1-(2'-Ethoxy-biphenyl-3-yl)-N-hydroxy-1H-benzoimidazole-5-carboxamidine;
N-Hydroxy-1-(2'-methyl-biphenyl-3-yl)-1H-benzoimidazole-5-carboxamidine;
1-(2'-Ethyl-biphenyl-3-yl)-N-hydroxy-1H-benzoimidazole-5-carboxamidine;
1-(5'-Fluoro-2'-methoxy-biphenyl-3-yl)-N-hydroxy-1H-benzoimidazole-5-carboxamidine;
1-(2',6'-Dimethoxy-biphenyl-3-yl)-N-hydroxy-1H-benzoimidazole-5-carboxamidine;
1-(3'-Fluoro-2'-methoxy-biphenyl-3-yl)-N-hydroxy-1H-benzoimidazole-5-carboxamidine;
1-(2'-Fluoro-6'-methoxy-biphenyl-3-yl)-N-hydroxy-1H-benzoimidazole-5-carboxamidine;
1-(2'-Chloro-6'-methoxy-biphenyl-3-yl)-N-hydroxy-1H-benzoimidazole-5-carboxamidine;
1-(2'-Chloro-6'-fluoro-3'-methyl-biphenyl-3-yl)-N-hydroxy-1H-benzoimidazole-5-carboxamidine;
1-(6'-Chloro-2'-fluoro-3'-methyl-biphenyl-3-yl)-N-hydroxy-1H-benzoimidazole-5-carboxamidine;
1-(2',4'-Dimethoxy-biphenyl-3-yl)-N-hydroxy-1H-benzoimidazole-5-carboxamidine;
1-(2',3'-Dimethoxy-biphenyl-3-yl)-N-hydroxy-1H-benzoimidazole-5-carboxamidine;
1-[3-(5-Bromo-2-fluoro-pyridin-3-yl)-phenyl]-N-hydroxy-1H-benzoimidazole-5-carboxamidine;
1-[3-(2-Bromo-5-fluoro-pyridin-4-yl)-phenyl]-N-hydroxy-1H-benzoimidazole-5-carboxamidine;
1-(2',6'-Difluoro-biphenyl-3-yl)-N-hydroxy-1H-benzoimidazole-5-carboxamidine;
1-(2',6'-Dichloro-biphenyl-3-yl)-N-hydroxy-1H-benzoimidazole-5-carboxamidine;
N-Hydroxy-1-(2'-piperazin-1-yl-biphenyl-3-yl)-1H-benzoimidazole-5-carboxamidine;
1-[3-(2-Bromo-5-methoxy-pyridin-4-yl)-phenyl]-N-hydroxy-1H-benzoimidazole-5-carboxamidine;
1-[3-(2-Chloro-3-fluoro-pyridin-4-yl)-phenyl]-N-hydroxy-1H-benzoimidazole-5-carboxamidine;
1-(2',3'-Difluoro-6'-methoxy-biphenyl-3-yl)-N-hydroxy-1H-benzoimidazole-5-carboxamidine;
1-(4'-Fluoro-2'-methoxy-biphenyl-3-yl)-N-hydroxy-1H-benzoimidazole-5-carboxamidine;
1-(3'-Chloro-2'-hydroxy-biphenyl-3-yl)-N-hydroxy-1H-benzoimidazole-5-carboxamidine;
1-(3'-Chloro-2',6'-difluoro-biphenyl-3-yl)-N-hydroxy-1H-benzoimidazole-5-carboxamidine;
1-[3-(2,4-Dimethoxy-pyrimidin-5-yl)-phenyl]-N-hydroxy-1H-benzoimidazole-5-carboxamidine;
1-[3-(2,6-Difluoro-pyridin-3-yl)-phenyl]-N-hydroxy-1H-benzoimidazole-5-carboxamidine;
1-[3-(3-Fluoro-pyridin-4-yl)-phenyl]-N-hydroxy-1H-benzoimidazole-5-carboxamidine;
1-[3-(3-Chloro-pyridin-4-yl)-phenyl]-N-hydroxy-1H-benzoimidazole-5-carboxamidine;
1-[3-(2-Chloro-pyridin-3-yl)-phenyl]-N-hydroxy-1H-benzoimidazole-5-carboxamidine;
N-Hydroxy-1-(2'-morpholin-4-ylmethyl-biphenyl-3-yl)-1H-benzoimidazole-5-carboxamidine;
N-Hydroxy-1-{3-[2-(4-methyl-piperazin-1-yl)-pyrimidin-5-yl]-phenyl}-1H-benzoimidazole-5-carboxamidine;
N-Hydroxy-1-[3-(2-morpholin-4-yl-pyrimidin-5-yl)-phenyl]-1H-benzoimidazole-5-carboxamidine;
N-Hydroxy-1-{3-[5-(morpholine-4-carbonyl)-pyridin-3-yl]-phenyl}-1H-benzoimidazole-5-carboxamidine;
1-(3',5'-Difluoro-2'-methoxy-biphenyl-3-yl)-N-hydroxy-1H-benzoimidazole-5-carboxamidine;
N-Hydroxy-1-(2'-methanesulfonylamino-biphenyl-3-yl)-1H-benzoimidazole-5-carboxamidine;
1-[3-(2-Fluoro-pyridin-3-yl)-phenyl]-N-hydroxy-1H-benzoimidazole-5-carboxamidine;
1-(5'-Chloro-2'-methoxy-biphenyl-3-yl)-N-hydroxy-1H-benzoimidazole-5-carboxamidine;
3'-[5-(N-Hydroxycarbamimidoyl)-benzoimidazol-1-yl]-biphenyl-2-carboxylic acid amide;
3'-(5-Oxazol-5-yl-benzoimidazol-1-yl)-biphenyl-2-carbonitrile;
1-(2'-Methoxy-biphenyl-3-yl)-5-oxazol-5-yl-1H-benzoimidazole;
1-(2'-Isopropoxy-biphenyl-3-yl)-5-oxazol-5-yl-1H-benzoimidazole;
1-(2'-Ethoxy-biphenyl-3-yl)-5-oxazol-5-yl-1H-benzoimidazole;
1-(2'-Methyl-biphenyl-3-yl)-5-oxazol-5-yl-1H-benzoimidazole;
1-(2'-Ethyl-biphenyl-3-yl)-5-oxazol-5-yl-1H-benzoimidazole;
4-[1-(5'-Chloro-2'-methoxy-biphenyl-3-yl)-1H-benzoimidazol-5-yl]-pyrimidin-2-ylamine;
1-{1-[3-(2-Hydroxy-pyridin-3-yl)-phenyl]-1H-benzoimidazol-5-yl}-ethanone oxime;
3-{3-[5-(1-Hydroxy-ethyl)-benzoimidazol-1-yl]-phenyl}-pyridin-2-ol
1-[1-(3-Benzo[1,3]dioxol-4-yl-phenyl)-1H-benzoimidazol-5-yl]-ethanol;
1-(3-Benzo[1,3]dioxol-4-yl-phenyl)-5-(1-ethoxy-ethyl)-1H-benzoimidazole;
1-[3-(2-Chloro-pyridin-3-yl)-phenyl]-1H-benzoimidazole-5-carboxylic acid isopropyl ester;
or an N-oxide thereof, any of its isomers or any mixture of its isomers,
or a pharmaceutically acceptable salt thereof.

Any combination of two or more of the embodiments as described above is considered within the scope of the present invention.

DEFINITION OF SUBSTITUENTS

In the context of this invention halo represents fluoro, chloro, bromo or iodo.

In the context of this invention an alkyl group designates a univalent saturated, straight or branched hydrocarbon chain. The hydrocarbon chain preferably contain of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butadienyl; 1-, 2-, 3-, 4- or 5-hexenyl, or 1,3-hexadienyl, or 1,3,5-hexatrienyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-henynyl, or 1,3-hexadiynyl or 1,3,5-hexatriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

Alkoxy means O-alkyl, wherein alkyl is as defined above.

Alkoxyalkyl means alkoxy as above and alkyl as above, meaning for example, methoxymethyl.

Cycloalkoxy means O-cycloalkyl, wherein cycloalkyl is as defined above.

Cycloalkylalkyl means cycloalkyl as above and alkyl as above, meaning for example, cyclopropylmethyl.

In the context of this invention, a carbonyl group (—C(=O)—) is also intended to include a hydrated carbonyl group (—C(OH)$_2$—).

In the context of this invention a heterocyclic ring designates a monocyclic heterocyclic group, which holds one or more heteroatoms in its ring. Preferred heteroatoms include nitrogen (N), oxygen (O), and sulphur (S). The ring may in particular be aromatic (i.e. a heteroaryl), saturated or partially saturated.

Examples of preferred saturated or partially saturated monocyclic heterocyclic 5-membered groups of the invention include 1,3-dioxolan, imidazoline, imidazolidine, oxazoline, oxazolidine, oxadiazoline, pyrroline, pyrrolidine, pyrazolidine, and pyrazoline.

Examples of preferred saturated or partially saturated monocyclic heterocyclic 6-membered groups of the invention include 1,4-dioxolane, 1,4-dithiane, morpholine, 1,4-oxazine, oxadiazine, piperidine, piperazine, dihydro-pyrane, tetrahydro-pyrane, thiomorpholine, 1,3,5-trithiane.

Examples of preferred saturated or partially saturated monocyclic heterocyclic 7-membered groups of the invention include homopiperidine and homopiperazine.

Examples of preferred monocyclic heteroaryl groups of the invention include aromatic 5- and 6-membered monocyclic heterocyclic groups, including for example, but not limited to, oxazolyl, isoxazolyl, thiazolyl, isothiazolyl, tetrazolyl, 1,2,4-oxadiazolyl, 1,2,5-oxadiazolyl, 1,3,4-oxadiazolyl, triazolyl, 1,2,4-thiadiazolyl, 1,2,5-thiadiazolyl, imidazolyl, pyrrolyl, pyrazolyl, furanyl, thienyl, pyridyl, pyrimidyl, or pyridazinyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydro-chloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention including compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may contain one or more chiral centres and that such compounds may exist in different stereoisomeric forms—including enantiomers, diastereomers and cis-trans-isomers.

The invention includes all such isomers and any mixtures thereof including racemic mixtures.

Methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

N-oxides

In the context of this invention an N-oxide designates an oxide derivative of a nitrogen containing compound, e.g. N-containing heterocyclic compounds capable of forming such N-oxides, and compounds holding one or more amino groups. For example, the N-oxide of a compound containing a pyridyl may be the 1-oxy-pyridin-2, -3 or -4-yl derivative.

N-oxides of the compounds of the invention may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from 2H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Biological Activity

Compounds of the invention are capable of modulating the $GABA_A$ receptor complex. They may be tested for their ability to bind to the $GABA_A$ receptor complex, including specific subunits thereof.

The compounds of the present invention, being ligands for the benzodiazepine binding site on $GABA_A$ receptors, are therefore of use in the treatment and/or prevention of a variety of disorders of and outside the central nervous system. Thus in further aspect, the compounds of the invention are considered useful for the treatment, prevention or alleviation of a disease, disorder or condition responsive to modulation of the $GABA_A$ receptor complex, in particular in the central nervous system. In a further embodiment, the compounds of the invention are ligands of the $GABA_A$ receptor complex outside the central nervous system.

In a special embodiment, the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

stress disorders including post-traumatic and acute stress disorder;

sleep disorders;

memory disorder;

neuroses;

convulsive disorders, for example epilepsy, seizures, convulsions, or febrile convulsions in children;

migraine;

mood disorders;

depressive or bipolar disorders, for example depression, single-episode or recurrent major depressive disorder, dysthymic disorder, bipolar disorder, bipolar I and bipolar II manic disorders, and cyclothymic disorder, psychotic disorders, including schizophrenia;

neurodegeneration arising from cerebral ischemia;

attention deficit hyperactivity disorder;

pain and nociception, e.g. neuropathic pain;

emesis, including acute, delayed and anticipatory emesis, in particular emesis induced by chemotherapy or radiation;

motion sickness, post-operative nausea and vomiting;

eating disorders including anorexia nervosa and bulimia nervosa;

premenstrual syndrome;

neuralgia, e.g. trigeminal neuralgia;

muscle spasm or spasticity, e.g. in paraplegic patients;

the effects of substance abuse or dependency, including alcohol withdrawal;

cognitive disorders, such as Alzheimer's disease;

cerebral ischemia, stroke, head trauma;

tinnitus;

disorders of circadian rhythm, e.g. in subjects suffering from the effects of jet lag or shift work;

diabetes, type 1 diabetes (insulin-dependent diabetes mellitus), type 2 diabetes, hyperinsulinemia; and other inflammatory diseases and auto immune disorders.

Preferably the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

Further, the compounds of the invention may be useful as radioligands in assays for detecting compounds capable of binding to the human $GABA_A$ receptor.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of the $GABA_A$ receptor complex, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

General

All reactions involving air sensitive reagents or intermediates were performed under nitrogen and in anhydrous solvents. Magnesium sulphate or sodium sulphate was used as drying agent in the workup-procedures and solvents were evaporated under reduced pressure

Example 1
Synthesis of Key Intermediates
The following twelve compounds were used as starting materials throughout the examples. Compounds 1, 2 and 3 are described in prior art (EP 563001, WO 96/33194 and WO 96/33191; all NeuroSearch A/S), whereas the syntheses of compounds 4-12 are described below.
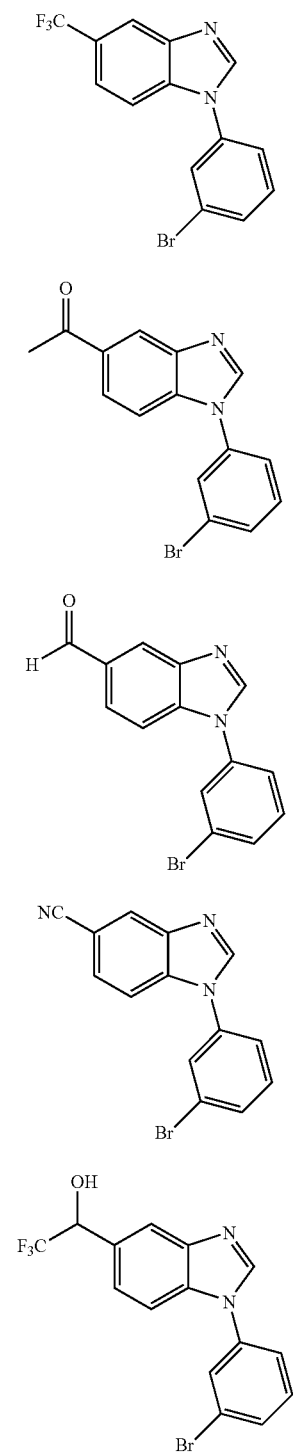
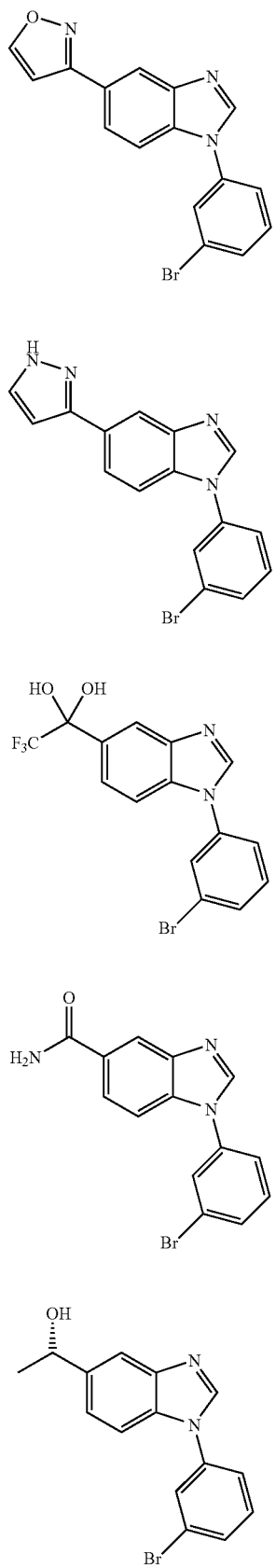

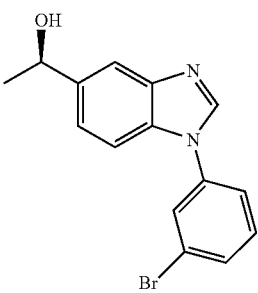

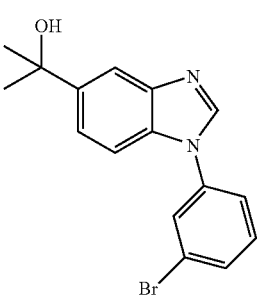

Synthesis of Key Intermediate 4

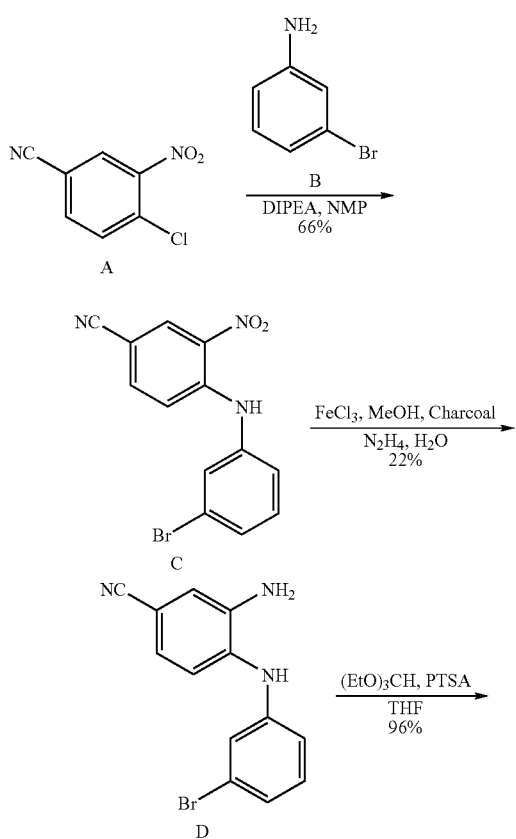

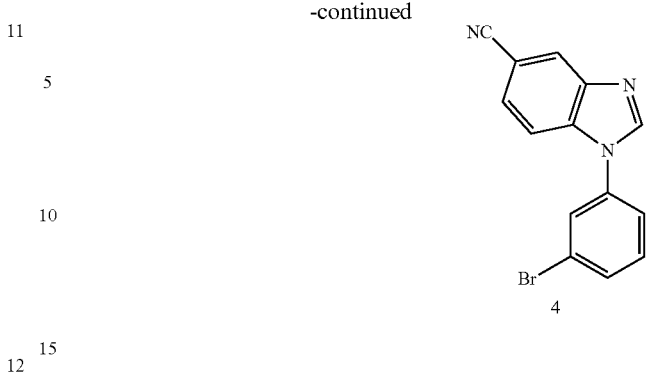

Procedure for Synthesis of 4-(3-Bromo-phenylamino)-3-nitro-benzonitrile (C)

To a mixture of 4-chloro-3-nitrobenzonitrile (A) (5 g, 27.4 mmol) and diisopropyl-ethylamine (4.24 g, 32 mmol) in NMP (40 mL) was added 3-bromoaniline (B) (4.71 g, 27.4 mmol) and the reaction mixture was stirred at 80° C. for 6 h. The reaction mixture was cooled to RT and diluted with water. The solid was filtered off, washed several times with water to remove excess 3-bromoaniline, dried under vacuum to give compound C (5.8 g, 66%) as a pale yellow solid.

Procedure for Synthesis of 3-Amino-4-(3-bromo-phenylamino)-benzonitrile (D)

To a solution of compound C (1 g, 3.14 mmol) in methanol (10 mL) was added anhydrous FeCl₃ (100 mg, 0.65 mmol) and charcoal (100 mg). The mixture was stirred at 60° C. and at that temperature hydrazine hydrate (10 mL) was added slowly where after the temperature was raised to 80° C. for 1.5 h. The reaction mixture was cooled to RT, filtered through a small pad of celite and washed with methanol. The organic layer was concentrated and washed with water, to give light brown solid D (200 mg, 22%).

Procedure for Synthesis of 1-(3-Bromo-phenyl)-1H-benzoimidazole-5-carbonitrile (4)

A mixture of compound D (1 g, 3.47 mmol), triethylorthoformate (660 mg, 4.5 mmol) and PTSA (200 mg, 1.16 mmol) in THF (10 mL) was stirred at 70° C. for 4 h. After cooling to RT, the reaction mixture was diluted with DCM, washed with sat. NaHCO₃ solution to remove PTSA, dried over Na₂SO₄ and concentrated. The residue was purified by silica gel column chromatography using 40% ethylacetate in hexane to afford compound 4 (1 g, 96%) as light brown solid, mp:168.5-174.4° C.

Synthesis of Key Intermediate 5 and 8

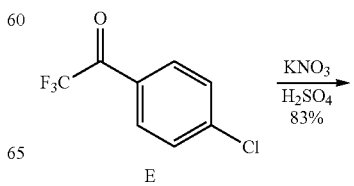

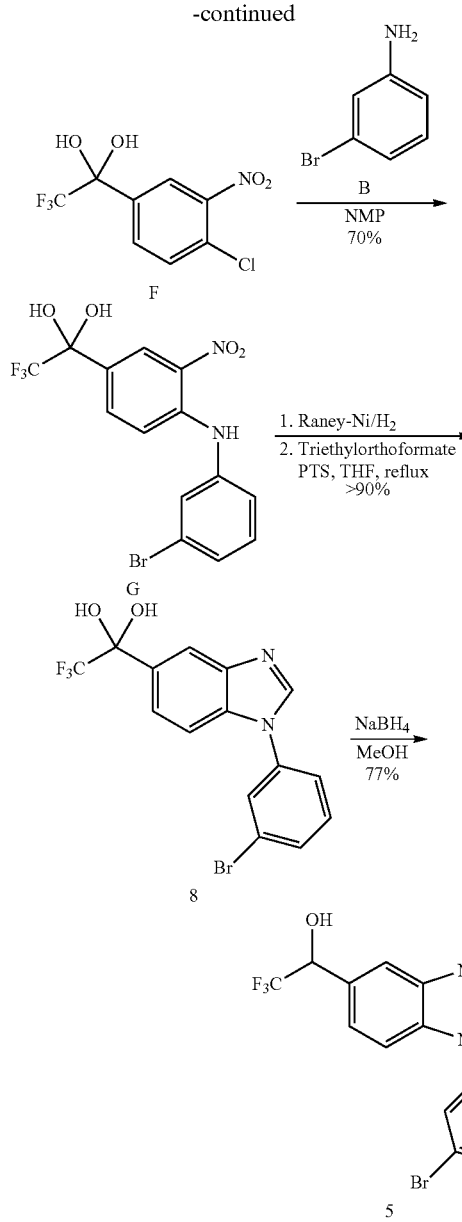

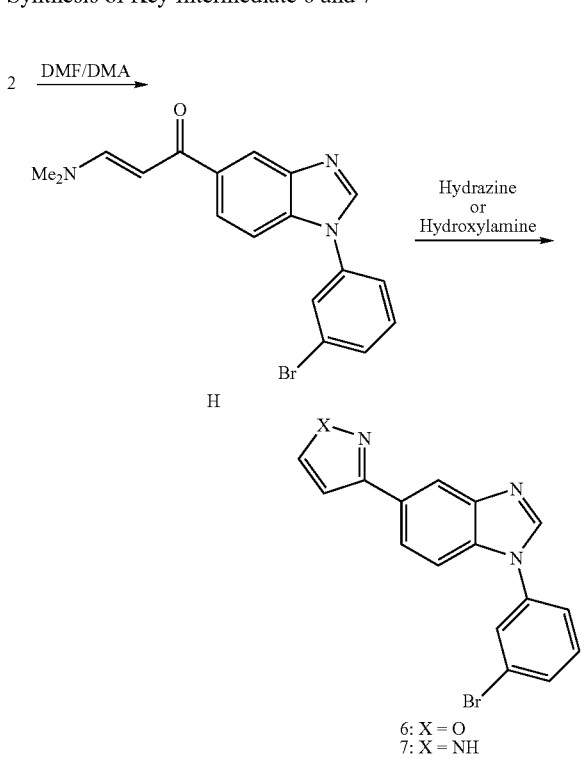

6: X = O
7: X = NH

Synthesis of Intermediate F

4'-Chloro-2,2,2-trifluoroacetophenone (5 g, 24 mmol) was dissolved in H$_2$SO$_4$conc (15 ml) and cooled to o'c. KNO$_3$ (6.05 g, 60 mmol) was added portionwise and the temperature kept below 5° C. The reaction mixture was stirred at 10° C. for 5 h and then poured into ice/H$_2$O. The water was treated with NH$_3$aq and extracted with EtOAc, dried with MgSO$_4$ and subsequently evaporated in vacuo to 6.8 g of a brown oil. The product turned out to be the hydrate of the ketone and this was purified by column chromatography (Pet. Ether/EtOAC 3:1) to give F (5.4 g, 83%) as a yellowish oil. NMR showed only the hydrated form.

Synthesis of Intermediate G

F (4.1 g, 15 mmol) and B (2.6 g, 15 mmol) was dissolved in NMP and stirred at 100° C. overnight, the reaction was stopped when LCMS showed no change in amounts of starting material and product (24 h; 73% product and 18% starting material). The reaction mixture was poured into 3M CaCl$_2$ and extracted into EtOAC. The organic phase was dried and evaporated to give crude G which was purified by column chromatography, yield 4.3 g 70% as a yellow solid.

Synthesis of 8

G (21 g, 51.5 mmol) was dissolved in EtOH 99% (200 ml) and Raney Nickel (2 mol %) was added. The reaction was hydrogenated in a H$_2$ atmosphere (1 atm) for 16 h. The reaction was then filtered through celite and the filtrate evaporated in vacuo to give a brownish oil. This was then redissolved in EtOAc and dried with MgSO$_4$ followed by evaporation of the solvent to give 18.5 g, 94% yield of a orange solid.

The orange solid was dissolved in dry THF (100 ml) and added triethylorthoformate (10.2 ml, 1.25 eq) and catalytic PTS. The reaction mixture was refluxed for 2 h after which LCMS showed complete conversion into 8. The reaction was stopped, cooled and evaporated to give 8 as a orange solid which was washed with Et$_2$O to give almost pure 8 which was used directly in the next step.

Synthesis of 5

8 (12.9 g, 33 mmol) was dissolved in MeOH (100 ml) and NaBH$_4$ (1.2 g, 33 mmol) was added portionwise. After 30 min the reaction was finished (LCMS) and the reaction was quenched with H$_2$O, a pink precipitate was filtered off and redissolved in EtOAc. The organic solution was dried with MgSO$_4$ and evaporated to give 5 as a red oil 11.8 g. Column chromatography (5% MeOH in DCM) gave a pure compound which was used for Suzuki couplings.

Synthesis of Key Intermediate 6 and 7

General Procedure for the DMF-DMA Reaction:

To a solution of 2 (14 g, 44 mmol) in 70 ml DMF was added Dimethylformamide dimethylacetal (11.8 ml, 88 mmol) and the mixture was stirred to 120° C. overnight. LCMS showed 87% product and the reaction was stopped by pouring into ice/water. The resulting yellow precipitate was filtered off and dried under vacuum to give compound H, 16.2 g, 98% yield.

Synthesis of 6

Compound H (5 g, 13.5 mmol) was dissolved in 50 ml MeOH and heated to reflux. To this solution, hydroxylamine hydrochloride (2.3 g, 33.5 mmol) was added and the reaction monitored by LCMS. After 30 min no traces of starting material was seen and the MeOH was removed in vacuo. The resulting solid was washed thoroughly with H$_2$O and Na$_2$CO$_3$ aq and then dried in a vacuum oven to give the product 6 (4.5 g, 99%). The product was pure enough to be used for the Suzuki coupling reaction.

Synthesis of 7

Compound H (16.2 g, 43.8 mmol) was dissolved in 100 ml Ethanol (99%) and hydrazine monohydrate (6.4 ml, 131 mmol) was added. The mixture was stirred overnight at room temperature. A brownish precipitate was observed and the reaction mixture was diluted with H₂O and the precipitate filtered off. The resulting product was dried in a vacuum oven to give compound 7 (13.5 g, 91%). The compound was pure enough to be used in the suzuki coupling reaction.

Synthesis of Key Intermediate 9

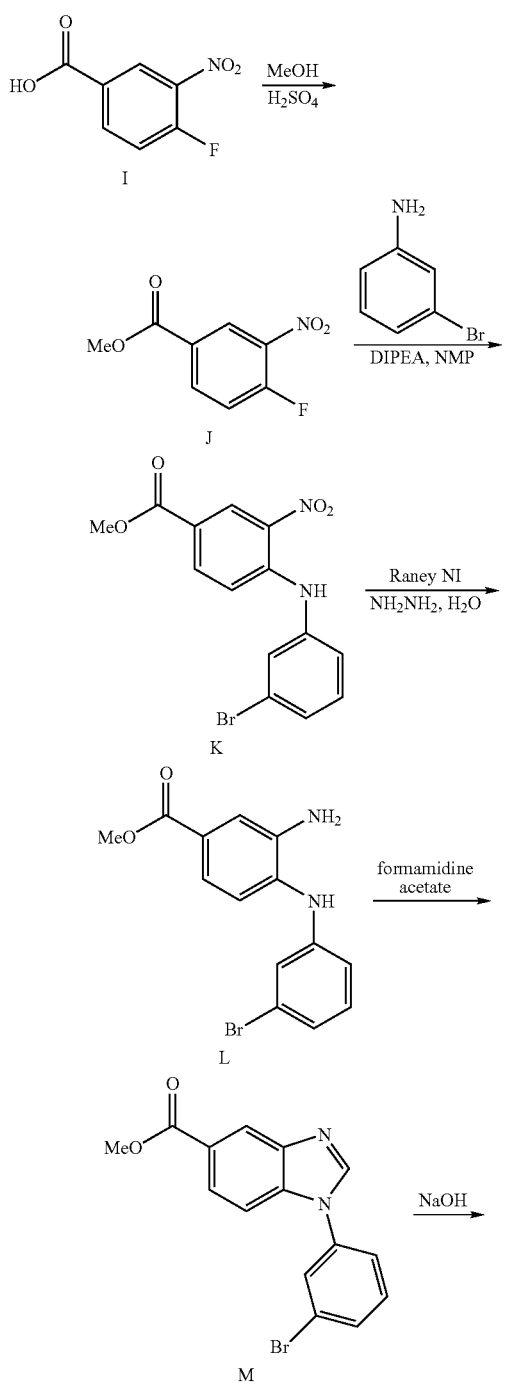

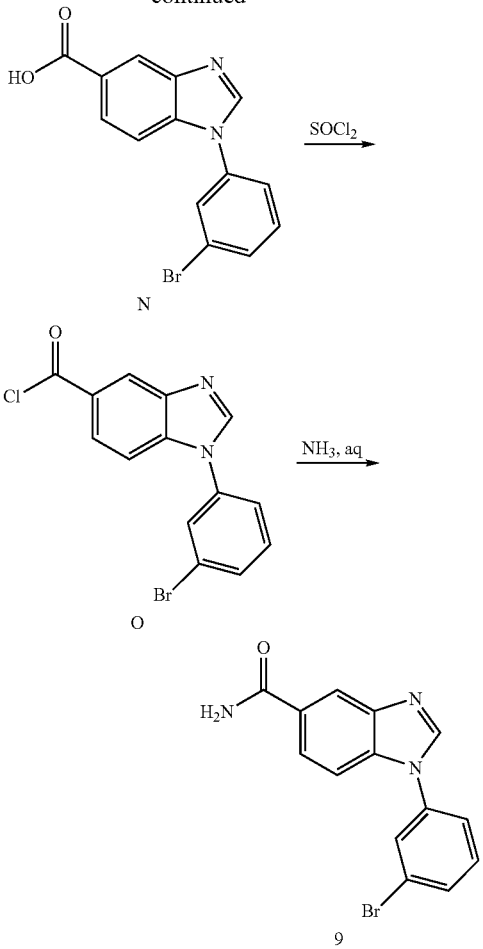

Synthesis of Intermediate J

To a solution of compound I (30.0 g, 162 mmol) in methanol (300 ml) was added conc. sulfuric acid (5 ml) and the mixture was stirred at reflux for 12 hours and then concentrated in vacuo. The concentrate was partitioned between ethyl acetate and saturated, aqueous bicarbonate. The organic layer was washed with water and brine, successively, and concentrated to afford J (31.5 g, 97%).

Synthesis of Intermediate K

To a solution of J (10.0 g, 50.2 mmol) in NMP (80 ml) was added N,N-diisopropyl ethylamine (10.5 ml, 60.3 mmol) and 3-bromoaniline (5.6 ml, 502 mmol) and the resultant mixture was stirred at 80° C. for 12 hours, whereafter it was poured into water. The precipitate was filtered off, washed with water and dried in the air to leave K (17.6 g, 75%).

Synthesis of intermediate L

To a mixture of K (10.0 g, 28.5 mmol) and hydrazine hydrate (4.9 ml, 100 mmol) in methanol (80 ml) was added Raney Nickel (1.0 g) and the resultant mixture was stirred at room temperature for three hours, whereafter it was filtered through celite. The filtrate was concentrated and the residue was triturated with water to afford the desired product, which was filtered off, washed with water and dried (9.1 g, 94%).

Synthesis of Intermediate M

To a solution of L (16.0 g, 49.8 mmol) in 2-methoxy ethanol (150 ml) was added formamidine acetate (7.78 g, 74.7 mmol) and the mixture was stirred at 100° C. for four hours. The product precipitated upon cooling. It was filtered off, washed thoroughly with water and air-dried to leave M, quantitatively (16.5 g)

35

Synthesis of Intermediate N

The above product, M (1.0 g, 3.0 mmol) was hydrolysed by treatment with sodium hydroxide (0.24 g, 6.0 mmol) in a 1:1 mixture of water and methanol (10 ml) at 50° C. for three hours. The volatile solvent was removed under reduced pressure and the product precipitated upon addition of aqueous citric acid to the residue. Filtration and drying left N, quantitatively.

Synthesis of 9 via Intermediate O

A mixture of N (0.1 g, 0.3 mmol) and thionyl chloride (5 ml) was stirred at 60° C. for two hours whereafter the mixture was evaporated to dryness. To the ice-cooled residue (O) was added conc. aqueous ammonia. Stirring of the resultant mixture afforded the desired product, 9, which was isolated by filtration (0.1 g, 100%)

Synthesis of Key Intermediates 10 and 11

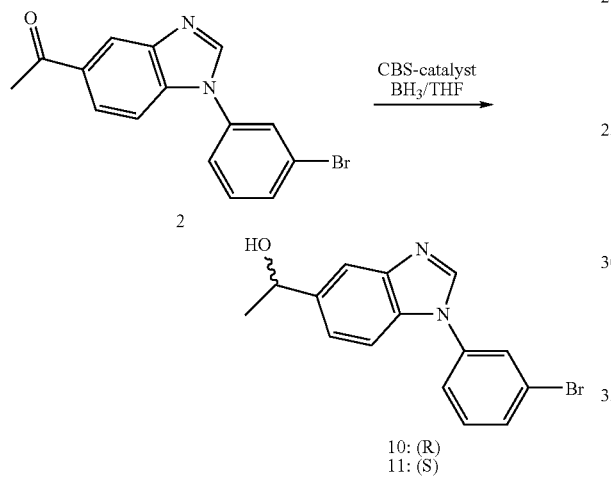

360 mg (2.4 mmol) (1S,2R)-cis-1-amino-2-indanol was dissolved in 70 ml anhydrous THF in a 500 ml reactor under an inert nitrogen atmosphere (glovebox, <5 ppm $O_2$, <5 ppm $H_2O$). 30 ml 1 M $BH_3$. THF solution (30 mmol) was added in 5 minutes and the mixture was stirred at room temperature. After 5 minutes, 150 ml of a solution of key intermediate 2 (4.0 g, 12.8 mmol) in THF was slowly (60 minutes) added to the vigorously stirred reaction mixture at r.t. (21-22° C.). A sample was taken and HPLC analysis showed >>99% conversion to the alcohol. After stirring for another 30 minutes, the reaction mixture was quenched by addition of MeOH (15 ml), followed by 30 ml 3M HCl. After stirring for 30 minutes, the mixture was neutralized with saturated $NaHCO_3$ (100 ml). The product was extracted from the reaction mixture with EtOAc (2*150 ml). The combined organic layers were evaporated and the product was extracted with dichloromethane (2*100 ml), the organic layers were dried over $Na_2SO_4$, poured over silica (30 gram) and eluted with ethylacetate. All eluent was combined and evaporated. The residue was stirred in diisopropylether (100 ml) to give an off-white fine powder, which was filtered off and dried under vacuum. Yield: 3.40 g of 10 (10.7 mmol, 84%). Chiral HPLC: e.e.=~95% in favour of the first eluting enantiomer.

11 was synthesized using the same procedure using (1R, 2S)-cis-1-amino-2-indanol. The product was purified by flash chromatography (silica, DCM:MeOH 98:2->95:5). Isolated yield: 1.9 gram (6.0 mmol, 47%), 95% e.e.

36

Synthesis of Key Intermediate 12

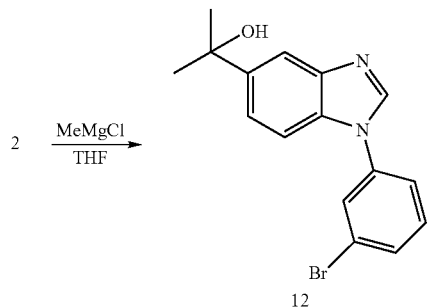

To a solution of compound 2 (5.0 g, 15.9 mmol) in THF (50 ml) was added a solution of methylmagnesium chloride in THF (3M) and the resultant mixture was stirred at ambient temperature overnight. Saturated, aqueous ammonium chloride (25 ml) was added slowly and the mixture was partitioned between ethyl acetate and water. The organic layer was dried and concentrated and purified by column chromatography on silica gel eluting with a mixture of ligroin and ethyl acetate. Evaporation of solvent from the pure fractions left 12 (3.0 g, 57%)

Example 2

Synthesis of Novel Benzimidazole Derivatives Via Suzuki Coupling

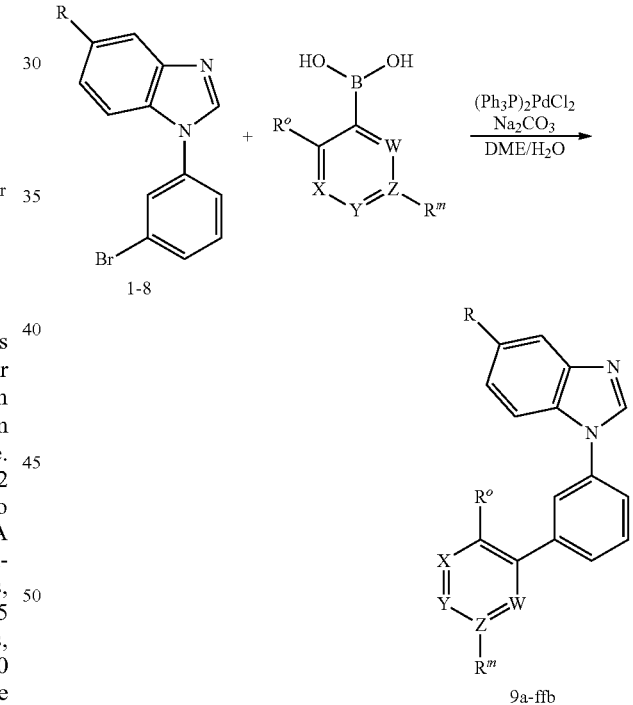

General Procedure for Suzuki Coupling: To a solution of compound 1-12 (1 eq) and arylboronic acid (1.1 eq) in mixture of solvents 1,2-dimethoxyethane and water (3:1) was added $Na_2CO_3$ (5 eq). The catalyst $(Ph_3P)_2PdCl_2$ (5 mol %) was added and the reaction mixture was stirred at 90° C. for 6-8 h. [The reaction was monitored by TLC]. The reaction mixture was cooled to RT, diluted with water, extracted with ethylacetate, dried over $Na_2SO_4$ and concentrated. The crude product was purified by is silica gel column chromatography using ethylacetate in hexane as mobile phase to furnish biaryl compounds 9a-9ffb.

The following compounds were or are prepared using the same procedure:

| No. | Starting Material | X | Y | Z | W | R | R$^o$ | R$^m$ |
|---|---|---|---|---|---|---|---|---|
| 9a | 1 | C | C | C | C | CF$_3$ | OMe | F |
| 9b | 1 | C | C | C | C | CF$_3$ | OCF$_3$ | H |
| 9c | 1 | C | C | C | C | CF$_3$ | C(=O)Me | H |
| 9d | 1 | C | C | C | C | CF$_3$ | OMe | Cl |
| 9e | 1 | C | C | C | C | CF$_3$ | C(=O)NH$_2$ | H |
| 9f | 1 | C | C | C | C | CF$_3$ | Me | H |
| 9g | 1 | C | C | C | C | CF$_3$ | OMe | H |
| 9h | 1 | C | C | C | C | CF$_3$ | OiPr | H |
| 9i | 1 | C | C | C | C | CF$_3$ | CN | H |
| 9j | 1 | C | C | C | C | CF$_3$ | OEt | H |
| 9k | 1 | C | C | C | C | OF$_3$ | Et | H |
| 9l | 1 | C | C | C | C | CF$_3$ | NHSO$_2$Me | H |
| 9m | 1 | C | C | C | C | CF$_3$ | (4-Morfolinyl)-methyl | H |
| 9n | 1 | C | C | C | C | CF$_3$ | OH | H |
| 9o | 1 | C | C | C | C | CF$_3$ | SO$_2$NMe$_2$ | H |
| 9p | 1 | C | C | C | C | CF$_3$ | CH$_2$OMe | H |
| 9q | 1 | C | C | C | C | CF$_3$ | Cl | H |
| 9r | 2 | C | C | C | C | C(=O)Me | CN | H |
| 9s | 4 | C | C | C | C | CN | OMe | H |
| 9t | 4 | C | C | C | C | CN | CN | H |
| 9u | 4 | C | C | C | C | CN | Cl | H |
| 9v | 4 | C | C | C | C | CN | OiPr | H |
| 9x | 4 | C | C | C | C | CN | OEt | H |
| 9y | 4 | C | C | C | C | CN | Me | H |
| 9z | 4 | C | C | C | C | CN | Et | H |
| 9aa | 4 | C | C | C | C | CN | OMe | F |
| 9ab | 4 | C | C | C | C | CN | C(=O)Me | H |
| 9ac | 2 | N | C | C | C | C(=O)Me | OH | H |
| 9ad | 2 | N | C | C | C | C(=O)Me | OMe | H |
| 9ae | 5 | C | C | C | C | CF$_3$CH(OH) | OMe | H |
| 9af | 5 | C | C | C | C | CF$_3$CH(OH) | Me | H |
| 9ag | 6 | C | C | C | C | 5-Isoxazolyl | CN | H |
| 9ah | 6 | C | C | C | C | 5-Isoxazolyl | OMe | Cl |
| 9ai | 6 | C | C | C | C | 5-Isoxazolyl | C(=O)Me | H |
| 9aj | 7 | C | C | C | C | 3-Pyrazolyl | C(=O)Me | H |
| 9ak | 7 | C | C | C | C | 3-Pyrazolyl | OMe | Cl |
| 9al | 7 | C | C | C | C | 3-Pyrazolyl | CN | H |
| 9am | 1 | N | C | C | C | CF$_3$ | F | H |
| 9an | 1 | N | C | C | C | CF$_3$ | CF$_3$ | H |
| 9ao | 1 | N | COMe | N | C | CF$_3$ | OMe | H |
| 9ap | 1 | N | C | C | C | CF$_3$ | Cl | H |
| 9aq | 6 | C | C | C | C | 5-isoxazolyl | C(=O)NH$_2$ | H |
| 9ar | 3 | C | C | C | C | CHO | OMe | H |
| 9as | 8 | C | C | C | C | C((OH)$_2$)CF$_3$ | OMe | H |
| 9at | 8 | C | C | C | C | C((OH)$_2$)CF$_3$ | Me | H |
| 9au | 2 | C | C | C | C | C=OMe | 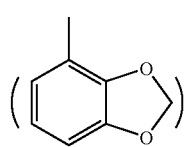 | H |
| 9av | 1 | C | C | C | C | CF$_3$ | OH | F |
| 9ax | 10 | C | C | C | C | (R)—CH(OH)CH$_3$ | OMe | H |
| 9ay | 10 | C | C | C | C | (R)—CH(OH)CH$_3$ | C(=O)NH$_2$ | H |
| 9az | 10 | C | C | C | C | (R)—CH(OH)CH$_3$ | OMe | Cl |
| 9aaa | 10 | C | C | C | C | (R)—CH(OH)CH$_3$ | NHSO$_2$Me | H |
| 9aab | 9 | C | C | C | C | C(=O)NH$_2$ | OMe | H |
| 9aac | 12 | C | C | C | C | C(CH$_3$)$_2$OH | CN | H |
| 9aad | 12 | C | C | C | C | C(CH$_3$)$_2$OH | OMe | H |
| 9aae | 11 | C | C | C | C | (S)—CH(OH)CH$_3$ | OMe | Cl |
| 9aaf | 11 | C | C | C | C | (S)—CH(OH)CH$_3$ | NHSO$_2$Me | H |
| 9aag | 11 | C | C | C | C | (S)—CH(OH)CH$_3$ | OMe | H |
| 9aah | 11 | C | C | C | C | (S)—CH(OH)CH$_3$ | C(=O)NH$_2$ | H |
| 9aai | 12 | C | C | C | C | C(CH$_3$)$_2$OH | OMe | Cl |
| 9aaj | 9 | C | C | C | C | C(=O)NH$_2$ | OMe | F |
| 9aak | 9 | C | C | C | C | C(=O)NH$_2$ | OMe | Cl |
| 9aal | 10 | C | C | C | C—OMe | (R)—CH(OH)CH$_3$ | OMe | H |
| 9aam | 9 | C | C | C | C—OMe | C(=O)NH$_2$ | F | H |
| 9aan | 9 | C | C | C | C—OMe | C(=O)NH$_2$ | Cl | H |
| 9aao | 12 | C—F | C | C | C | C(CH$_3$)$_2$OH | OMe | H |
| 9aap | 10 | C—F | C | C | C | (R)—CH(OH)CH$_3$ | OMe | H |
| 9aaq | 12 | C—OMe | C | C | C | C(CH$_3$)$_2$OH | OMe | H |
| 9aar | 10 | C | C | C | C—F | (R)—CH(OH)CH$_3$ | OMe | H |

-continued

| No. | Starting Material | X | Y | Z | W | R | R$^o$ | R$^m$ |
|---|---|---|---|---|---|---|---|---|
| 9aas | 10 | C—OMe | C | C | C | (R)—CH(OH)CH$_3$ | OMe | H |
| 9aat | 10 | C | C—OMe | C | C | (R)—CH(OH)CH$_3$ | OMe | H |
| 9aau | 12 | C—Cl | C | C | C | C(CH$_3$)$_2$OH | OH | H |
| 9aav | 12 | C | C | C | C—OMe | C(CH$_3$)$_2$OH | OMe | H |
| 9aax | 10 | C | C | C | C—Cl | (R)—CH(OH)CH$_3$ | OMe | H |
| 9aay | 12 | C | C—OMe | C | C | C(CH$_3$)$_2$OH | OMe | H |
| 9aaz | 12 | C | C | C | C—F | C(CH$_3$)$_2$OH | OMe | H |
| 9aba | 10 | N | C | C | C | (R)—CH(OH)CH$_3$ | F | H |
| 9aca | 11 | N | C | C | C | (S)—CH(OH)CH$_3$ | F | H |
| 9ada | 12 | N | C | C | C | CH(OH)CH$_3$ | F | H |
| 9aea | 4 | C | C | C | C—OMe | CN | OMe | H |
| 9afa | 4 | C—F | C | C | C | CN | OMe | H |
| 9aga | 4 | C | C | C | C—F | CN | OMe | H |
| 9aha | 4 | C | C | C | C—Cl | CN | OMe | H |
| 9aia | 4 | C—Me | C | C | C—F | CN | Cl | H |
| 9aja | 4 | C | C | C | C—F | CN | Cl | Me |
| 9aka | 4 | C | C—OMe | C | C | CN | OMe | H |
| 9ala | 4 | C—OMe | C | C | C | CN | OMe | H |
| 9ama | 4 | N | C | C | C | CN | F | Br |
| 9ana | 4 | C | N | C | C | CN | F | Br |
| 9aoa | 4 | C | C | C | C—F | CN | F | H |
| 9apa | 4 | C | C | C | C—Cl | CN | Cl | H |
| 9aqa | 4 | C | C | C | C | CN | Piperazin-1-yl | H |
| 9ara | 4 | C | N | C | C | CN | OMe | Br |
| 9asa | 4 | C—Cl | N | C | C | CN | F | H |
| 9ata | 4 | C | C | C | C—F | CN | OMe | F |
| 9aua | 4 | C | C—F | C | C | CN | OMe | H |
| 9ava | 4 | C | C | C | C | CN | Cl | CN |
| 9axa | 4 | C—Cl | C | C | C | CN | OH | H |
| 9aya | 4 | C—Cl | C | C | C—F | CN | F | H |
| 9aza | 4 | N | C—OMe | N | C | CN | OMe | — |
| 9baa | 4 | N | C—F | C | C | CN | F | H |
| 9caa | 4 | C | N | C | C | CN | F | H |
| 9daa | 4 | C | N | C | C | CN | Cl | H |
| 9eaa | 4 | N | C | C | C | CN | Cl | H |
| 9faa | 4 | C | C | C | C | CN | (4-Morfolinyl)-methyl | H |
| 9jaa | 4 | C—F | C | C | C | CN | OMe | F |
| 9kaa | 4 | C | C | C | C | CN | NHSO$_2$Me | H |
| 9laa | 4 | N | C | C | C | CN | F | H |
| 9maa | 4 | C | C | C | C | CN | OMe | Cl |
| 9naa | 4 | C | C | C | C | CN | C(=O)NH$_2$ | H |
| 9oaa | 9 | C | C | C | C—OMe | C(=O)NH$_2$ | OMe | H |
| 9paa | 9 | C—F | C | C | C | C(=O)NH$_2$ | OMe | H |
| 9qaa | 9 | C—Me | C | C | C—F | C(=O)NH$_2$ | Cl | H |
| 9raa | 9 | C | C | C | C—F | C(=O)NH$_2$ | Cl | Me |
| 9saa | 9 | C | C—OMe | C | C | C(=O)NH$_2$ | OMe | H |
| 9taa | 9 | C—OMe | C | C | C | C(=O)NH$_2$ | OMe | H |
| 9uaa | 9 | N | C | C | C | C(=O)NH$_2$ | F | Br |
| 9vaa | 9 | C | N | C | C | C(=O)NH$_2$ | F | Br |
| 9xaa | 9 | C | C | C | C—F | C(=O)NH$_2$ | F | H |
| 9yaa | 9 | C | C | C | C—Cl | C(=O)NH$_2$ | Cl | H |
| 9zaa | 9 | C | C | C | C | C(=O)NH$_2$ | Piperazin-1-yl | H |
| 9bba | 9 | C | N | C | C | C(=O)NH$_2$ | OMe | Br |
| 9bbb | 9 | C—Cl | N | C | C | C(=O)NH$_2$ | F | H |
| 9bbc | 9 | C | C | C | C—F | C(=O)NH$_2$ | OMe | F |
| 9bbd | 9 | C | C—F | C | C | C(=O)NH$_2$ | OMe | H |
| 9bbe | 9 | C | C | C | C | C(=O)NH$_2$ | Cl | CN |
| 9bbf | 9 | C—Cl | C | C | C | C(=O)NH$_2$ | OH | H |
| 9bbg | 9 | C—Cl | C | C | C—F | C(=O)NH$_2$ | F | H |
| 9bbh | 9 | N | C—OMe | N | C | C(=O)NH$_2$ | OMe | — |
| 9bbi | 9 | N | C—F | C | C | C(=O)NH$_2$ | F | H |
| 9bbj | 9 | C | N | C | C | C(=O)NH$_2$ | F | H |
| 9bbk | 9 | C | N | C | C | C(=O)NH$_2$ | Cl | H |
| 9bbl | 9 | N | C | C | C | C(=O)NH$_2$ | Cl | H |
| 9bbm | 9 | C | C | C | C | C(=O)NH$_2$ | (4-Morfolinolinyl)-methyl | H |
| 9bbq | 9 | C—F | C | C | C | C(=O)NH$_2$ | OMe | F |
| 9bbr | 9 | C | C | C | C | C(=O)NH$_2$ | NHSO$_2$Me | H |
| 9bbs | 9 | N | C | C | C | C(=O)NH$_2$ | F | H |
| 9bbt | 9 | C | C | C | C | C(=O)NH$_2$ | C(=O)NH$_2$ | H |
| 9bbu | 10 | C—Me | C | C | C—F | (R)—CH(OH)CH$_3$ | Cl | H |
| 9bbv | 10 | C | C | C | C—F | (R)—CH(OH)CH$_3$ | Cl | Me |
| 9bbx | 10 | N | C | C | C | (R)—CH(OH)CH$_3$ | F | Br |
| 9bby | 10 | C | N | C | C | (R)—CH(OH)CH$_3$ | F | Br |

-continued

| No. | Starting Material | X | Y | Z | W | R | R$^o$ | R$^m$ |
|---|---|---|---|---|---|---|---|---|
| 9bbz | 10 | C | C | C | C—F | (R)—CH(OH)CH$_3$ | F | H |
| 9cca | 10 | C | C | C | C—Cl | (R)—CH(OH)CH$_3$ | Cl | H |
| 9ccb | 10 | C | C | C | C | (R)—CH(OH)CH$_3$ | Piperazin-1-yl | H |
| 9ccc | 10 | C | N | C | C | (R)—CH(OH)CH$_3$ | OMe | Br |
| 9ccd | 10 | C—Cl | N | C | C | (R)—CH(OH)CH$_3$ | F | H |
| 9cce | 10 | C | C | C | C—F | (R)—CH(OH)CH$_3$ | OMe | F |
| 9ccf | 10 | C | C—F | C | C | (R)—CH(OH)CH$_3$ | OMe | H |
| 9ccg | 10 | C | C | C | C | (R)—CH(OH)CH$_3$ | Cl | CN |
| 9cch | 10 | C—Cl | C | C | C | (R)—CH(OH)CH$_3$ | OH | H |
| 9cci | 10 | C—Cl | C | C | C—F | (R)—CH(OH)CH$_3$ | F | H |
| 9ccj | 10 | N | C—OMe | N | C | (R)—CH(OH)CH$_3$ | OMe | — |
| 9cck | 10 | N | C—F | C | C | (R)—CH(OH)CH$_3$ | F | H |
| 9ccl | 10 | C | N | C | C | (R)—CH(OH)CH$_3$ | F | H |
| 9ccm | 10 | C | N | C | C | (R)—CH(OH)CH$_3$ | Cl | H |
| 9ccn | 10 | N | C | C | C | (R)—CH(OH)CH$_3$ | Cl | H |
| 9cco | 10 | C | C | C | C | (R)—CH(OH)CH$_3$ | (4-Morfo-linyl)-methyl | H |
| 9ccs | 10 | C—F | C | C | C | (R)—CH(OH)CH$_3$ | OMe | F |
| 9cct | 11 | C | C | C | C—OMe | (S)—CH(OH)CH$_3$ | OMe | H |
| 9ccu | 11 | C—F | C | C | C | (S)—CH(OH)CH$_3$ | OMe | H |
| 9ccv | 11 | C | C | C | C—F | (S)—CH(OH)CH$_3$ | OMe | H |
| 9ccx | 11 | C—OMe | C | C | C | (S)—CH(OH)CH$_3$ | OMe | H |
| 9ccy | 11 | C | C—OMe | C | C | (S)—CH(OH)CH$_3$ | OMe | H |
| 9ccz | 11 | C | C | C | C—Cl | (S)—CH(OH)CH$_3$ | OMe | H |
| 9dda | 11 | C—Me | C | C | C—F | (S)—CH(OH)CH$_3$ | Cl | H |
| 9ddb | 11 | C | C | C | C—F | (S)—CH(OH)$_3$ | Cl | Me |
| 9ddc | 11 | N | C | C | C | (S)—CH(OH)CH$_3$ | F | Br |
| 9ddd | 11 | C | N | C | C | (S)—CH(OH)CH$_3$ | F | Br |
| 9dde | 11 | C | C | C | C—F | (S)-CH(OH)CH$_3$ | F | H |
| 9ddf | 11 | C | C | C | C—Cl | (S)—CH(OH)CH$_3$ | Cl | H |
| 9ddg | 11 | C | C | C | C | (S)—CH(OH)CH$_3$ | Piperazin-1-yl | H |
| 9ddh | 11 | C | N | C | C | (S)—CH(OH)CH$_3$ | OMe | Br |
| 9ddi | 11 | C—Cl | N | C | C | (S)—CH(OH)CH$_3$ | F | H |
| 9ddj | 11 | C | C | C | C—F | (S)—CH(OH)CH$_3$ | OMe | F |
| 9ddk | 11 | C | C—F | C | C | (S)—CH(OH)CH$_3$ | OMe | H |
| 9ddl | 11 | C | C | C | C | (S)—CH(OH)CH$_3$ | Cl | CN |
| 9ddm | 11 | C—Cl | C | C | C | (S)—CH(OH)CH$_3$ | OH | H |
| 9ddn | 11 | C—Cl | C | C | C—F | (S)—CH(OH)CH$_3$ | F | H |
| 9ddo | 11 | N | C—OMe | N | C | (S)—CH(OH)CH$_3$ | OMe | — |
| 9ddp | 11 | N | C—F | C | C | (S)—CH(OH)CH$_3$ | F | H |
| 9ddq | 11 | C | N | C | C | (S)—CH(OH)CH$_3$ | F | H |
| 9ddr | 11 | C | N | C | C | (S)—CH(OH)CH$_3$ | Cl | H |
| 9dds | 11 | N | C | C | C | (S)—CH(OH)CH$_3$ | Cl | H |
| 9ddt | 11 | C | C | C | C | (S)—CH(OH)CH$_3$ | (4-Morfo-linyl)-methyl | H |
| 9ddy | 11 | C—F | C | C | C | (S)—CH(OH)CH$_3$ | OMe | F |
| 9ddz | 12 | C | C | C | C—Cl | C(CH$_3$)$_2$OH | OMe | H |
| 9eea | 12 | C—Me | C | C | C—F | C(CH$_3$)$_2$OH | Cl | H |
| 9eeb | 12 | C | C | C | C—F | C(CH$_3$)$_2$OH | Cl | Me |
| 9eec | 12 | N | C | C | C | C(CH$_3$)$_2$OH | F | Br |
| 9eed | 12 | C | N | C | C | C(CH$_3$)$_2$OH | F | Br |
| 9eee | 12 | C | C | C | C—F | C(CH$_3$)$_2$OH | F | H |
| 9eef | 12 | C | C | C | C—Cl | C(CH$_3$)$_2$OH | Cl | H |
| 9eeg | 12 | C | C | C | C | C(CH$_3$)$_2$OH | Miperazin-1-yl | H |
| 9eeh | 12 | C | N | C | C | C(CH$_3$)$_2$OH | OMe | Br |
| 9eei | 12 | C—Cl | N | C | C | C(CH$_3$)$_2$OH | F | H |
| 9eej | 12 | C | C | C | C—F | C(CH$_3$)$_2$OH | OMe | F |
| 9eek | 12 | C | C—F | C | C | C(CH$_3$)$_2$OH | OMe | H |
| 9eel | 12 | C | C | C | C | C(CH$_3$)$_2$OH | Cl | CN |
| 9eem | 12 | C—Cl | C | C | C—F | C(CH$_3$)$_2$OH | F | H |
| 9een | 12 | N | C—OMe | N | C | C(CH$_3$)$_2$OH | OMe | — |
| 9eeo | 12 | N | C—F | C | C | C(CH$_3$)$_2$OH | F | H |
| 9eep | 12 | C | N | C | C | C(CH$_3$)$_2$OH | F | H |
| 9eeq | 12 | C | N | C | C | C(CH$_3$)$_2$OH | Cl | H |
| 9eer | 12 | N | C | C | C | C(CH$_3$)$_2$OH | Cl | H |
| 9ees | 12 | C | C | C | C | C(CH$_3$)$_2$OH | (4-Morfo-linyl)-methyl | H |
| 9eex | 12 | C—F | C | C | C | C(CH$_3$)$_2$OH | OMe | F |
| 9eey | 12 | C | C | C | C | C(CH$_3$)$_2$OH | C(=O)NH$_2$ | H |
| 9eez | 12 | C | C | C | C | C(CH$_3$)$_2$OH | NHSO$_2$Me | H |
| 9ffa | 12 | C | C | C | C | C(CH$_3$)$_2$OH | OMe | F |
| 9ffb | 2 | C | C | C | C | C=OMe | OMe | Cl |

1-(4'-Fluoro-2'-methoxy-biphenyl-3-yl)-5-trifluoromethyl-1H-benzoimidazole 9a:
white solid, MP: 95.5° C.
1-(2'-Trifluoromethoxy-biphenyl-3-yl)-5-trifluoromethyl-1H-benzoimidazole 9b:
White solid. MP: 86.5-87° C.
1-(2'-Acetyl-biphenyl-3-yl)-5-trifluoromethyl-1H-benzoimidazole 9c: White solid. MP: 122-123° C.
1-(4'-Chloro-2'-methoxy-biphenyl-3-yl)-5-trifluoromethyl-1H-benzoimidazole 9d:
LC-ESI-HRMS of [M+H]+ shows 403.0803 Da. Calc. 403.0825 Da, dev. −5.5 ppm
1-(2'-Methoxy-biphenyl-3-yl)-5-1H-benzoimidazole-5-carboxylic acid amide 9e:
LC-ESI-HRMS of [M+H]+ shows 382.1178 Da. Calc. 382.116721 Da, dev. 2.8 ppm
1-(2'-Methyl-biphenyl-3-yl)-5-trifluoromethyl-1H-benzoimidazole 9f: LC-ESI-HRMS of [M+H]+ shows 353.1259 Da. Calc. 353.126557 Da, dev. −1.9 ppm
1-(2'-Methoxy-biphenyl-3-yl)-5-trifluoromethyl-1H-benzoimidazole 9g: LC-ESI-HRMS of [M+H]+ shows 369.1201 Da. Calc. 369.121472 Da, dev. −3.7 ppm
1-(2'-Isopropoxy-biphenyl-3-yl)-5-trifluoromethyl-1H-benzoimidazole 9h: LC-ESI-HRMS of [M+H]+ shows 397.1548 Da. Calc. 397.152772 Da, dev. 5.1 ppm
1-(2'-Cyano-biphenyl-3-yl)-5-trifluoromethyl-1H-benzoimidazole 9I: LC-ESI-HRMS of [M+H]+ shows 364.1044 Da. Calc. 364.106156 Da, dev. −4.8 ppm
1-(2'-Ethoxy-biphenyl-3-yl)-5-trifluoromethyl-1H-benzoimidazole 9j: LC-ESI-HRMS of [M+H]+ shows 383.1371 Da. Calc. 383.137122 Da, dev. −0.1 ppm
1-(2'-Ethyl-biphenyl-3-yl)-5-trifluoromethyl-1H-benzoimidazole 9k: LC-ESI-HRMS of [M+H]+ shows 367.1408 Da. Calc. 367.142207 Da, dev. −3.8 ppm
1-(2'-Methanesulfonamido-biphenyl-3-yl)-5-trifluoromethyl-1H-benzoimidazole 9l:
LC-ESI-HRMS of [M+H]+ shows 432.0972 Da. Calc. 432.099357 Da, dev. −5 ppm
1-(2'-(Morpholin-4-yl-methyl)-biphenyl-3-yl)-5-trifluoromethyl-1H-benzoimidazole 9m: LC-ESI-HRMS of [M+H]+ shows 438.1785 Da. Calc. 438.179321 Da, dev. −1.9 ppm
1-(2'-Hydroxy-biphenyl-3-yl)-5-trifluoromethyl-1H-benzoimidazole 9n: LC-ESI-HRMS of [M+H]+ shows 355.1062 Da. Calc. 355.105822 Da, dev. 1.1 ppm
1-(2'-(N,N-Dimethyl-sulphamoyl)-biphenyl-3-yl)-5-trifluoromethyl-1H-benzoimidazole 9o: LC-ESI-HRMS of [M+H]+ shows 446.1149 Da. Calc. 446.115007 Da, dev. −0.2 ppm
1-(2'-Methoxymethyl-biphenyl-3-yl)-5-trifluoromethyl-1H-benzoimidazole 9p: LC-ESI-HRMS of [M+H]+ shows 383.1379 Da. Calc. 383.137122 Da, dev. 2 ppm
1-(2'-Chloro-biphenyl-3-yl)-5-trifluoromethyl-1H-benzoimidazole 9q: LG-ESI-HRMS of [M+H]+ shows 373.0721 Da. Calc. 373.071935 Da, dev. 0.4 ppm
5-Acetyl-1-(2'-cyano-biphenyl-3-yl)-1H-benzoimidazole 9r:
This compound can be prepared using the above mentioned method. LC-ESI-HRMS of [M+H]+ shows 393.1413 Da. Calc. 393.141459 Da, dev. −0.4 ppm
1-(2'-Methoxy-biphenyl-3-yl)-1H-benzoimidazole-5-carbonitrile 9s: white solid, MP-176.4-177.1° C. LC-ESI-HRMS of [M+H]+ shows 326.1288 Da. Calc. 326.129337 Da, dev. −1.6 ppm
1-(2'-Cyano-biphenyl-3-yl)-1H-benzoimidazole-5-carbonitrile 9t: white solid, MP-217.4-218.6° C. LC-ESI-HRMS of [M+H]+ shows 321.1145 Da. Calc. 321.114021 Da, dev. 1.5 ppm
1-(2'-Chloro-biphenyl-3-yl)-1H-benzoimidazole-5-carbonitrile 9u: white solid, MP-150.6-151.2° C. LC-ESI-HRMS of [M+H]+ shows 330.0794 Da. Calc. 330.0798 Da, dev. −1.2 ppm
1-(2'-Isopropoxy-biphenyl-3-yl)-1H-benzoimidazole-5-carbonitrile 9v: white solid, MP-107.2-109.1° C. LC-ESI-HRMS of [M+H]+ shows 354.1604 Da. Calc. 354.160637 Da, dev. −0.7 ppm
1-(2'-Ethoxy-biphenyl-3-yl)-1H-benzoimidazole-5-carbonitrile 9x: white solid, MP-149.2-151.5° C. LC-ESI-HRMS of [M+H]+ shows 340.1443 Da. Calc. 340.144987 Da, dev. −2 ppm
1-(2'-Methyl-biphenyl-3-yl)-1H-benzoimidazole-5-carbonitrile 9y: white solid, MP-132.1-134.8° C. LC-ESI-HRMS of [M+H]+ shows 310.134 Da. Calc. 310.134422 Da, dev. −1.4 ppm
1-(2'-Ethyl-biphenyl-3-yl)-1H-benzoimidazole-5-carbonitrile 9z: colorless gum. LC-ESI-HRMS of [M+H]+ shows 324.149 Da. Calc. 324.150072 Da, dev. −3.3 ppm
1-(5'-Fluoro-2'-methoxy-biphenyl-3-yl)-1H-benzoimidazole-5-carbonitrile 9aa:
Orange powder, MP: 216-217° C.
1-(2'-Acetyl-biphenyl-3-yl)-1H-benzoimidazole-5-carbonitrile 9ab: LC-ESI-HRMS of [M+H]+ shows 338.1281 Da. Calc. 338.129337 Da, dev. −3.7 ppm
5-Acetyl-[3-(2-hydroxy-pyridin-3-yl)-phenyl]-1H-benzoimidazole 9ac: Brown solid. MP: 254-257° C.
5-Acetyl-[3-(2-methoxy-pyridin-3-yl)-phenyl]-1H-benzoimidazole 9ad: Yellow crystals. MP: 204-206° C.
5-(1-Hydroxy-2,2,2-trifluoro-ethyl)-1-(2'-methoxy-biphenyl-3-yl)-1H-benzoimidazole 9ae:
LC-ESI-HRMS of [M+H]+ shows 399.1303 Da. Calc. 399.132037 Da, dev. −4.4 ppm
5-(1-Hydroxy-2,2,2-trifluoro-ethyl)-1-(2'-methyl-biphenyl-3-yl)-1H-benzoimidazole 9af: LC-ESI-HRMS of [M+H]+ shows 383.1373 Da. Calc. 383.137122 Da, dev. 0.5 ppm
5-(5-Isoxazolyl)-1-(2'-cyano-biphenyl-3-yl)-1H-benzoimidazole 9ag: LC-ESI-HRMS of [M+H]+ shows 363.1237 Da. Calc. 363.124586 Da, dev. −2.4 ppm
5-(5-Isoxazolyl)-1-(5'-chloro-2'-methoxy-biphenyl-3-yl)-1H-benzoimidazole 9ah:
LC-ESI-HRMS of [M+H]+ shows 402.1014 Da. Calc. 402.10093 Da, dev. 1.2 ppm
5-(5-Isoxazolyl)-1-(2'-acetyl-biphenyl-3-yl)-1H-benzoimidazole 9ai.
5-(1H-3-Pyrazolyl)-1-(2'-acetyl-biphenyl-3-yl)-1H-benzoimidazole 9aj.
5-(1H-3-Pyrazolyl)-1-(2-methoxy-biphenyl-3-yl)-1H-benzoimidazole 9ak: LC-ESI-HRMS of [M+H]+ shows 401.1174 Da. Calc. 401.116914 Da, dev. 1.2 ppm
5-(1H-3-Pyrazolyl)-1-(2'-cyano-biphenyl-3-yl)-1H-benzoimidazole gal: LC-ESI-HRMS of [M+H]+ shows 362.141 Ca. Calc. 362.14057 Da, dev. 1.2 ppm
1-[3-(2-Fluoro-pyridin-3-yl)-phenyl]-5-trifluoromethyl-1H-benzoimidazole 1.9 ppm:
LC-ESI-HRMS of [M+H]+ shows 358.0974 Da. Calc. 358.096734 Da, dev. 1.9 ppm
1-[3-(2-Methoxy-pyridin-3-yl)-phenyl]-5-trifluoromethyl-1H-benzoimidazole 9an:
LC-ESI-HRMS of [M+H]+ shows 370.1148 Da. Calc. 370.116721 Da, dev. −5.2 ppm
1-[3-(2,4-dimethoxy-pyrimidine-5-yl)-phenyl]-5-trifluoromethyl-1H-benzoimidazole 9ao: LC-ESI-HRMS of [M+H]+ shows 401.1218 Da. Calc. 401.122535 Da, dev. −1.8 ppm
1-[3-(2-Chloro-pyridin-3-yl)-phenyl]-5-trifluoromethyl-1H-benzoimidazole 9ap: LC-ESI-HRMS of [M+H]+ shows 374.0662 Da. Calc. 374.067184 Da, dev. −2.6 ppm
5-(5-Isoxazolyl)-1-(2'-carbamoyl-biphenyl-3-yl)-1H-benzoimidazole 9aq: LC-ESI-HRMS of [M+H]+ shows 381.1346 Da. Calc. 381.135151 Da, dev. −1.4 ppm
5-Formyl-1-(2'-methoxy-biphenyl-3-yl)-1H-benzoimidazole 9ar.

1-(2'-Methoxy-biphenyl-3-yl)-5-(2,2,2-trifluoro-1,1-dihydroxy-ethyl)-1H-benzoimidazole 9as: LC-ESI-HRMS of [M+H]+ shows 415.1281 Da. Calc. 415.126952 Da, dev. 2.8 ppm 1-(2'-Methyl-biphenyl-3-yl)-5-(2,2,2-trifluoro-1,1-dihydroxy-ethyl)-1H-benzoimidazole 9at: LC-ESI-HRMS of [M+H]+ shows 399.1323 Da. Calc. 399.132037 Da, dev. 0.7 ppm 5-Acetyl-1-(3-(benzo[1,3]-dioxol-4-yl)phenyl)-1H-benzoimidazole 9au: LC-ESI-HRMS of [M+H]+ shows 379.1238 Da. Calc. 379.122825 Da, dev. 2.6 ppm 5-Fluoro-3'-(5-trifluoromethyl-benzoimidazol-1-yl)-biphenyl-2-ol 9av: LC-ESI-HRMS of [M+H]+ shows 373.0975 Da. Calc. 373.0964 Da, dev. 2.9 ppm (R)-1-[1-(2'-Methoxy-biphenyl-3-yl)-1H-benzoimidazol-5-yl]-ethanol 9ax: LC-ESI-HRMS of [M+H]+ shows 345.1602 Da. Calc. 345.160303 Da, dev. −0.3 ppm 3'-[5-((R)-1-Hydroxy-ethyl)-benzoimidazol-1-yl]-biphenyl-2-carboxylic acid amide 9ay:
LC-ESI-HRMS of [M+H]+ shows 358.1573 Da. Calc. 358.155552 Da, dev. 4.9 ppm (R) 1-[1-(5'-Chloro-2'-methoxy-biphenyl-3-yl)-1H-benzoimidazol-5-yl]-ethanol 9az:
LC-ESI-HRMS of [M+H]+ shows 379.1217 Da. Calc. 379.121331 Da, dev. 1 ppm N-{3'-[5-((R)-1-Hydroxy-ethyl)-benzoimidazol-1-yl]-biphenyl-2-yl}-methanesulfonamide 9aaa: LC-ESI-HRMS of [M+H]+ shows 408.1377 Da. Calc. 408.138188 Da, dev. −1.2 ppm 1-(2'-Methoxy-biphenyl-3-yl)-1H-benzoimidazole-5-carboxylic acid amide 9aab:
LC-ESI-HRMS of [M+H]+ shows 344.1396 Da. Calc. 344.139902 Da, dev. −0.9 ppm 3'-[5-(1-Hydroxy-1-methyl-ethyl)-benzoimidazol-1-yl]-biphenyl-2-carbonitrile 9aac:
LC-ESI-HRMS of [M+H]+ shows 354.162 Da. Calc 354.160637 Da, dev. 3.8 ppm 2-[1-(2'-Methoxy-biphenyl-3-yl)-1H-benzoimidazol-5-yl]-propan-2-ol 9aad: LC-ESI-HRMS of [M+H]+ shows 359.1757 Da. Calc. 359.175953 Da, dev. −0.7 ppm (S)-1-[1-(5'-Chloro-2'-methoxy-biphenyl-3-yl)-1H-benzoimidazol-5-yl]-ethanol 9aae: LC-ESI-HRMS of [M+H]+ shows 379.1212 Da. Calc. 379.121331 Da, dev. −0.3 ppm N-{3'-[5-((S)-1-Hydroxy-ethyl)-benzoimidazol-1-yl]-biphenyl-2-yl}-methanesulfonamide 9aaf: LC-ESI-HRMS of [M+H]+ shows 408.1372 Da. Calc. 408.138188 Da, dev. −2.4 ppm (S)-1-[1-(2'-Methoxy-biphenyl-3-yl)-1H-benzoimidazol-5-yl]-ethanol 9aag: LC-ESI-HRMS of [M+H]+ shows 345.1604 Da. Calc. 345.160303 Da, dev. 0.3 ppm 3'-[5-((S)-1-Hydroxy-ethyl)-benzoimidazol-1-yl]-biphenyl-2-carboxylic acid amide 9aah: LC-ESI-HRMS of [M+H]+ shows 358.1545 Da. Calc. 358.155552 Da, dev. −2.9 ppm 2-[1-(5'-Chloro-2'-methoxy-biphenyl-3-yl)-1H-benzoimidazol-5-yl]-propan-2-ol 9aai: LC-ESI-HRMS of [M+H]+ shows 393.1373 Da. Calc. 393.136981 Da, dev. 0.8 ppm 1-(5'-Fluoro-2'-methoxy-biphenyl-3-yl)-1H-benzoimidazole-5-carboxylic acid amide 9aaj: LC-ESI-HRMS of [M+H]+ shows 362.1299 Da. Calc. 362.13048 Da, dev. −1.6 ppm 1-(5'-Chloro-2-methoxy-biphenyl-3-yl)-1H-benzoimidazole-5-carboxylic acid amide 9aak: LC-ESI-HRMS of [M+H]+ shows 378.1022 Da. Calc. 378.10093 Da, dev. 3.4 ppm (R)-1-[1-(2',6'-Dimethoxy-biphenyl-3-yl)-1H-benzoimidazol-5-yl]-ethanol 9aal: LC-ESI-HRMS of [M+H]+ shows 375.1709 Da. Calc. 375.170868 Da, dev. 0.1 ppm 1-(2'-Fluoro-6'-methoxy-biphenyl-3-yl)-1H-benzoimidazole-5-carboxylic acid amide 9aam: LC-ESI-HRMS of [M+H]+ shows 362.1306 Da. Calc. 362.13048 Da, dev. 0.3 ppm 1-(6'-Chloro-2'-methoxy-biphenyl-3-yl)-1H-benzoimidazole-5-carboxylic acid amide 9aan: LC-ESI-HRMS of [M+H]+ shows 378.0999 Da. Calc. 378.10093 Da, dev. −2.7 ppm 2-[1-(3'-Fluoro-2'-methoxy-biphenyl-3-yl)-1H-benzoimidazol-5-yl]-propan-2-ol 9aao: LC-ESI-HRMS of [M+H]+ shows 377.1675 Da. Calc. 377.166531 Da, dev. 2.6 ppm (R)-1-[1-(3'-Fluoro-2'-methoxy-biphenyl-3-yl)-1H-benzoimidazol-5-yl]-ethanol 9aap: LC-ESI-HRMS of [M+H]+ shows 363.149 Da. Calc. 363.150881 Da, dev. −5.2 ppm 2-[1-(2',3'-Dimethoxy-biphenyl-3-yl)-1H-benzoimidazol-5-yl]-propan-2-ol 9aaq: LC-ESI-HRMS of [M+H]+ shows 389.1849 Da. Calc. 389.186518 Da, dev. −4.2 ppm (R)-1-[1-(6'-Fluoro-2'-methoxy-biphenyl-3-yl)-1H-benzoimidazol-5-yl]-ethanol 9aar: LC-ESI-HRMS of [M+H]+ shows 363.1507 Da. Calc. 363.150881 Da, dev. −0.5 ppm (R)-1-[1-(2',3'-Dimethoxy-biphenyl-3-yl)-1H-benzoimidazol-5-yl]-ethanol 9aas: LC-ESI-HRMS of [M+H]+ shows 375.1718 Da. Calc. 375.170868 Da, dev. 2.5 ppm (R)-1-[1-(2',4'-Dimethoxy-biphenyl-3-yl)-1H-benzoimidazol-5-yl]-ethanol 9aat: LC-ESI-HRMS of [M+H]+ shows 375.1697 Da. Calc. 375.170868 Da, dev. −3.1 ppm 3-Chloro-3'-[5-(1-hydroxy-1-methyl-ethyl)-benzoimidazol-1-yl]-biphenyl-2-ol 9aau:
LC-ESI-HRMS of [M+H]+ shows 379.1219 Da. Calc. 379.121331 Da, dev. 1.5 ppm 2-[1-(2',6'-Dimethoxy-biphenyl-3-yl)-1H-benzoimidazol-5-yl]-propan-2-ol 9aav: LC-ESI-HRMS of [M+H]+ shows 389.1859 Da. Calc. 389.186518 Da, dev. −1.6 ppm (R)-1-[1-(6'-Chloro-2'-methoxy-biphenyl-3-yl)-1H-benzoimidazol-5-yl]-ethanol 9aax: LC-ESI-HRMS of [M+H]+ shows 379.1206 Da. Calc. 379.121331 Da, dev. −1.9 ppm 2-[1-(2',4'-Dimethoxy-biphenyl-3-yl)-1H-benzoimidazol-5-yl]-propan-2-ol 9aay: LC-ESI-HRMS of [M+H]+ shows 389.1866 Da. Calc. 389.186518 Da, dev. 0.2 ppm 2-[1-(6'-Fluoro-2'-methoxy-biphenyl-3-yl)-1H-benzoimidazol-5-yl]-propan-2-ol 9aaz: LC-ESI-HRMS of [M+H]+ shows 377.167 Da. Calc. 377.166531 Da, dev. 1.2 ppm (R)-1-{1-[3-(2-Fluoro-pyridin-3-yl)-phenyl]-1H-benzoimidazol-5-yl}-ethanol 9aba. LC-ESI-HRMS of [M+H]+ shows 334.1354 Da. Calc. 334.135565 Da, dev. −0.5 ppm (S)-1-{1-[3-(2-Fluoro-pyridin-3-yl)-phenyl]-1H-benzoimidazol-5-yl}-ethanol 9aca.
LC-ESI-HRMS of [M+H]+ shows 334.1359 Da. Calc. 334.135565 Da, dev. 1 ppm 2-{1-[3-(2-Fluoro-pyridin-3-yl)-phenyl]-1H-benzoimidazol-5-yl}-propan-2-ol 9ada.
LC-ESI-HRMS of [M+H]+ shows 348.1519 Da. Calc. 348.151215 Da, dev. 2 ppm 1-(2',6'-Dimethoxy-biphenyl-3-yl)-1H-benzoimidazole-5-carbonitrile 9aea.
1-(3'-Fluoro-2'-methoxy-biphenyl-3-yl)-1H-benzoimidazole-5-carbonitrile 9afa.
1-(6'-Fluoro-2'-methoxy-biphenyl-3-yl)-1H-benzoimidazole-5-carbonitrile 9aga.
1-(6'-Chloro-2'-methoxy-biphenyl-3-yl)-1H-benzoimidazole-5-carbonitrile 9aha.
1-(2'-Chloro-6'-fluoro-3'-methyl-biphenyl-3-yl)-1H-benzoimidazole-5-carbonitrile 9aia.
1-(2'-Chloro-6'-fluoro-5'-methyl-biphenyl-3-yl)-1H-benzoimidazole-5-carbonitrile 9aja.
1-(2',4'-Dimethoxy-biphenyl-3-yl)-1H-benzoimidazole-5-carbonitrile 9aka.

1-(2',3'-Dimethoxy-biphenyl-3-yl)-1H-benzoimidazole-5-carbonitrile 9ala.
1-[3-(5-Bromo-2-fluoro-pyridin-3-yl)-phenyl]-1H-benzoimidazole-5-carbonitrile 9ama.
1-[3-(2-Bromo-5-fluoro-pyridin-4-yl)-phenyl]-1H-benzoimidazole-5-carbonitrile 9ana.
1-(2',6'-Difluoro-biphenyl-3-yl)-1H-benzoimidazole-5-carbonitrile 9aoa.
1-(2',6'-Dichloro-biphenyl-3-yl)-1H-benzoimidazole-5-carbonitrile 9apa.
1-(2'-Piperazin-1-yl-biphenyl-3-yl)-1H-benzoimidazole-5-carbonitrile 9aqa. The compound is synthesized via the N-Boc-piperazine intermediate which is then deprotected.
1-[3-(2-Bromo-5-methoxy-pyridin-4-yl)-phenyl]-1H-benzoimidazole-5-carbonitrile 9ara.
1-[3-(2-Chloro-3-fluoro-pyridin-4-yl)-phenyl]-1H-benzoimidazole-5-carbonitrile 9asa.
1-(2',3'-Difluoro-6'-methoxy-biphenyl-3-yl)-1H-benzoimidazole-5-carbonitrile 9ata.
1-(4'-Fluoro-2'-methoxy-biphenyl-3-yl)-1H-benzoimidazole-5-carbonitrile 9aua.
1-(2'-Chloro-5'-cyano-biphenyl-3-yl)-1H-benzoimidazole-5-carbonitrile 9ava.
1-(3'-Chloro-2'-hydroxy-biphenyl-3-yl)-1H-benzoimidazole-5-carbonitrile 9axa.
1-(3'-Chloro-2',6'-difluoro-biphenyl-3-yl)-1H-benzoimidazole-5-carbonitrile 9aya.
1-[3-(2,4-Dimethoxy-pyrimidin-5-yl)-phenyl]-1H-benzoimidazole-5-carbonitrile 9aza.
1-[3-(2,6-Difluoro-pyridin-3-yl)-phenyl]-1H-benzoimidazole-5-carbonitrile 9baa.
1-[3-(3-Fluoro-pyridin-4-yl)-phenyl]-1H-benzoimidazole-5-carbonitrile 9caa.
1-[3-(3-Chloro-pyridin-4-yl)-phenyl]-1H-benzoimidazole-5-carbonitrile 9daa.
1-[3-(2-Chloro-pyridin-3-yl)-phenyl]-1H-benzoimidazole-5-carbonitrile 9eaa.
1-(2'-Morpholin-4-ylmethyl-biphenyl-3-yl)-1H-benzoimidazole-5-carbonitrile 9faa.
1-(3',5'-Difluoro-2'-methoxy-biphenyl-3-yl)-1H-benzoimidazole-5-carbonitrile 9jaa.
N-[3'-(5-Cyano-benzoimidazol-1-yl)-biphenyl-2-yl]-methanesulfonamide 9kaa.
1-[3-(2-Fluoro-pyridin-3-yl)-phenyl]-1H-benzoimidazole-5-carbonitrile 9laa.
1-(5'-Chloro-2'-methoxy-biphenyl-3-yl)-1H-benzoimidazole-5-carbonitrile 9maa.
3'-(5-Cyano-benzoimidazol-1-yl)-biphenyl-2-carboxylic acid amide 9naa.
1-(2',6'-Dimethoxy-biphenyl-3-yl)-1H-benzoimidazole-5-carboxylic acid amide 9oaa.
1-(3'-Fluoro-2'-methoxy-biphenyl-3-yl)-1H-benzoimidazole-5-carboxylic acid amide 9paa.
1-(2'-Chloro-6'-fluoro-3'-methyl-biphenyl-3-yl)-1H-benzoimidazole-5-carboxylic acid amide 9qaa.
1-(6'-Chloro-2'-fluoro-3'-methyl-biphenyl-3-yl)-1H-benzoimidazole-5-carboxylic acid amide 9raa.
1-(2',4'-Dimethoxy-biphenyl-3-yl)-1H-benzoimidazole-5-carboxylic acid amide 9saa.
1-(2',3'-Dimethoxy-biphenyl-3-yl)-1H-benzoimidazole-5-carboxylic acid amide 9taa.
1-[3-(5-Bromo-2-fluoro-pyridin-3-yl)-phenyl]-1H-benzoimidazole-5-carboxylic acid amide 9uaa.
1-[3-(2-Bromo-5-fluoro-pyridin-4-yl)-phenyl]-1H-benzoimidazole-5-carboxylic acid amide 9vaa.
1-(2',6'-Difluoro-biphenyl-3-yl)-1H-benzoimidazole-5-carboxylic acid amide 9xaa.
1-(2',6'-Dichloro-biphenyl-3-yl)-1H-benzoimidazole-5-carboxylic acid amide 9yaa.
1-(2'-piperazin-1-yl-biphenyl-3-yl)-1H-benzoimidazole-5-carboxylic acid amide 9zaa. The compound is synthesized via the N-Boc-piperazine intermediate which is then deprotected.
1-[3-(2-Bromo-5-methoxy-pyridin-4-yl)-phenyl]-1H-benzoimidazole-5-carboxylic acid amide 9bba.
1-[3-(2-Chloro-3-fluoro-pyridin-4-yl)-phenyl]-1H-benzoimidazole-5-carboxylic acid amide 9bbb.
1-(2',3'-Difluoro-6'-methoxy-biphenyl-3-yl)-1H-benzoimidazole-5-carboxylic acid amide 9bbc.
1-(4'-Fluoro-2'-methoxy-biphenyl-3-yl)-1H-benzoimidazole-5-carboxylic acid amide 9bbd.
1-(2'-Chloro-5'-cyano-biphenyl-3-yl)-1H-benzoimidazole-5-carboxylic acid amide 9bbe.
1-(3'-Chloro-2'-hydroxy-biphenyl-3-yl)-1H-benzoimidazole-5-carboxylic acid amide 9bbf.
1-(3'-Chloro-2',6'-difluoro-biphenyl-3-yl)-1H-benzoimidazole-5-carboxylic acid amide 9bbg.
1-[3-(2,4-Dimethoxy-pyrimidin-5-yl)-phenyl]-1H-benzoimidazole-5-carboxylic acid amide 9bbh.
1-[3-(2,6-Difluoro-pyridin-3-yl)-phenyl]-1H-benzoimidazole-5-carboxylic acid amide 9bbi.
1-[3-(3-Fluoro-pyridin-4-yl)-phenyl]-1H-benzoimidazole-5-carboxylic acid amide 9bbj.
1-[3-(3-Chloro-pyridin-4-yl)-phenyl]-1H-benzoimidazole-5-carboxylic acid amide 9bbk.
1-[3-(2-Chloro-pyridin-3-yl)-phenyl]-1H-benzoimidazole-5-carboxylic acid amide 9bbl.
1-(2'-Morpholin-4-ylmethyl-biphenyl-3-yl)-1H-benzoimidazole-5-carboxylic acid amide 9bbm.
1-(3',5'-Difluoro-2'-methoxy-biphenyl-3-yl)-1H-benzoimidazole-5-carboxylic acid amide 9bbq.
1-(2'-Methanesulfonylamino-biphenyl-3-yl)-1H-benzoimidazole-5-carboxylic acid amide 9bbr.
1-[3-(2-Fluoro-pyridin-3-yl)-phenyl]-1H-benzoimidazole-5-carboxylic acid amide 9bbs.
1-(2'-Carbamoyl-biphenyl-3-yl)-1H-benzoimidazole-5-carboxylic acid amide 9bbt.
(R)-1-[1-(2'-Chloro-6'-fluoro-3'-methyl-biphenyl-3-yl)-1H-benzoimidazol-5-yl]-ethanol 9bbu.
(R)-1-[1-(6'-Chloro-2'-fluoro-3'-methyl-biphenyl-3-yl)-1H-benzoimidazol-5-yl]-ethanol 9bbv.
(R)-1-{1-[3-(5-Bromo-2-fluoro-pyridin-3-yl)-phenyl]-1H-benzoimidazol-5-yl}-ethanol 9bbx.
(R)-1-{1-[3-(2-Bromo-5-fluoro-pyridin-4-yl)-phenyl]-1H-benzoimidazol-5-yl}-ethanol 9bby.
(R)-1-[1-(2',6'-Difluoro-biphenyl-3-yl)-1H-benzoimidazol-5-yl]-ethanol 9bbz.
(R)-1-[1-(2',6'-Dichloro-biphenyl-3-yl)-1H-benzoimidazol-5-yl]-ethanol 9 cca.
1-[1-((R)-2'-piperazin-1-yl-biphenyl-3-yl)-1H-benzoimidazol-5-yl]-ethanol 9 ccb. The compound is synthesized via the N-Boc-piperazine intermediate which is then deprotected.
(R)-1-(1-[3-(2-Bromo-5-methoxy-pyridin-4-yl)-phenyl]-1H-benzoimidazol-5-yl)-ethanol 9 ccc.
(R)-1-{1-[3-(2-Chloro-3-fluoro-pyridin-4-yl)-phenyl]-1H-benzoimidazol-5-yl}-ethanol 9 ccd.
(R)-1-[1-(2',3'-Difluoro-6'-methoxy-biphenyl-3-yl)-1H-benzoimidazol-5-yl]-ethanol 9 cce.
(R)-1-[1-(4'-Fluoro-2'-methoxy-biphenyl-3-yl)-1H-benzoimidazol-5-yl]-ethanol 9 ccf.
6-Chloro-3'-[5-((R)-1-hydroxy-ethyl)-benzoimidazol-1-yl]-biphenyl-3-carbonitrile 9ccg.
3-Chloro-3'-[5-((R)-1-hydroxy-ethyl)-benzoimidazol-1-yl]-biphenyl-2-ol 9 cch.
(R)-1-[1-(3'-Chloro-2',6'-difluoro-biphenyl-3-yl)-1H-benzoimidazol-5-yl]-ethanol 9 cci.

(R)-1-{1-[3-(2,4-Dimethoxy-pyrimidin-5-yl)-phenyl]-1H-benzoimidazol-5-yl}-ethanol 9 ccj.
(R)-1-{1-[3-(2,6-Difluoro-pyridin-3-yl)-phenyl]-1H-benzoimidazol-5-yl}-ethanol 9cck.
(R)-1-{1-[3-(3-Fluoro-pyridin-4-yl)-phenyl]-1H-benzoimidazol-5-yl}-ethanol 9 ccl.
(R)-1-{1-[3-(3-Chloro-pyridin-4-yl)-phenyl]-1H-benzoimidazol-5-yl}-ethanol 9 ccm.
(R)-1-{1-[3-(2-Chloro-pyridin-3-yl)-phenyl]-1H-benzoimidazol-5-yl}-ethanol 9 ccn.
(R)-1-[1-(2'-Morpholin-4-ylmethyl-biphenyl-3-yl)-1H-benzoimidazol-5-yl]-ethanol 9 cco.
(R)-1-[1-(3',5'-Difluoro-2'-methoxy-biphenyl-3-yl)-1H-benzoimidazol-5-yl]-ethanol 9ccs.
(S)-1-[1-(2',6'-Dimethoxy-biphenyl-3-yl)-1H-benzoimidazol-5-yl]-ethanol 9 cct.
(S)-1-[1-(3'-Fluoro-2'-methoxy-biphenyl-3-yl)-1H-benzoimidazol-5-yl]-ethanol 9 ccu.
(S)-1-[1-(6'-Fluoro-2'-methoxy-biphenyl-3-yl)-1H-benzoimidazol-5-yl]-ethanol 9 ccv.
(S)-1-[1-(2',3'-Dimethoxy-biphenyl-3-yl)-1H-benzoimidazol-5-yl]-ethanol 9 ccx.
(S)-1-[1-(2',4'-Dimethoxy-biphenyl-3-yl)-1H-benzoimidazol-5-yl]-ethanol 9 ccy.
(S)-1-[1-(6'-Chloro-2'-methoxy-biphenyl-3-yl)-1H-benzoimidazol-5-yl]-ethanol 9ccz.
(S)-1-[1-(2'-Chloro-6'-fluoro-3'-methyl-biphenyl-3-yl)-1H-benzoimidazol-5-yl]-ethanol 9dda.
(S)-1-[1-(6'-Chloro-2'-fluoro-3'-methyl-biphenyl-3-yl)-1H-benzoimidazol-5-yl]-ethanol 9ddb.
(S)-1-{1-[3-(5-Bromo-2-fluoro-pyridin-3-yl)-phenyl]-1H-benzoimidazol-5-yl}-ethanol 9ddc.
(S)-1-{1-[3-(2-Bromo-5-fluoro-pyridin-4-yl)-phenyl]-1H-benzoimidazol-5-yl}-ethanol 9ddd.
(S)-1-[1-(2',6'-Difluoro-biphenyl-3-yl)-1H-benzoimidazol-5-yl]-ethanol 9dde.
(S)-1-[1-(2',6'-Dichloro-biphenyl-3-yl)-1H-benzoimidazol-5-yl]-ethanol 9ddf.
1-[1-((S)-2'-piperazin-1-yl-biphenyl-3-yl)-1H-benzoimidazol-5-yl]-ethanol 9ddg.
The compound is synthesized via the N-Boc-piperazine intermediate which is then deprotected.
(S)-1-{1-[3-(2-Bromo-5-methoxy-pyridin-4-yl)-phenyl]-1H-benzoimidazol-5-yl}-ethanol 9ddh.
(S)-1-{1-[3-(2-Chloro-3-fluoro-pyridin-4-yl)-phenyl]-1H-benzoimidazol-5-yl}-ethanol 9ddi.
(S)-1-[1-(2',3'-Difluoro-6'-methoxy-biphenyl-3-yl)-1H-benzoimidazol-5-yl]-ethanol 9ddj.
(S)-1-[1-(4'-Fluoro-2'-methoxy-biphenyl-3-yl)-1H-benzoimidazol-5-yl]-ethanol 9ddk.
6-Chloro-3'-[5-((S)-hydroxy-ethyl)-benzoimidazol-1-yl]-biphenyl-3-carbonitrile 9ddl.
3-Chloro-3'-[5-((S)-1-hydroxy-ethyl)-benzoimidazol-1-yl]-biphenyl-2-ol 9ddm.
(S)-1-[1-(3'-Chloro-2',6'-difluoro-biphenyl-3-yl)-1H-benzoimidazol-5-yl]-ethanol 9ddn.
(S)-1-{1-[3-(2,4-Dimethoxy-pyrimidin-5-yl)-phenyl]-1H-benzoimidazol-5-yl}-ethanol 9ddo.
(S)-1-{1-[3-(2,6-Difluoro-pyridin-3-yl)-phenyl]-1H-benzoimidazol-5-yl}-ethanol 9ddp.
(S)-1-{1-[3-(3-Fluoro-pyridin-4-yl)-phenyl]-1H-benzoimidazol-5-yl}-ethanol 9ddq.
(S)-1-{1-[3-(3-Chloro-pyridin-4-yl)-phenyl]-1H-benzoimidazol-5-yl}-ethanol 9ddr.
(8)-1-(1-[3-(2-Chloro-pyridin-3-yl)-phenyl]-1H-benzoimidazol-5-yl)-ethanol 9dds.
(S)-1-[1-(2'-Morpholin-4-ylmethyl-biphenyl-3-yl)-1H-benzoimidazol-5-yl]-ethanol 9ddt.
(S)-1-[1-(3',5'-Difluoro-2'-methoxy-biphenyl-3-yl)-1H-benzoimidazol-5-yl]-ethanol 9ddy.
2-[1-(6'-Chloro-2'-methoxy-biphenyl-3-yl)-1H-benzoimidazol-5-yl]-propan-2-ol 9ddz.
2-[1-(2'-Chloro-6'-fluoro-3'-methyl-biphenyl-3-yl)-1H-benzoimidazol-5-yl]-propan-2-ol 9eea.
2-[1-(6'-Chloro-2'-fluoro-3'-methyl-biphenyl-3-yl)-1H-benzoimidazol-5-yl]-propan-2-ol 9eeb.
2-{1-[3-(5-Bromo-2-fluoro-pyridin-3-yl)-phenyl]-1H-benzoimidazol-5-yl}-propan-2-ol 9eec.
2-{1-[3-(2-Bromo-5-fluoro-pyridin-4-yl)-phenyl]-1H-benzoimidazol-5-yl}-propan-2-ol 9eed.
2-[1-(2',6'-Difluoro-biphenyl-3-yl)-1H-benzoimidazol-5-yl]-propan-2-ol 9eee.
2-[1-(2',6'-Dichloro-biphenyl-3-yl)-1H-benzoimidazol-5-yl]-propan-2-ol 9eef.
2-[1-(2'-piperazin-1-yl-biphenyl-3-yl)-1H-benzoimidazol-5-yl]-propan-2-ol 9eeg.
The compound is synthesized via the N-Boc-piperazine intermediate which is then deprotected.
2-{1-[3-(2-Bromo-5-methoxy-pyridin-4-yl)-phenyl]-1H-benzoimidazol-5-yl}-propan-2-ol 9eeh.
2-{1-[3-(2-Chloro-3-fluoro-pyridin-4-yl)-phenyl]-1H-benzoimidazol-5-yl}-propan-2-ol 9eei.
2-[1-(2',3'-Difluoro-6'-methoxy-biphenyl-3-yl)-1H-benzoimidazol-5-yl]-propan-2-ol 9eej.
2-[1-(4'-Fluoro-2'-methoxy-biphenyl-3-yl)-1H-benzoimidazol-5-yl]-propan-2-ol 9eek.
6-Chloro-3'-[5-(1-hydroxy-1-methyl-ethyl)-benzoimidazol-1-yl]-biphenyl-3-carbonitrile 9eel.
2-[1-(3'-Chloro-2',6'-difluoro-biphenyl-3-yl)-1H-benzoimidazol-5-yl]-propan-2-ol 9eem.
2-{1-[3-(2,4-Dimethoxy-pyrimidin-5-yl)-phenyl]-1H-benzoimidazol-5-yl}-propan-2-ol 9een.
LC-ESI-HRMS of [M+H]+ shows 391.1763 Da. Calc. 391.177016 Da, dev. −1.8 ppm
2-{1-[3-(2,6-Difluoro-pyridin-3-yl)-phenyl]-1H-benzoimidazol-5-yl}-propan-2-ol 9eeo.
LC-ESI-HRMS of [M+H]+ shows 366.1417 Da. Calc. 366.141793 Da, dev. −0.3 ppm
2-{1-[3-(3-Fluoro-pyridin-4-yl)-phenyl]-1H-benzoimidazol-5-yl}-propan-2-ol 9eep.
2-{1-[3-(3-Chloro-pyridin-4-yl)-phenyl]-1H-benzoimidazol-5-yl}-propan-2-ol 9eeq.
2-{1-[3-(2-Chloro-pyridin-3-yl)-phenyl]-1H-benzoimidazol-5-yl}-propan-2-ol 9eer.
2-[1-(2'-Morpholin-4-ylmethyl-biphenyl-3-yl)-1H-benzoimidazol-5-yl]-propan-2-ol 9ees.
2-[1-(3',5'-Difluoro-2'-methoxy-biphenyl-3-yl)-1H-benzoimidazol-5-yl]-propan-2-ol 9eex.
LC-ESI-HRMS of [M+H]+ shows 395.1587 Da. Calc. 395.157109 Da, dev. 4 ppm
3'-[5-(1-Hydroxy-1-methyl-ethyl)-benzoimidazol-1-yl]-biphenyl-2-carboxylic acid amide 9eey.
N-{3'-[5-(1-Hydroxy-1-methyl-ethyl)-benzoimidazol-1-yl]-biphenyl-2-yl}-methanesulfonamide 9eez.
2-[1-(5'-Fluoro-2'-methoxy-biphenyl-3-yl)-1H-benzoimidazol-5-yl]-propan-2-ol 9ffa.
LC-ESI-HRMS of [M+H]+ shows 377.1678 Da. Calc. 377.166531 Da, dev. 3.4 ppm
1-[1-(5'-Chloro-2'-methoxy-biphenyl-3-yl)-1H-benzoimidazol-5-yl]-ethanone 9ffb.

Example 3

Synthesis of Oximes 11a-k

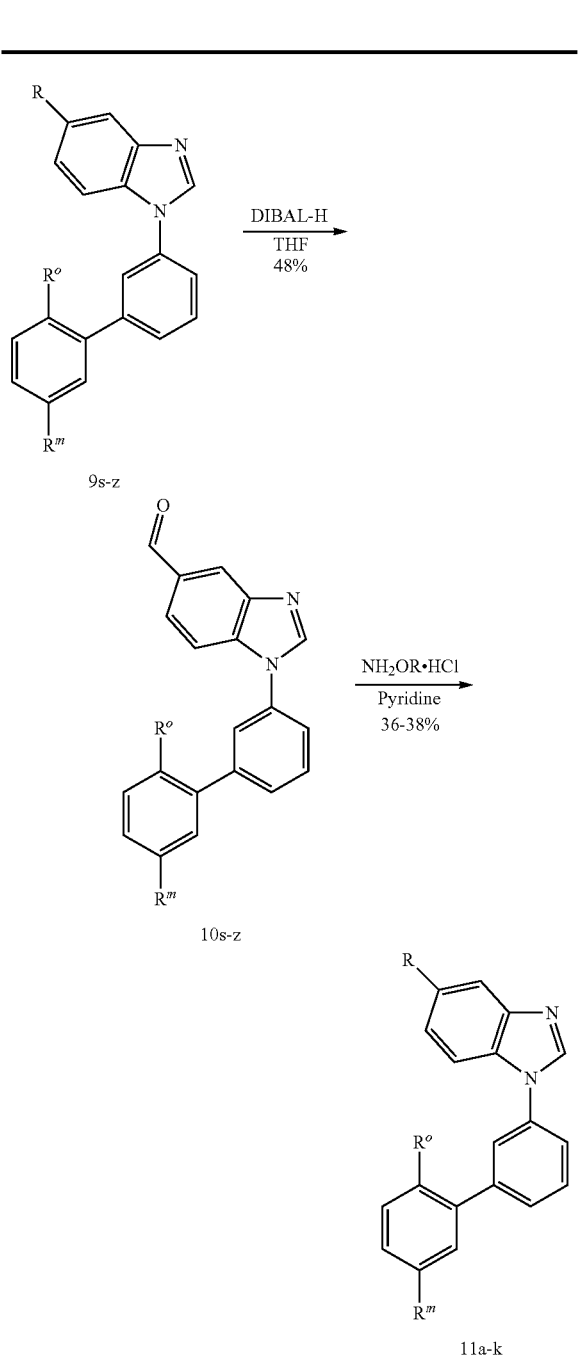

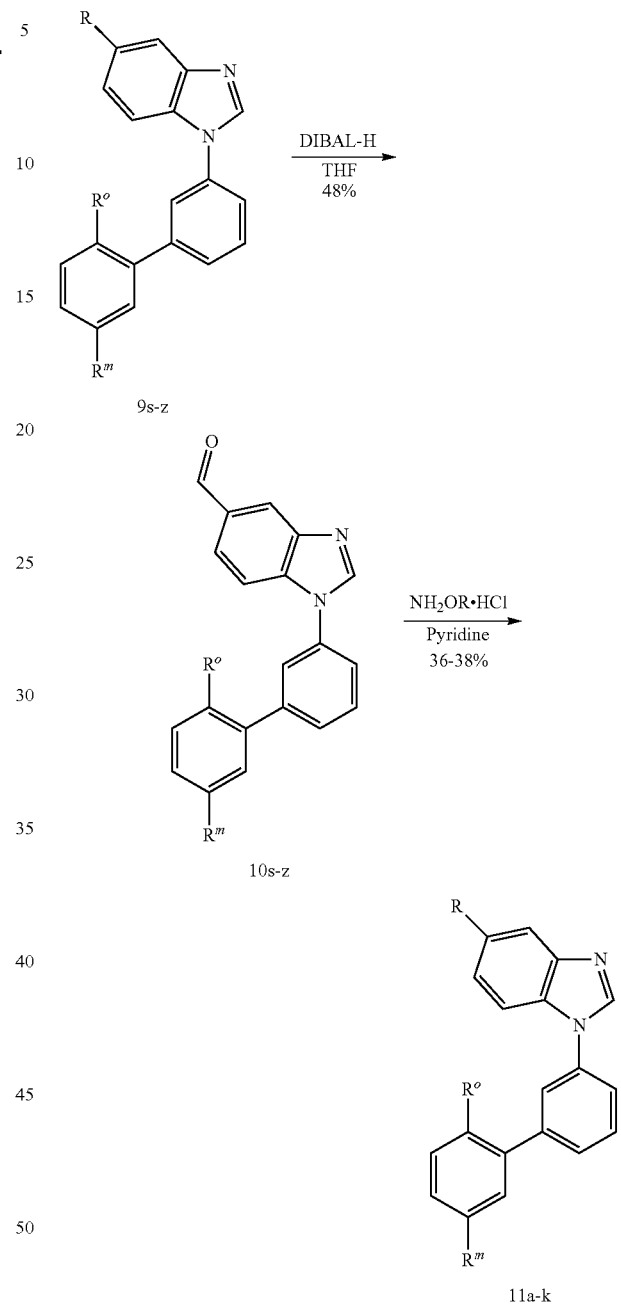

| Cmpd No. | Starting material | R' | R | R$^o$ | R$^m$ |
|---|---|---|---|---|---|
| 11a | 9z | CN | HC(=NOH) | Et | H |
| 11b | 9y | CN | HC(=NOH) | Me | H |
| 11c | 9x | CN | HC(=NOH) | OEt | H |
| 11d | 9y | CN | HC(=NOMe) | Me | H |
| 11e | 9x | CN | HC(=NOMe) | OEt | H |
| 11f | 9v | CN | HC(=NOMe) | OiPr | H |
| 11g | 9v | CN | HC(=NOH) | OiPr | H |
| 11h | 9s | CN | HC(=NOMe) | OMe | H |
| 11i | 9s | CN | HC(=NOH) | OMe | H |
| 11j | 9t | CN | HC(=NOMe) | CN | H |
| 11k | 9t | CN | HC(=NOH) | CN | H |
| 11l | 9c | CF$_3$ | — | C(=NOH)Me | H |
| 11m | 9c | CF$_3$ | — | C(=NOMe)Me | H |
| 11n | 9r | Acetyl | C(=NOMe)Me | CN | H |
| 11o | 9r | Acetyl | C(=NOH)Me | CN | H |

*For 11l and 11k no DIBAL reduction was necessary.

Example of DIBAL Reduction of CN Group 1-(2'-Methyl-biphenyl-3-yl)-1H-benzoimidazole-5-carbaldehyde 10v To a solution of 9v (510 mg, 1.64 mmol) in dry THF (10 mL) at −78° C. was added solution of DIBAL-H (5.5 mL 1.8 M in toluene, 9.9 mmol) and allowed to come to −40° C. while stirring for 2 h. The reaction mixture was quenched with MeOH (0.5 mL), diluted with chloroform (50 mL) and Rochelle salt solution while stirring for 3 h. The organic layer was separated, washed with brine, dried over $Na_2SO_4$ and concentrated to give aldehyde 10v (250 mg, 48%) as pale yellow solid and it was taken as such for the next step without purification.

Example of Oxime Formation

In a solution of compound 10v (125 mg, 0.40 mmol) in ethanol (6 mL) at 0° C. was added pyridine (48 mg, 0.60 mmol) and hydroxylamine hydrochloride (33 mg, 0.48 mmol) while stirring for 3 h. After concentration, ice cold water was added and the resulting white precipitate was filtered, washed with dry diethyl ether and dried under high vacuum to furnish oxime 11g (50 mg, 38%) as white solid, MP-222.2-224.9° C.

Example of O-Methyl-oxime Formation

To a solution of compound 10v (125 mg, 0.40 mmol) in ethanol (6 mL) at 0° C. was added pyridine (48 mg, 0.60 mmol) and methoxylamine hydrochloride (39 mg, 0.48 mmol) and allowed to come to RT while stirring for 4 h. The reaction mixture was concentrated and purified by column chromatography using 20% ethylacetate in hexane to afford oxime ether 11f (50 mg, 36%) as white solid, MP-108.3-110.9° C.

The following compounds were prepared using the same conditions as mentioned above:
1-(2'-Ethyl-biphenyl-3-yl-1H-benzoimidazole-5-carbaldehyde oxime 11a: White solid. MP 224-230° C.
1-(2'-Methyl-biphenyl-3-yl)-1H-benzoimidazole-5-carbaldehyde oxime 11b: LC-ESI-HRMS of [M+H]+ shows 328.1434 Da. Calc. 328.144987 Da, dev. −4.8 ppm
1-(2'-Ethoxy-biphenyl-3-yl)-1H-benzoimidazole-5-carbaldehyde oxime 11c: LC-ESI-HRMS of [M+H]+ shows 358.156 Da. Calc. 358.155552 Da, dev. 1.3 ppm
1-(2'-Methyl-biphenyl-3-yl)-1H-benzoimidazole-5-carbaldehyde O-methyl-oxime 11d: LC-ESI-HRMS of [M+H]+ shows 342.1595 Da. Calc. 342.160637 Da, dev. −3.3 ppm
1-(2'-Ethoxy-biphenyl-3-yl)-1H-benzoimidazole-5-carbaldehyde O-methyl-oxime 11e: LC-ESI-HRMS of [M+H]+ shows 372.1729 Da. Calc. 372.171202 Da, dev. 4.6 ppm
1-(2'-Isopropoxy-biphenyl-3-yl)-1H-benzoimidazole-5-carbaldehyde O-methyl-oxime 11f: LC-ESI-HRMS of [M+H]+ shows 386.1878 Da. Calc. 386.186852 Da, dev. 2.5 ppm
1-(2'-Isopropoxy-biphenyl-3-yl)-1H-benzoimidazole-5-carbaldehyde oxime 11g:
LC-ESI-HRMS of [M+H]+ shows 372.1709 Da. Calc. 372.171202 Da, dev. −0.8 ppm
1-(2'-Methoxy-biphenyl-3-yl)-1H-benzoimidazole-5-carbaldehyde O-methyl-oxime 11h: LC-ESI-HRMS of [M+H]+ shows 358.156 Da. Calc. 358.155552 Da, dev. 1.3 ppm
1-(2'-Methoxy-biphenyl-3-yl)-1H-benzoimidazole-5-carbaldehyde oxime 11i: LC-ESI-HRMS of [M+H]+ shows 357.1226 Da. Calc. 357.123918 Da, dev. −3.7 ppm
1-(2'-Cyano-biphenyl-3-yl)-1H-benzoimidazole-5-carbaldehyde O-methyl-oxime 11j: LC-ESI-HRMS of [M+H]+ shows 353.1393 Da. Calc. 353.140236 Da, dev. −2.7 ppm
1-(2'-Cyano-biphenyl-3-yl)-1H-benzoimidazole-5-carbaldehyde oxime 11k: LC-ESI-HRMS of [M+H]+ shows 339.1229 Da. Calc. 339.124586 Da, dev. −5 ppm
1-[3'-(5-Trifluoromethyl-benzoimidazol-1-yl)-biphenyl-2-yl]-ethanone oxime 11l:
LC-ESI-HRMS of [M+H]+ shows 396.1324 Da. Calc. 396.132371 Da, dev. 0.1 ppm
1-[3'-(5-Trifluoromethyl-benzoimidazol-1-yl)-biphenyl-2-yl]-ethanone O-methyl-oxime 11m: LC-ESI-HRMS of [M+H]+ shows 410.1483 Da. Calc. 410.148021 Da, dev. 0.7 ppm
1-(2'-Cyano-biphenyl-3-yl)-1H-benzoimidazole-5-acetyl O-methyl-oxime 11n: LC-ESI-HRMS of [M+H]+ shows 367.154 Da. Calc. 367.155886 Da, dev. −5.1 ppm
1-(2'-Cyano-biphenyl-3-yl)-1H-benzoimidazole-5-acetyl oxime 11o: LC-ESI-HRMS of [M+H]+ shows 353.1402 Da. Calc. 353.140236 Da, dev. −0.1 ppm

Example 4

Synthesis of Further Novel Compounds

The following compounds were prepared from compounds that were synthesized in the above examples. The detailed synthesis is described below.

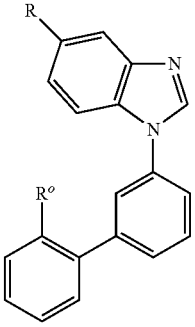

| Cmpd No. | Starting Material | R | R° |
|---|---|---|---|
| 12a | 9c | $CF_3$ | 3-pyrazolyl |
| 12b | 9c | $CF_3$ | 5-isoxazolyl |
| 12c | 9c | $CF_3$ | CH(OH)Me |
| 12d | 12c | $CF_3$ | CH(OEt)Me |
| 12e | 9aj | 3-pyrazolyl | CH(OH)Me |
| 12f | 9aj | 3-pyrazolyl | 3-prazolyl |
| 12g | 9aj | 3-pyrazolyl | 5-isoxazolyl |
| 12h | 9s | C(=NH)NHOH | OMe |
| 12i | 9ar | 2-(4,5-dihydro)-imidazolyl | OMe |

-continued

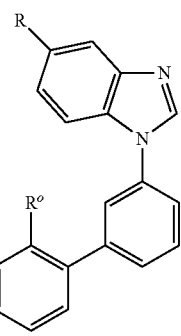

| Cmpd No. | Starting Material | R | R° |
|---|---|---|---|
| 12j | 9ar | CH(OH)CN | OMe |
| 12k | 9ar | CH(OH)C≡CH | OMe |

Synthesis of Compounds 12c-e
General Procedure for the NaBH$_4$ Reduction of Ketones:

9c or 9aj (1 eq) were dissolved in MeOH (100 ml) and NaBH$_4$ (1 eq) wad added portion wise. The reaction was followed by LCMS and when finished it was quenched with H$_2$O. Extraction with EtOAc, dried with MgSO$_4$ and evaporated to give the crude product. Column chromatography (5% MeOH in DCM) gave the pure compound 12c and 12e, respectively.

5-Trifluoromethyl-1-(2'-(1-hydroxyethyl)-biphenyl-3-yl)-1H-benzoimidazole 12c:
LC-ESI-HRMS of [M+H]+ shows 405.1342 Da. Calc. 405.132705 Da, dev. 3.7 ppm 5-(1H-3-Pyrazolyl)-1-(2'-(1-hydroxyethyl)-biphenyl-3-yl)-1H-benzoimidazole 12e:
LC-ESI-HRMS of [M+H]+ shows 381.1721 Da. Calc. 381.171536 Da, dev. 1.5 ppm 5-Trifluoromethyl-1-(2'-(1-ethoxyethyl)-biphenyl-3-yl)-1H-benzoimidazole 12d
To a solution of 12c (0.88 g, 0.23 mmol) in dry DMF (10 ml) was added NaH (0.23 mmol) and the reaction was stirred for 1 h after which Iodoethane (2.8 mmol) was added. Stirring was maintained overnight. LCMS showed 70% product and the reaction was worked up by pouring into water. Extraction with EtOAc and subsequently column chromatography 5% MeOH/CH$_2$Cl$_2$ afforded the product in 60% yield: LC-ESI-HRMS of [M+H]+ shows 411.1698 Da. Calc. 411.168422 Da, dev. 3.4 ppm Synthesis of Compounds 12a, 12b, 12f and 12g
To a solution of 9c or 9aj (1 eq) in 70 ml DMF was added Dimethylformamide dimethylacetal (2 eq) and the mixture was stirred at 120° C. overnight and the reaction followed by LCMS. The reaction was stopped by pouring into ice/water and the resulting precipitate was filtered off and dried under vacuum to give the product which was used directly in the next step.

Synthesis of Isoxazoles
The above prepared Michael acceptor (1 eq) was dissolved in 50 ml MeOH and heated to reflux. To this hydroxylamine hydrochloride (2 eq) was added and the reaction monitored by LCMS. After 30 min no traces of starting material was seen and the MeOH was removed in vacuo. The resulting solid was washed thoroughly with H$_2$O and Na$_2$CO$_3$ aq and then dried in a vacuum oven to give the product.

5-Trifluoromethyl-1-(2'-(5-isoxazolyl)-biphenyl-3-yl)-1H-benzoimidazole 12b: LC-ESI-HRMS of [M+H]+ shows 406.1163 Da. Calc. 406.116721 Da, dev. −1 ppm 5-(1H-3-Pyrazolyl)-1-(2'-(5-isoxazolyl)-biphenyl-3-yl)-1H-benzoimidazole 12g: LC-ESI-HRMS of [M+H]+ shows 404.1516 Da. Calc. 404.151135 Da, dev. 1.2 ppm Synthesis of Pyrazoles
The above prepared Michael acceptor (1 eq) was dissolved in 100 ml Ethanol (99%) and hydrazine monohydrate (4 eq) was added. The mixture was stirred overnight at room temperature. A brownish precipitate was observed and the reaction mixture was diluted with H$_2$O and the precipitate was filtered off. The resulting product was dried in a vacuum oven to give the product.

5-Trifluoromethyl-1-(2'-(1H-3-pyrazolyl)-biphenyl-3-yl)-1H-benzoimidazole 12a:
LC-ESI-HRMS of [M+H]+ shows 405.1342 Da. Calc. 405.132705 Da, dev. 3.7 ppm 5-(1H-3-Pyrazolyl)-1-(2'-(1H-3-pyrazolyl)-biphenyl-3-yl)-1H-benzoimidazole 12f:
LC-ESI-HRMS of [M+H]+ shows 403.1653 Da. Calc. 403.167119 Da, dev. −4.5 ppm 5-(4,5-Dihydro-1H-imidazol-2-yl)-1-(2'-methoxy-biphenyl-3-yl)-1H-benzoimidazole 12i:
To a solution of compound 9ar (50 mg, 0.15 mmol) in CH$_2$Cl$_2$ (1.5 mL) at 0° C. was added ethylenediamine (100 μL, 0.15 mmol) and stirred for 30 min. Reaction was monitored by $^1$H NMR, as R$_f$ of both starting material and product became identical at TLC. Then NBS (28 mg, 0.157 mmol) was added and stirred for 12 h at RT. The reaction mixture was worked up with ethylacetate and 10% NaOH solution. The organic layer was washed with brine, dried over Na$_2$SO$_4$ and concentrated. The crude mass was purified by silica gel column chromatography using 30% ethylacetate in hexane as eluent to furnish 12i (25 mg, 44%) as brown solid, MP 220.6-223.8° C. LC-ESI-HRMS of [M+H]+ shows 369.1696 Da. Calc. 369.171536 Da, dev. −5.2 ppm 5-(Cyano-hydroxy-methyl)-1-(2'-methoxy-biphenyl-3-yl)-1H-benzoimidazole 12j
To the solution of 9 as (0.25 g, 0.76 mmol) and Trimethylsilyl cyanide (0.3 ml, 2.28 mmol) in DCM (5 ml) was added ytterbium(III)trifluoromethanesulphonate (0.04 g, 0.076 mmol) at 0° C. and reaction mixture was allowed to warm to rt and was stirred at the same temperature. After stirring for 2 h, all the starting material was consumed and gave a major nonpolar spot which was the -OTMS compound. It was worked up in water/chloroform system and to deprotect the -TMS group the crude material was taken in DCM and 1 N aq HCl was added and stirred for 12 h. After the cleaving of -TMS group to the resultant reaction mixture, sodium bicarbonate solution was added and at neutral pH it was extracted in to DCM layer. The organic layer was washed with water followed by brine, evaporated under vacuum to give the pure product, MP 116.5-123.6° C.

5-(1-Hydroxy-prop-2-ynyl)-1-(2'-methoxy-biphenyl-3-yl)-1H-benzoimidazole 12k:
To the solution of 9 as (0.25 g, 0.76 mmol) in THF (20 ml) at 0° C., Ethynylmagnesium bromide (4.5 ml (0.5 M)) was added dropwise and reaction mixture stirred at rt for 3 hours. Reaction was monitored by TLC. After the completion of reaction, the excess grignard reagent was quenched with saturated ammonium chloride solution and product extracted with chloroform. The crude was purified through column using 1% methanol in chloroform as eluent. LC-ESI-HRMS of [M+H]+ shows 355.1456 Da. Calc. 355.144653 Da, dev. 2.7 ppm 5-(N-Hydroxy-carboxamidinyl)-1-(2'-methoxy-biphenyl-3-yl)-1H-benzoimidazole 12h:
To the solution of 9s (0.2 g, 0.61 mmol) in EtOH (10 ml), hydroxylamine hydrochloride (0.07 g, 0.98 mmol) and 2M aq sodium carbonate (1 eq.) were added and the reaction mixture was stirred at 75° C. for 16 hrs. Ethanol was concentrated, and material was taken for purification by column chromatography by using 25% Ethyl acetate in Pet ether. LC-ESI-HRMS of [M+H]+ shows 359.1499 Da. Calc. 359.150801 Da, dev. −2.5 ppm Analogously to compound 12h, the compounds 12ha-12han in the below Table were or are prepared:

1-(2'-Chloro-biphenyl-3-yl)-N-hydroxy-1H-benzoimidazole-5-carboxamidine 12ha:

LC-ESI-HRMS of [M+H]+ shows 363.101 Da. Calc. 363.101264 Da, dev. −0.7 ppm

N-Hydroxy-1-(2'-isopropoxy-biphenyl-3-yl)-1H-benzoimidazole-5-carboxamidine 12hb.

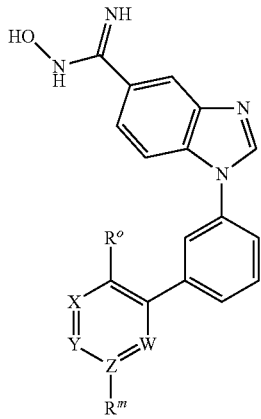

| No. | Starting Material | X | Y | Z | W | $R^o$ | $R^m$ |
|---|---|---|---|---|---|---|---|
| 12ha | 9u | C | C | C | C | Cl | H |
| 12hb | 9v | C | C | C | C | OiPr | H |
| 12hc | 9x | C | C | C | C | OEt | H |
| 12hd | 9y | C | C | C | C | Me | H |
| 12he | 9z | C | C | C | C | Et | H |
| 12hf | 9aa | C | C | C | C | OMe | F |
| 12hg | 9aea | C | C | C | C—OMe | OMe | H |
| 12hh | 9afa | C—F | C | C | C | OMe | H |
| 12hi | 9aga | C | C | C | C—F | OMe | H |
| 12hj | 9aha | C | C | C | C—Cl | OMe | H |
| 12hk | 9aia | C—Me | C | C | C—F | Cl | H |
| 12hl | 9aja | C | C | C | C—F | Cl | Me |
| 12hm | 9aka | C | C-OMe | C | C | OMe | H |
| 12hn | 9ala | C—OMe | C | C | C | OMe | H |
| 12ho | 9ama | N | C | C | C | F | Br |
| 12hp | 9ana | C | N | C | C | F | Br |
| 12hq | 9aoa | C | C | C | C—F | F | H |
| 12hr | 9apa | C | C | C | C—Cl | Cl | H |
| 12hs | 9aqa | C | C | C | C | Piperazin-1-yl | H |
| 12ht | 9ara | C | N | C | C | OMe | Br |
| 12hu | 9asa | C—Cl | N | C | C | F | H |
| 12hv | 9ata | C | C | C | C—F | OMe | F |
| 12hx | 9aua | C | C—F | C | C | OMe | H |
| 12hy | 9axa | C—Cl | C | C | C | OH | H |
| 12hz | 9aya | C—Cl | C | C | C—F | F | H |
| 12haa | 9aza | N | C—OMe | N | C | OMe | — |
| 12hab | 9baa | N | C—F | C | C | F | H |
| 12hac | 9caa | C | N | C | C | F | H |
| 12had | 9daa | C | N | C | C | Cl | H |
| 12hae | 9eaa | N | C | C | C | Cl | H |
| 12haf | 9faa | C | C | C | C | (4-Morfolinyl)-methyl | H |
| 12haj | 9jaa | C—F | C | C | C | OMe | F |
| 12hak | 9kaa | C | C | C | C | NHSO$_2$Me | H |
| 12hal | 9laa | N | C | C | C | F | H |
| 12ham | 9maa | C | C | C | C | OMe | Cl |
| 12han | 9naa | C | C | C | C | C(=O)NH$_2$ | H |

1-(2'-Ethoxy-biphenyl-3-yl)-N-hydroxy-1H-benzoimidazole-5-carboxamidine 12hc.
N-Hydroxy-1-(2'-methyl-biphenyl-3-yl)-1H-benzoimidazole-5-carboxamidine 12hd.
1-(2'-Ethyl-biphenyl-3-yl)-N-hydroxy-1H-benzoimidazole-5-carboxamidine 12he.
1-(5'-Fluoro-2'-methoxy-biphenyl-3-yl)-N-hydroxy-1H-benzoimidazole-5-carboxamidine 12hf: LC-ESI-HRMS of [M+H]+ shows 377.1418 Da. Calc. 377.141379 Da, dev. 1.1 ppm
1-(2',6'-Dimethoxy-biphenyl-3-yl)-N-hydroxy-1H-benzoimidazole-5-carboxamidine 12hg: LC-ESI-HRMS of [M+H]+ shows 389.1628 Da. Calc. 389.161366 Da, dev. 3.7 ppm
1-(3'-Fluoro-2'-methoxy-biphenyl-3-yl)-N-hydroxy-1H-benzoimidazole-5-carboxamidine 12hh.
1-(2'-Fluoro-6'-methoxy-biphenyl-3-yl)-N-hydroxy-1H-benzoimidazole-5-carboxamidine 12hi.
1-(2'-Chloro-6'-methoxy-biphenyl-3-yl)-N-hydroxy-1H-benzoimidazole-5-carboxamidine 12hj.
1-(2'-Chloro-6'-fluoro-3'-methyl-biphenyl-3-yl)-N-hydroxy-1H-benzoimidazole-5-carboxamidine 12hk.
1-(6'-Chloro-2'-fluoro-3'-methyl-biphenyl-3-yl)-N-hydroxy-1H-benzoimidazole-5-carboxamidine 12hl.
1-(2',4'-Dimethoxy-biphenyl-3-yl)-N-hydroxy-1H-benzoimidazole-5-carboxamidine 12hm.
1-(2',3'-Dimethoxy-biphenyl-3-yl)-N-hydroxy-1H-benzoimidazole-5-carboxamidine 12hn.
1-[3-(5-Bromo-2-fluoro-pyridin-3-yl)-phenyl]-N-hydroxy-1H-benzoimidazole-5-carboxamidine 12ho.
1-[3-(2-Bromo-5-fluoro-pyridin-4-yl)-phenyl]-N-hydroxy-1H-benzoimidazole-5-carboxamidine 12hp.
1-(2',6'-Difluoro-biphenyl-3-yl)-N-hydroxy-1H-benzoimidazole-5-carboxamidine 12hq.
1-(2',6'-Dichloro-biphenyl-3-yl)-N-hydroxy-1H-benzoimidazole-5-carboxamidine 12 hr.
N-Hydroxy-1-(2'-piperazin-1-yl-biphenyl-3-yl)-1H-benzoimidazole-5-carboxamidine 12hs. The compound is synthesized via the N-Boc-piperazine intermediate which is then deprotected.
1-[3-(2-Bromo-5-methoxy-pyridin-4-yl)-phenyl]-N-hydroxy-1H-benzoimidazole-5-carboxamidine 12ht.
1-[3-(2-Chloro-3-fluoro-pyridin-4-yl)-phenyl]-N-hydroxy-1H-benzoimidazole-5-carboxamidine 12hu.
1-(2',3'-Difluoro-6'-methoxy-biphenyl-3-yl)-N-hydroxy-1H-benzoimidazole-5-carboxamidine 12hv.
1-(4'-Fluoro-2'-methoxy-biphenyl-3-yl)-N-hydroxy-1H-benzoimidazole-5-carboxamidine 12hx.
1-(3'-Chloro-2'-hydroxy-biphenyl-3-yl)-N-hydroxy-1H-benzoimidazole-5-carboxamidine 12hy.
1-(3'-Chloro-2',6'-difluoro-biphenyl-3-yl)-N-hydroxy-1H-benzoimidazole-5-carboxamidine 12 hz.
1-[3-(2,4-Dimethoxy-pyrimidin-5-yl)-phenyl]-N-hydroxy-1H-benzoimidazole-5-carboxamidine 12haa.
1-[3-(2,6-Difluoro-pyridin-3-yl)-phenyl]-N-hydroxy-1H-benzoimidazole-5-carboxamidine 12hab.
1-[3-(3-Fluoro-pyridin-4-yl)-phenyl]-N-hydroxy-1H-benzoimidazole-5-carboxamidine 12hac.
1-[3-(3-Chloro-pyridin-4-yl)-phenyl]-N-hydroxy-1H-benzoimidazole-5-carboxamidine 12had.
1-[3-(2-Chloro-pyridin-3-yl)-phenyl]-N-hydroxy-1H-benzoimidazole-5-carboxamidine 12hae.
N-Hydroxy-1-(2'-morpholin-4-ylmethyl-biphenyl-3-yl)-1H-benzoimidazole-5-carboxamidine 12haf.
1-(3',5'-Difluoro-2'-methoxy-biphenyl-3-yl)-N-hydroxy-1H-benzoimidazole-5-carboxamidine 12haj.
N-Hydroxy-1-(2'-methanesulfonylamino-biphenyl-3-yl)-1H-benzoimidazole-5-carboxamidine 12hak,
1-[3-(2-Fluoro-pyridin-3-yl)-phenyl]-N-hydroxy-1H-benzoimidazole-5-carboxamidine 12hal: LC-ESI-HRMS of [M+H]+ shows 348.1267 Da. Calc. 348.126063 Da, dev, 1.8 ppm
1-(5'-Chloro-2'-methoxy-biphenyl-3-yl)-N-hydroxy-1H-benzoimidazole-5-carboxamidine 12ham.
3'-[5-(N-Hydroxycarbamimidoyl)-benzoimidazol-1-yl]-biphenyl-2-carboxylic acid amide 12han.

Example 5

Synthesis of Oxazoles

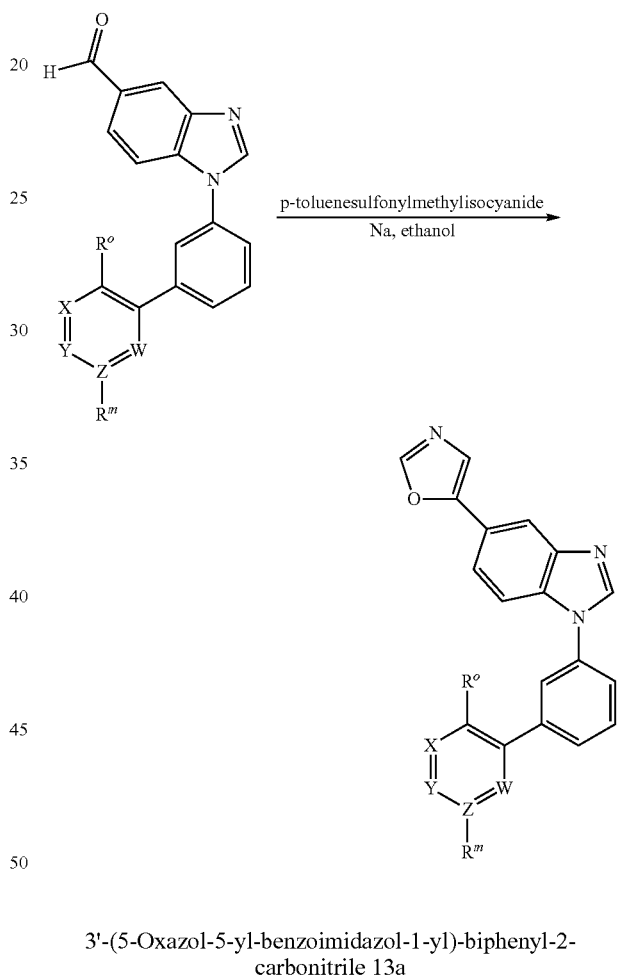

3'-(5-Oxazol-5-yl-benzoimidazol-1-yl)-biphenyl-2-carbonitrile 13a

Sodium (0.21 g, 9.3 mmol) was allowed to react with ethanol (10 ml) under nitrogen. To this solution, compound 10t (1.0 g, 3.1 mmol) was added. After stirring for 30 min, p-toluenesulfonylmethyl isocyanide (0.75 g, 3.7 mmol) was added and the resultant mixture was stirred at reflux overnight. The solvent was removed under reduced pressure and the residue was partitioned between water and dichloromethane. The organic layer was washed with brine, dried over sodium sulfate and concentrated under reduced pressure. The concentrate was purified by column chromatography on silica gel eluting with a mixture of ethyl acetate and hexane (4:1 v/v) to afford 13a (95 mg, 43%). Mp 222-226° C.

The following compounds are prepared analogously:
1-(2'-Methoxy-biphenyl-3-yl)-5-oxazol-5-yl-1H-benzoimidazole 13b from 11s.
1-(2'-Isopropoxy-biphenyl-3-yl)-5-oxazol-5-yl-1H-benzoimidazole 13c from 11v.
1-(2'-Ethoxy-biphenyl-3-yl)-5-oxazol-5-yl-1H-benzoimidazole 13d from 11x.
1-(2'-Methyl-biphenyl-3-yl)-5-oxazol-5-yl-1H-benzoimidazole 13e from 11y.
1-(2'-Ethyl-biphenyl-3-yl)-5-oxazol-5-yl-1H-benzoimidazole 13f from 11z.

Example 6

Synthesis of Compound 14

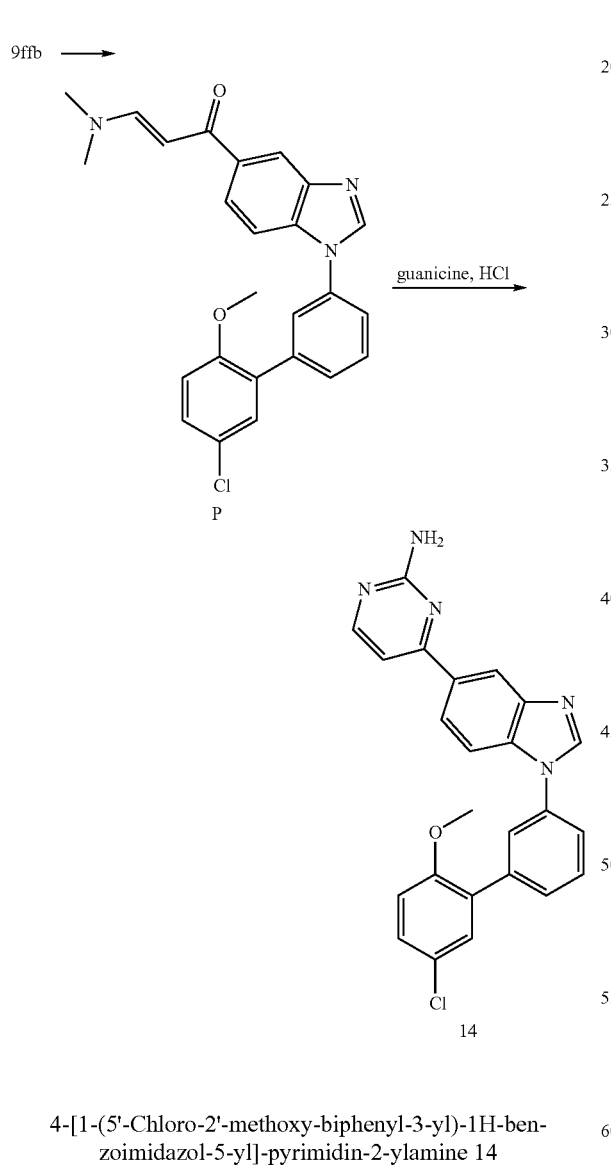

4-[1-(5'-Chloro-2'-methoxy-biphenyl-3-yl)-1H-benzoimidazol-5-yl]-pyrimidin-2-ylamine 14

Compound 9ffb was treated with DMF-DMA as described in Example 1 for the preparation of intermediate H to obtain the above enamine.

To a solution of P (2 g, 4.6 mmol) in ethanol (20 ml) was added guanidine hydrochloride (0.82 g, 13.9 mmol) together with aqueous sodium hydroxide (2.8 ml, 10M) and the resultant mixture was stirred at reflux for 3 hours. A crude product precipitates upon cooling. This is isolated and purified by column chromatography on silica gel using a mixture of dichloromethane, methanol and aqueous ammonia (97:2:1) as the eluent. Yield: 160 mg (8%). LC-ESI-HRMS of [M+H]+ shows 428.1296 Da. Calc. 428.127813 Da, dev. 4.2 ppm

Example 7

Synthesis of Compounds 15 and 16

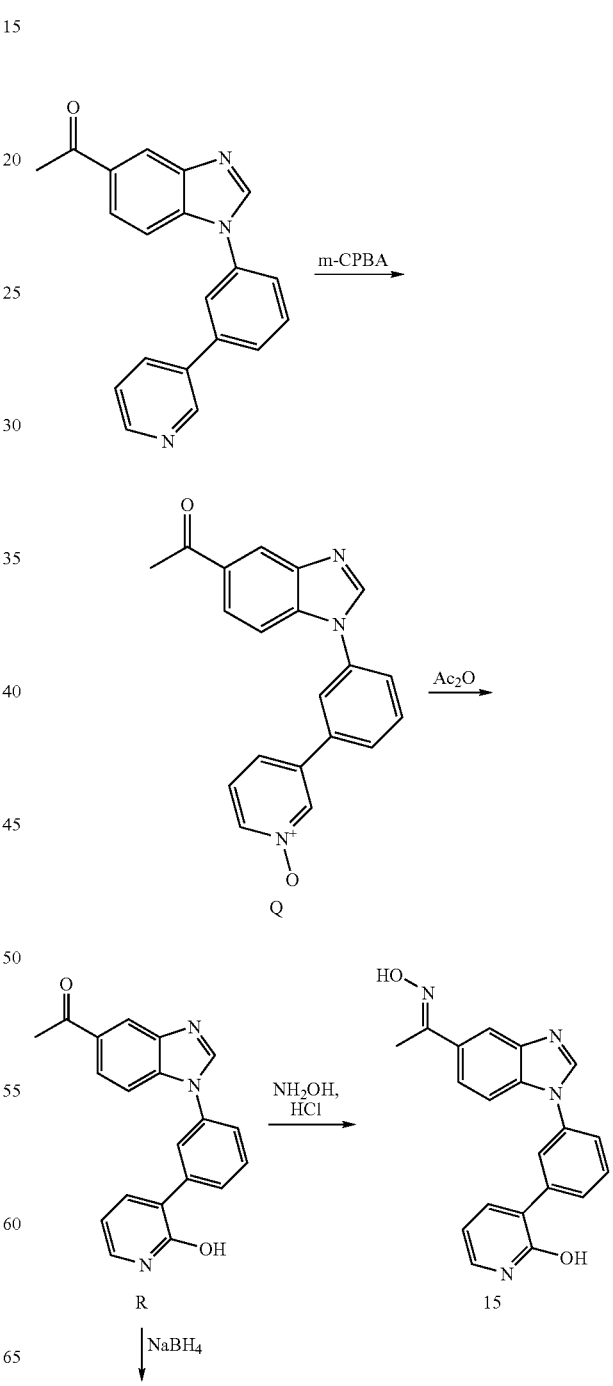

-continued

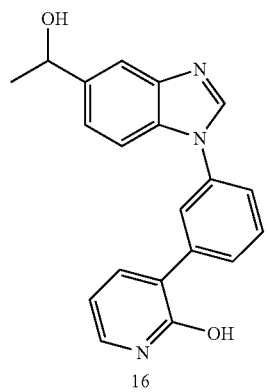

16

Synthesis of Intermediate Q

To a suspension of the ketone (WO 96/33194) (15.0 g, 47.9 mmol) in dichloroethane (450 ml) was added meta-chloroperbenzoic acid (26.0 g, 70%, 105 mmol) and the mixture was stirred at ambient conditions over night. The mixture was partitioned between saturated, aqueous sodium carbonate and dichloromethane. The organic layer was dried and evaporated to dryness. The solid residue was washed with water to afford Q (11.5 g, 73%)

Synthesis of Intermediate R

A mixture of Q (11.5 g, 35 mmol) and acetic anhydride (200 ml) was stirred at reflux for 4 hours and was then left at ambient condition over night. The reaction mixture was concentrated under reduced pressure and the residue was partitioned between saturated, aqueous sodium carbonate and ethyl acetate. The organic layer was dried and concentrated and the concentrate was dissolved in a mixture of THF and methanol and treated with activated carbon at reflux. The mixture was filtered through celite and the filtrate was evaporated. Recrystallisation of the residue from methanol afforded R (2 g)

1-{1-[3-(2-Hydroxy-pyridin-3-yl)-phenyl]-1H-benzoimidazol-5-yl}-ethanone oxime 15

This was prepared from R as described in Example 3. Mp 220-223° C.

3-{3-[5-(1-Hydroxy-ethyl)-benzoimidazol-1-yl]-phenyl}-pyridin-2-ol 16

To a solution of compound R (0.5 g, 1.5 mmol) in a mixture of DMF (9 ml) and methanol (1 ml) was added sodium borohydride (1 20 mg, 60% dispersion in mineral oil) and the resultant mixture was stirred at 60° C. over night. The cooled mixture was poured into ice-water and saturated, aqueous ammonium chloride was added. The precipitate was filtered off and purified by column chromatography on silica gel eluting with a mixture of dichloromethane, methanol and aqueous ammonia (90:9.9:0.1) to afford the desired product (0.1 g), Mp 133-137° C.

Example 8

Synthesis of Compounds 17 and 18

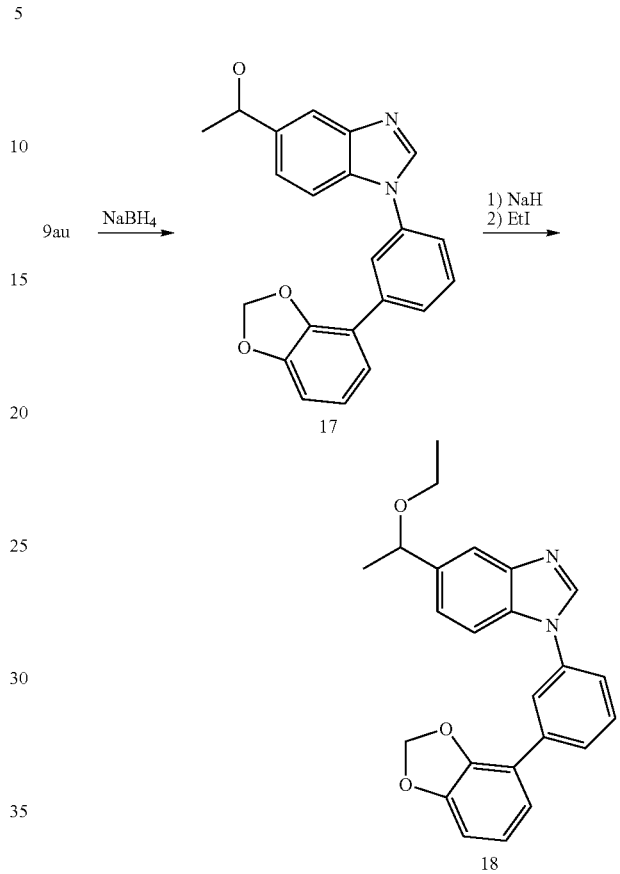

1-[1-(3-Benzo[1,3]dioxol-4-yl-phenyl)-1H-benzoimidazol-5-yl]-ethanol 17.

This was prepared from compound 9au analogously to compound 16

1-(3-Benzo[1,3]dioxol-4-yl-phenyl)-5-(1-ethoxyethyl)-1H-benzoimidazole 18

This was prepared from compound 17 by deprotonisation with sodium hydride followed by alkylation with ethyliodide using standard conditions. LC-ESI-HRMS of [M+H]+ shows 387.1705 Da. Calc. 387.170868 Da, dev. −1 ppm Example 9

Synthesis of Compound 19

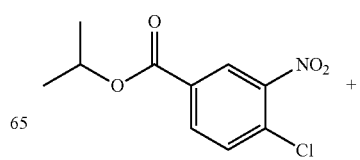

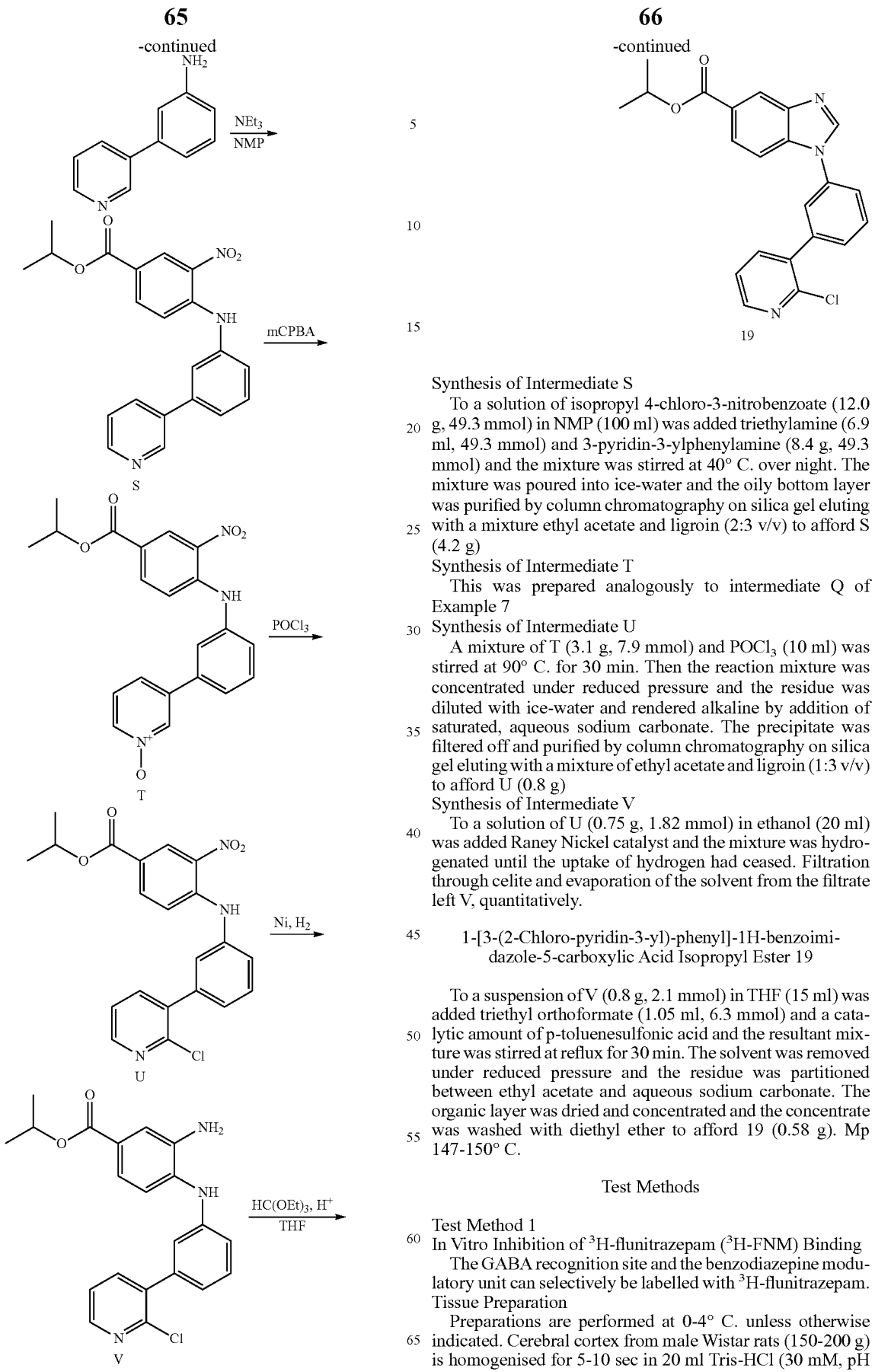

Synthesis of Intermediate S

To a solution of isopropyl 4-chloro-3-nitrobenzoate (12.0 g, 49.3 mmol) in NMP (100 ml) was added triethylamine (6.9 ml, 49.3 mmol) and 3-pyridin-3-ylphenylamine (8.4 g, 49.3 mmol) and the mixture was stirred at 40° C. over night. The mixture was poured into ice-water and the oily bottom layer was purified by column chromatography on silica gel eluting with a mixture ethyl acetate and ligroin (2:3 v/v) to afford S (4.2 g)

Synthesis of Intermediate T

This was prepared analogously to intermediate Q of Example 7

Synthesis of Intermediate U

A mixture of T (3.1 g, 7.9 mmol) and POCl$_3$ (10 ml) was stirred at 90° C. for 30 min. Then the reaction mixture was concentrated under reduced pressure and the residue was diluted with ice-water and rendered alkaline by addition of saturated, aqueous sodium carbonate. The precipitate was filtered off and purified by column chromatography on silica gel eluting with a mixture of ethyl acetate and ligroin (1:3 v/v) to afford U (0.8 g)

Synthesis of Intermediate V

To a solution of U (0.75 g, 1.82 mmol) in ethanol (20 ml) was added Raney Nickel catalyst and the mixture was hydrogenated until the uptake of hydrogen had ceased. Filtration through celite and evaporation of the solvent from the filtrate left V, quantitatively.

1-[3-(2-Chloro-pyridin-3-yl)-phenyl]-1H-benzoimidazole-5-carboxylic Acid Isopropyl Ester 19

To a suspension of V (0.8 g, 2.1 mmol) in THF (15 ml) was added triethyl orthoformate (1.05 ml, 6.3 mmol) and a catalytic amount of p-toluenesulfonic acid and the resultant mixture was stirred at reflux for 30 min. The solvent was removed under reduced pressure and the residue was partitioned between ethyl acetate and aqueous sodium carbonate. The organic layer was dried and concentrated and the concentrate was washed with diethyl ether to afford 19 (0.58 g). Mp 147-150° C.

Test Methods

Test Method 1

In Vitro Inhibition of $^3$H-flunitrazepam ($^3$H-FNM) Binding

The GABA recognition site and the benzodiazepine modulatory unit can selectively be labelled with $^3$H-flunitrazepam.

Tissue Preparation

Preparations are performed at 0-4° C. unless otherwise indicated. Cerebral cortex from male Wistar rats (150-200 g) is homogenised for 5-10 sec in 20 ml Tris-HCl (30 mM, pH 7.4) using an Ultra-Turrax homogeniser. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at −20° C.

Assay

The membrane preparation is thawed and centrifuged at 2° C. for 10 min at 27,000×g. The pellet is washed twice with 20 ml 50 mM Tris-citrate, pH 7.1 using an Ultra-Turrax homogeniser and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 μl of test solution and 25 μl of $^3$H-FNM (1 nM, final concentration), mixed and incubated for 40 min at 2° C. Non-specific binding is determined using Clonazepam (1 μM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

Results 25-75% inhibition of specific binding must be obtained, before calculation of an $IC_{50}$.

The test value will be given as $IC_{50}$ (the concentration (μM) of the test substance which inhibits the specific binding of $^3$H-FNM by 50%).

$$IC_{50} = (\text{applied test substance concentration, μM}) \times \frac{1}{\left(\frac{C_o}{C_x} - 1\right)}$$

where
$C_o$ is specific binding in control assays, and
$C_x$ is the specific binding in the test assay.
(The calculations assume normal mass-action kinetics).

Test results from these experiments with a number of compounds of the invention are shown in Table 1 below.

TABLE 1

| Test compound | In vitro binding $IC_{50}$ (μM) |
|---|---|
| Compound 9a | 0.0014 |
| Compound 9ak | 0.021 |
| Compound 9aac | 0.00065 |
| Compound 9aba | 0.0062 |
| Compound 9ada | 0.0040 |
| Compound 12ha | 0.00095 |

The invention claimed is:

1. A compound which is 2-{1-[3-(2-fluoro-pyridin-3-yl)-phenyl]-1H-benzimidazol-5-yl}-propan-2-ol; or an N-oxide thereof; or a pharmaceutically acceptable salt thereof.

2. A compound which is 2-{1-[3-(2-fluoro-pyridin-3-yl)-phenyl]-1H-benzimidazol-5-yl}-propan-2-ol; or a pharmaceutically acceptable salt thereof.

3. A compound which is 2-{1-[3-(2-fluoro-pyridin-3-yl)-phenyl]-1H-benzimidazol-5-yl}-propan-2-ol.

4. A pharmaceutical composition, comprising a therapeutically effective amount of a compound of claim 1, or an N-oxide thereof, or a pharmaceutically acceptable salt thereof, together with at least one pharmaceutically acceptable carrier, excipient or diluent.

5. A pharmaceutical composition, comprising a therapeutically effective amount of a compound of claim 2, or a pharmaceutically acceptable salt thereof, together with at least one pharmaceutically acceptable carrier, excipient or diluent.

6. A pharmaceutical composition, comprising a therapeutically effective amount of a compound of claim 3, together with at least one pharmaceutically acceptable carrier, excipient or diluent.

* * * * *